US010675345B2

(12) United States Patent
Kang et al.

(10) Patent No.: US 10,675,345 B2
(45) Date of Patent: Jun. 9, 2020

(54) RECOMBINANT INFLUENZA VIRUS VACCINES FOR INFLUENZA

(71) Applicant: Georgia State University Research Foundation, Inc., Atlanta, GA (US)

(72) Inventors: Sang-Moo Kang, Lilburn, GA (US); Yu-Na Lee, Atlanta, GA (US); Min-Chul Kim, Decatur, GA (US)

(73) Assignee: Georgia State University Research Foundation, Inc., Atlanta, GA (US)

( * ) Notice: Subject to any disclaimer, the term of this patent is extended or adjusted under 35 U.S.C. 154(b) by 0 days.

(21) Appl. No.: 15/538,133

(22) PCT Filed: Dec. 30, 2015

(86) PCT No.: PCT/US2015/068046
§ 371 (c)(1),
(2) Date: Jun. 20, 2017

(87) PCT Pub. No.: WO2016/109656
PCT Pub. Date: Jul. 7, 2016

(65) Prior Publication Data
US 2017/0368165 A1     Dec. 28, 2017

Related U.S. Application Data

(60) Provisional application No. 62/097,901, filed on Dec. 30, 2014.

(51) Int. Cl.
| *A61K 39/12* | (2006.01) |
| *A61K 39/145* | (2006.01) |
| *A61K 39/295* | (2006.01) |
| *C07K 14/005* | (2006.01) |
| *A61K 39/00* | (2006.01) |

(52) U.S. Cl.
CPC ............ *A61K 39/145* (2013.01); *A61K 39/12* (2013.01); *A61K 39/295* (2013.01); *C07K 14/005* (2013.01); *A61K 2039/55505* (2013.01); *C07K 2319/00* (2013.01); *C12N 2760/16134* (2013.01); *C12N 2760/16143* (2013.01); *C12N 2760/18534* (2013.01)

(58) Field of Classification Search
None
See application file for complete search history.

(56) References Cited

U.S. PATENT DOCUMENTS

| 2010/0247571 A1 | 9/2010 | Wong et al. |
| 2011/0318376 A1 | 12/2011 | Murata et al. |
| 2014/0255441 A1* | 9/2014 | Compans ............ C07K 14/195 424/186.1 |

FOREIGN PATENT DOCUMENTS

| KR | 2013001559 | * | 1/2013 |
| WO | 2014070848 A1 | | 5/2014 |

OTHER PUBLICATIONS

Krammer et al. (Journal of Virology, 2013, 87(12):6542-6550. (Year: 2013).*
Khurana et al., Science Translational Medicine, Jun. 2011, 3(85):85ra48. (Year: 2011).*
Deng et al., Virologica Sinica, Jun. 2012, 27(3):145-153. (Year: 2012).*
Park et al., Vaccine, 2011, 29:5481-5487. (Year: 2011).*
Kim, et al., Virus-like Particles Containing Multiple M2 Extracellular Domains Confer Improved Crossprotection Against Various Subtypes of Influenza Virus, Molecular Therapy vol. 21, No. 2, p. 485-492, 2013.
Kim, et al., Multiple heterologous M2 extracellular domains presented on virus-like particles confer broader and stronger M2 immunity than live influenza A virus infection, Antiviral Research 99, p. 328-335, 2013.
Wang, et al., Enhanced Influenza Virus-Like Particle Vaccines Containing the Extracellular Domain of Matrix Protein 2 and a Toll-Like Receptor Ligand, Clinical and Vaccine Immunology, vol. 19, No. 8, p. 119-1125, 2012.
Arévalo, et al., A dual purpose universal influenza vaccine candidate confers protective immunity against anthrax, Immunology, 150, p. 276-289, 2016.
Music, et al., Supplementation of H1N1pdm09 split vaccine with heterologous tandem repeat M2e5x virus-like particles confers improved cross-protection in ferrets, Vaccine 34, p. 466-473, 2016.
Dabaghian, et al., Vaccination with recombinant 4 × M2e.HSP70c fusion protein as a universal vaccine candidate enhances both humoral and cell-mediated immune responses and decreases viral shedding against experimental challenge of H9N2 influenza in chickens, Veterinary Microbiology 174, p. 116-126, 2014.
Ebrahimi, et al., In contrast to conventional inactivated influenza vaccines,4×M2e.HSP70c fusion protein fully protected mice against lethal dose of H1,H3 and H9 influenza A isolates circulating in Iran, Virology 430, p. 63-72, 2012.
Lucchese, et al., How a single amino acid change may alter the immunological information of a peptide, Frontiers in Bioscience E4, p. 1843-1852, 2012.

(Continued)

*Primary Examiner* — Nicole Kinsey White
(74) *Attorney, Agent, or Firm* — Thomas|Horstemeyer, LLP

(57) ABSTRACT

Disclosed are recombinant chimeric influenza virus vaccines and live attenuated influenza virus (LAIV) vaccines expressing foreign (RSV) neutralizing epitopes or conserved M2e epitopes that are capable of providing broader cross-protection against influenza virus and/or protecting against respiratory syncytial virus (RSV) without vaccine-enhanced RSV disease (ERD).

15 Claims, 48 Drawing Sheets

Specification includes a Sequence Listing.

(56) References Cited

OTHER PUBLICATIONS

Kim, et al., Immunogenicity and efficacy of replication-competent recombinant influenza virus carrying multimeric M2 extracellular domains in a chimeric hemagglutinin conjugate, Antiviral Research, vol. 148, 26, 2017.
Supplementary European Search Report, issued by the European Patent office for application EP15876250, dated Apr. 24, 2018.
International Search Report for PCT/US2015/068046 dated Mar. 11, 2016.
Lee et al., "Recombinant influenza virus carrying the conserved domain of respiratory syncytial virus (RSV) G protein confers protection against RSV without inflammatory disease," Virology, 2015, 476: 217-225.
Lee et al., "Recombinant influenza virus expressing a fusion protein neutralizing epitope of respiratory syncytial virus (RSV) confers protection without vaccine-enhanced RSV disease," Antiviral Research, 2015, 115:1-8.
Lee et al., "Protection against respiratory syncytial virus by inactivated influenza virus carrying a fusion protein neutralizing epitope in a chimeric hemagglutinin," Nanomedicine: Nanotech, Bio, and Med, 2016, 12: 759-770.
Rodrigues et al., "Influenza and Vaccinia Viruses Expressing Malaria CD8+ T and B Cell Epitopes," J Immunology, 1994, 153: 4636-4648.

Li et al., "Chimeric Influenza Virus Induces Neutraliing Antibodies and Cytotoxic T Cells against Human Immunodeficiency Virus Type 1," J Virology, 1993, 67(11): 6659-6666.
Muster et al., "Cross-neutralizing activity against divergent human immunodeficiency virus type 1 isolates induced by the gp41 sequence ELDKWAS," J Virology, 1994, 68(6): 4031-4034.
Garulli et al., "Mucosal and Systemic Immune Responses to a Human Immunodeficiency Virus Type 1 Epitope Induced upon Vaginal Infection with a Recombinant Influenza A Virus," J Virology, 2004, 78(2): 1020-1025.
Langley et al., "Induction of Neutralizing Antibody Responses to Anthrax Protective Antigen by Using Influenza Virus Vectors: Implications for Disparate Immune System Priming Pathways," J Virology, 2010, 84(16): 8300-8307.
Baets et al., "Recombinant influenza virus carrying the RSV F85-93 CTL epitope reduces respiratory syncytial virus replication in mice," J Virology, 2013, doi:10.1128/JVI.03019-12.
Fonseca et al., "A recombinant influenza virus vaccine expressing the F protein of respiratory syncytial virus," Arch Virol, 2014, 159: 1067-1077.
Doorn et al., "Evaluating the immunogenicity and safety of a BiondVax-developed universal influenza vaccine (Multimeric-001) either as a standalone vaccine or as a primer to H5N1 influenza vaccine," Medicine, 2017, 96:11(e6339).

\* cited by examiner

Wild-type HA | SP | Ectodomain | TM | CT |

Chimeric M2e4x-HA | SP | Human | L | Human | L | Sw

Reactivity to HA monoclonal antibody wt/HA | rg/M2e4x-HA
| #2 #6 #10

HA

Reactivity to M2e monoclonal antibody wt/HA | rg/M2e4x-HA
| #2 #6 #10

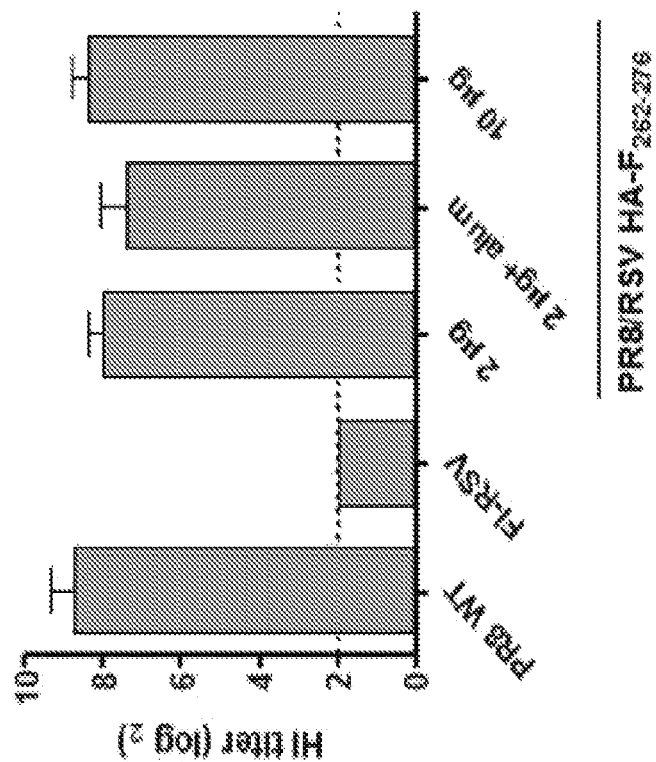

SEQUENCE LISTING

<160> NUMBER OF SEQ ID NOS: 22

<210> SEQ ID NO 1
<211> LENGTH: 11
<212> TYPE: PRT
<213> ORGANISM: Artificial Sequence
<220> FEATURE:
<223> OTHER INFORMATION: Synthetic Construct

<400> SEQUENCE: 1

Pro Ile Arg Asn Glu Trp Gly Ser Arg Ser Asn
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic Construct

<400> SEQUENCE: 2

Pro Thr Arg Ser Glu Trp Glu Ser Arg Ser Ser

<210> SEQ ID NO 3
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Asn, His, or Lys
<220> FEATURE:
<221> NAME/KEY: MISC_FEATURE
<222> LOCATION: (5)..(5)
<223> OTHER INFORMATION: Glu or Gly

<400> SEQUENCE: 3

Pro Thr Arg Xaa Xaa Trp Glu Ser Arg Ser Ser
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Synthetic Construct

<400> SEQUENCE: 4

Leu Thr Arg Asn Gly Trp Gly Cys Arg Cys Ser
1               5                   10

<210> SEQ ID NO 5
<211> LENGTH: 23
<212> TYPE: PRT
<213> ORGANISM: Artificial Sequence
<220> FEATURE:
<223> OTHER INFORMATION: Synthetic Construct

<400> SEQUENCE: 5

Ser Leu Leu Thr Glu Val Glu Thr Pro Ile Arg Asn Glu Trp Gly Ser
1               5                   10                  15

Arg Ser Asn Asp Ser Ser Asp
            20

<210> SEQ ID NO 6
<211> LENGTH: 23
<212> TYPE: PRT
<213> ORGANISM: Artificial Sequence
<220> FEATURE:
<223> OTHER INFORMATION: Synthetic Construct

<400> SEQUENCE: 6

Ser Leu Leu Thr Glu Val Glu Thr Pro Thr Arg Ser Glu Trp Glu Ser
1               5                   10                  15

Arg Ser Ser Asp Ser Ser Asp
            20

<210> SEQ ID NO 7
<211> LENGTH: 23
<212> TYPE: PRT
<213> ORGANISM: Artificial Sequence
<220> FEATURE:
<223> OTHER INFORMATION: Synthetic Construct

<400> SEQUENCE: 7

Ser Leu Leu Thr Glu Val Glu Thr Pro Thr Arg Asn Glu Trp Glu Ser

Arg Ser Ser Asp Ser Ser Asp
            20

<210> SEQ ID NO 8
<211> LENGTH: 23
<212> TYPE: PRT
<213> ORGANISM: Artificial Sequence
<220> FEATURE:
<223> OTHER INFORMATION: Synthetic Construct

<400> SEQUENCE: 8

Ser Leu Leu Thr Glu Val Glu Thr Pro Thr Arg Asn Gly Trp Glu Cys
1               5                   10                  15

Arg Cys Ser Asp Ser Ser Asp
            20

<210> SEQ ID NO 9
<211> LENGTH: 23
<212> TYPE: PRT
<213> ORGANISM: Artificial Sequence
<220> FEATURE:
<223> OTHER INFORMATION: Synthetic Construct

<400> SEQUENCE: 9

Ser Leu Leu Thr Glu Val Glu Thr Pro Thr Arg His Glu Trp Glu Cys
1               5                   10                  15

Arg Cys Ser Asp Ser Ser Asp
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic Construct

<400> SEQUENCE: 10

Ser Leu Leu Thr Glu Val Glu Thr Pro Thr Arg Lys Glu Trp Glu Cys
1               5                   10                  15

Arg Cys Ser Asp Ser Ser Asp
            20

<210> SEQ ID NO 11
<211> LENGTH: 23
<212> TYPE: PRT
<213> ORGANISM: Artificial Sequence
<220> FEATURE:
<223> OTHER INFORMATION: Synthetic Construct

<400> SEQUENCE: 11

Ser Leu Leu Thr Glu Val Glu Thr Leu Thr Arg Asn Gly Trp Gly Cys
1               5                   10                  15

Arg Cys Ser Asp Ser Ser Asp
            20

<210> SEQ ID NO 12
<211> LENGTH: 7
<212> TYPE: PRT
<213> ORGANISM: Artificial Sequence
<220> FEATURE:
<223> OTHER INFORMATION: Synthetic Construct

<400> SEQUENCE: 12

```
Ala Ala Ala Pro Gly Ala Ala
1               5

<210> SEQ ID NO 13
<211> LENGTH: 5
<212> TYPE: PRT
<213> ORGANISM: Artificial Sequence
<220> FEATURE:
<223> OTHER INFORMATION: Synthetic Construct

<400> SEQUENCE: 13

Gly Gly Gly Gly Ser
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic Construct

<400> SEQUENCE: 14

Trp Ala Ile Cys Lys Arg Ile Pro Asn Lys Lys Pro Gly
1               5                   10

<210> SEQ ID NO 15
<211> LENGTH: 9
<212> TYPE: PRT
<213> ORGANISM: Artificial Sequence
<220> FEATURE:
<223> OTHER INFORMATION: Synthetic Construct

<400> SEQUENCE: 15

Lys Tyr Lys Asn Ala Val Thr Glu Leu
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic Construct

<400> SEQUENCE: 16

Thr Glu Lys Glu Gly Ser Tyr Pro
1               5

<210> SEQ ID NO 17
<211> LENGTH: 26
<212> TYPE: PRT
<213> ORGANISM: Artificial Sequence
<220> FEATURE:
<223> OTHER INFORMATION: Synthetic Construct

<400> SEQUENCE: 17

Thr Glu Lys Glu Leu Ser Leu Ile Asn Asp Met Pro Ile Thr Asn Asp
1               5                   10                  15

Gln Lys Lys Leu Met Ser Gly Ser Tyr Pro
            20                  25

<210> SEQ ID NO 18
<211> LENGTH: 23
<212> TYPE: PRT
<213> ORGANISM: Artificial Sequence
<220> FEATURE:
<223> OTHER INFORMATION: Synthetic Construct
```

```
<400> SEQUENCE: 18

Thr Glu Lys Glu Asn Asp Met Pro Ile Thr Asn Asp Gln Lys Lys Leu
1               5                   10                  15

Met Ser Asn Gly Ser Tyr Pro
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic Construct

<400> SEQUENCE: 19

Thr Glu Lys Glu Asn Asp Met Pro Ile Thr Asn Asp Gln Lys Lys Leu
1               5                   10                  15

Gly Ser Tyr Pro
            20

<210> SEQ ID NO 20
<211> LENGTH: 18
<212> TYPE: PRT
<213> ORGANISM: Artificial Sequence
<220> FEATURE:
<223> OTHER INFORMATION: Synthetic Construct

<400> SEQUENCE: 20

Leu Ser Leu Ile Asn Asp Met Pro Ile Thr Asn Asp Gln Lys Lys Leu
1               5                   10                  15

Met Ser

<210> SEQ ID NO 21
<211> LENGTH: 15
<212> TYPE: PRT
<213> ORGANISM: Artificial Sequence
<220> FEATURE:
<223> OTHER INFORMATION: Synthetic Construct

<400> SEQUENCE: 21

Asn Asp Met Pro Ile Thr Asn Asp Gln Lys Lys Leu Met Ser Asn
1               5                   10                  15

<210> SEQ ID NO 22
<211> LENGTH: 12
<212> TYPE: PRT
<213> ORGANISM: Artificial Sequence
<220> FEATURE:
<223> OTHER INFORMATION: Synthetic Construct

<400> SEQUENCE: 22

Asn Asp Met Pro Ile Thr Asn Asp Gln Lys Lys Leu
1               5                   10
```

RECOMBINANT INFLUENZA VIRUS VACCINES FOR INFLUENZA

CROSS-REFERENCE TO RELATED APPLICATIONS

This application is the 35 U.S.C. § 371 national stage application of PCT Application No. PCT/US2015/068046, filed Dec. 30, 2015, which claims benefit of U.S. Provisional Application No. 62/097,901, filed Dec. 30, 2014, both of which are herein incorporated by reference in their entireties.

STATEMENT REGARDING FEDERALLY SPONSORED RESEARCH OR DEVELOPMENT

This invention was made with Government Support under Grant No. AI105170 and AI119366 awarded by the National Institutes of Health. The Government has certain rights in the invention.

TECHNICAL FIELD

This application is generally in the field of influenza vaccines.

BACKGROUND

Influenza virus causes one of the most important respiratory viral diseases in humans, with significant medical and economic burdens. Approximately 10% to 20% of the world population is estimated to be infected during seasonal epidemics. Influenza virus causes 250,000-500,000 deaths worldwide annually; a global pandemic could kill millions (Osterholm, M. T. N Engl J Med. 2005 352:1839-1842; Viboud, C., et al. PLoS Curr 2010 RRN1153). In the US, influenza kills an average of 17,000-51,000 people in the United States (US) per year, causes an average of over 100,000 influenza-related hospitalizations and results in an economic cost of $12 billion per year (Thompson, W. W., et al. JAMA 2004 292:1333-1340).

Influenza is a lipid-enveloped virus with a segmented negative sense RNA genome, which belongs to the family Orthomyxoviridae. The envelope of the virion contains two types of surface glycoproteins, which play essential roles in viral infection. The hemagglutinin (HA) is responsible for attachment of the virus to sialic acid-containing receptors and viral entry by membrane fusion, whereas the neuraminidase (NA) is a receptor-destroying enzyme which plays important roles in viral release and cell-to-cell spread (Matrosovich, M. N., et al. J Virol 2004 78:12665-12667; Palese, P., et al. J Gen Virol 1976 33:159-163). There are 18 identified HA subtypes and 11 recognized NA subtypes. All of these subtype combinations have been isolated in birds. Currently circulating influenza viruses in human populations contain HA and NA combinations out of three different HA subtypes (H1, H2 and H3) and 2 different NA (N1 and N2) subtypes. However, there are often outbreaks of transmissions of avian host derived influenza viruses to human population from the poultry farms (Abdel-Ghafar, A. N., et al. N Engl J Med 2008 358:261-273).

Influenza viruses undergo changes over time, allowing them to evade the host immune system and to reduce the effectiveness of immunity to prior infections or vaccinations. Influenza A viruses can change by two different means: "antigenic drift" and "antigenic shift." Point mutations in the HA and/or NA antigens generate antigenically new influenza viruses with antigenic drift that occur during viral replication. The regular recurrence of influenza epidemics is thought to be caused by antigenic drift. Over some years sufficient changes accumulate in the virus to allow repeated infections of the host with antigenically different influenza viruses. These "major antigenic shifts" result in novel antigenic subtypes of the HA and/or NA glycoproteins that had not previously infected most of the human population, and therefore can spread rapidly causing global disease pandemics. Three global pandemics of influenza occurred during the 20$^{th}$ century, and were caused by H1N1 subtype viruses in 1918, H2N2 viruses in 1957, and H3N2 viruses in 1968. In addition to the circulating human influenza subtypes, other avian origin influenza viruses including H5N1, H7N2, H7N3, H7N7 and H9N2 subtypes have been shown to cause human infections on multiple occasions (Cheung, C. L., et al. J Infect Dis 2006 193:1626-1629; de Jong, M. D., et al. N Engl J Med 353:2667-2672 2005; Fouchier, R. A., et al. Proc Natl Acad Sci USA 2004 101:1356-1361; Le, Q. M., et al. Nature 2005 437:1108; Peiris, M., et al. Lancet 1999 354:916-917; Wong, S. S., et al. Chest 2006 129:156-168). The emergence or re-emergence of highly pathogenic avian influenza H5N1 viruses in domestic poultry and the increasing numbers of direct transmission of avian viruses to humans underscore a persistent threat to public health (Claas, E. C., et al. Vaccine 1998 16:977-978; Subbarao, K., et al. Science 1998 279:393-396). Most recently, the 2009 outbreak of a new H1N1 virus illustrates how fast a new pandemic virus can spread in the human population once it acquires the ability to transmit among humans (Nava, G. M., et al. Euro Surveill 2009 14; Solovyov, A., et al. Euro Surveill 2009 14).

Inactivated influenza A and B virus vaccines have been extensively used in humans. The vaccines consist of purified virus that has been chemically inactivated with formalin or β-propiolactone, and in most vaccines the virus is also detergent-treated to produce soluble forms of the viral surface antigens. Influenza epidemics in human population contain two influenza A subtypes (H1N1 and H3N2) and one variant of influenza B virus, which become major components of being a trivalent current influenza vaccine. As an alternative approach to influenza immunization, live attenuated influenza virus (LAIV) vaccines administered by nasal spray (FluMist®) have been successfully developed. The vaccine is trivalent, containing influenza virus reassortants of the strains recommended for the current season. The currently used influenza vaccines induce immune responses to the viral surface glycoproteins HA and NA; although protective, the immunity is highly strain specific. Because these proteins undergo extensive antigenic variation, frequent changes are necessary in the vaccine composition. Although the current vaccines include proteins of the two currently circulating subtypes of influenza A viruses, they are not effective in protecting against the spectrum of different antigenic subtypes of influenza A viruses that are abundant in avian species which could potentially cause new influenza pandemics in humans.

Drifted strains that are not matched with the seasonal vaccine can appear following annual formulation of the vaccine composition, significantly compromising the vaccination efficacy. It has been suggested that approximately once every decade the mismatch between virus and vaccine is high enough to reduce vaccine effectiveness by 70%. The major limitations of the current vaccines include the need to produce new vaccines every season, the uncertainty in choice of the correct strains, long production times as well as the fact that the vaccines are produced by a slow process requiring embryonated eggs. Improved vaccines are needed, not only for seasonal influenza, but also for a potential influenza pandemic.

In contrast to HA, the influenza A M2 protein has a highly conserved extracellular domain of 23 amino acids (M2e). However, due to its small size and low immunogenicity, previous studies have focused on M2e peptide fusion constructs using a variety of carrier molecules: hepatitis B virus core (De Filette, M., et al. Vaccine 2006 24:544-551; Fan, J., et al. Vaccine 2004 22:2993-3003; Neirynck, S., et al. Nat Med 1999 5:1157-1163), human papillomavirus L protein (Ionescu, R. M., et al. J Pharm Sci 2006 95:70-79), keyhole limpet hemocyanin (Tompkins, S. M., et al. Emerg Infect Dis 2007 13:426-435), bacterial outer membrane complex (Fan, J., et al. Vaccine 2004 22:2993-3003; Fu, T. M., et al. Vaccine 2009 27:1440-1447), liposome (Ernst, W. A., et al. Vaccine 2006 24:5158-5168), and flagellin (Huleatt, J. W., et al. Vaccine 2008 26:201-214). M2 vaccines based on M2e fusion carriers or combinations of M2 expressing DNA and recombinant vectors were reported to provide cross protection against lethal infection with different strains (Ernst, W. A., et al. Vaccine 2006 24:5158-5168; Fan, J., et al. Vaccine 2004 22:2993-3003; Frace, A. M., et al. Vaccine 1999 17:2237-2244; Tompkins, S. M., et al. Emerg Infect Dis 2007 13:426-435). These studies suggested that M2e antibodies played an important role in providing protection. However, previous studies on M2e conjugate vaccines used potent adjuvants such as cholera toxins or heat labile endotoxins' derivatives, saponin QS21, Freund's adjuvants, or bacterial protein conjugates (De Filette, M., et al. Vaccine 2006 24:544-551; Eliasson, D. G., et al. Vaccine 2008 26:1243-1252; Fan, J., et al. Vaccine 2004 22:2993-3003; Fu, T. M., et al. Vaccine 2009 27:1440-1447; Huleatt, J. W., et al. Vaccine 2008 26:201-214; Mozdzanowska, K., et al. Virol J 2007 4:118). Such adjuvants that nonspecifically elicit host responses including inflammation and undesirable side effects are potentially adverse in developing a widely applicable prophylactic influenza vaccine. Moreover, the longevity and breadth of cross-protection mediated by M2 immunity remain unknown.

Respiratory syncytial virus (RSV) is a major cause of pneumonia and bronchiolitis in infants and in the elderly, resulting in more than 64 million lower respiratory tract infections and approximately 160,000 deaths annually worldwide. Vaccination of children with formalin-inactivated RSV (FI-RSV) resulted in 80% hospitalization and two deaths during epidemic season due to immune-mediated RSV disease. A particular obstacle is the safety concern of vaccine-enhanced RSV disease (ERD). Live attenuated RSV vaccine candidates also suffer from genetic instability, residual virulence, safety concerns in young infants, and lack of long-term immunity. Reinfections are common throughout life, indicating that natural RSV infection fails to establish long-lasting immunity. Many RSV vaccine platforms have been tested but not yet successful, including inactivated, live attenuated, subunit, replicating viral-vectored, and DNA vaccines. There is no licensed RSV vaccine. Therefore, it is of high priority to develop an effective and safe RSV vaccine.

SUMMARY

Disclosed are recombinant chimeric influenza virus and recombinant chimeric live attenuated influenza virus (LAIV) vaccines expressing foreign (RSV) neutralizing epitopes or conserved M2e epitopes. Also disclosed are chimeric fusion proteins containing influenza A hemagglutinin (HA) and the foreign (RSV) neutralizing epitopes or conserved M2e epitopes.

In some embodiments, a chimeric fusion protein is disclosed that comprises an HA polypeptide conjugated to one or more influenza M2e domains. For example, the fusion protein can contain tandem repeats of two or more M2e domains. In some cases the fusion protein contains at least two heterologous M2e domains. For example, the fusion protein can in some cases contain one or more M2e domains from a human influenza A subtype ("human M2e domain"), one or more M2e domains from a swine influenza A subtype ("swine M2e domain"), and one or more M2e domains from an avian influenza A subtype ("avian M2e domain"). In some embodiments, at least one M2e domain comprises a partial or full human, swine, or avian M2e domain comprising the amino acid sequence SEQ ID NO:3 or an amino acid sequence having at least 90% sequence identity to SEQ ID NO:3, and wherein at least one M2e domain comprises an avian M2e domain comprising the amino acid sequence SEQ ID NO:4 or an amino acid sequence having at least 90% sequence identity to SEQ ID NO:4.

A recombinant LAIV vaccine comprising this chimeric fusion protein can be cross-protective against two or more subtypes of influenza A with or without the use of an adjuvant. Therefore, also disclosed is a method of vaccinating a subject for influenza A comprising administering this recombinant LAIV vaccine.

In some embodiments, a chimeric fusion protein is disclosed that comprises an HA polypeptide conjugated to a neutralizing respiratory syncytial virus (RSV) fusion (F) epitope, attachment (G) epitope, or a combination thereof. A recombinant LAIV vaccine comprising this chimeric fusion protein can be protective RSV without vaccine-enhanced RSV disease (ERD).

A recombinant live attenuated influenza virus (LAIV) vaccine, comprising an influenza virus expressing a neutralizing respiratory syncytial virus (RSV) fusion (F) epitope, a neutralizing RSV attachment (G) epitope, or a combination thereof, wherein the vaccine is protective RSV without vaccine-enhanced RSV disease (ERD). Therefore, also disclosed is a method of vaccinating a subject for RSV comprising administering this recombinant LAIV vaccine.

In each of the above recombinant chimeric influenza virus constructs, the HA protein can be derived from seasonal or pandemic potential influenza virus.

In each of the above recombinant chimeric influenza virus constructs, the chimeric HA fusion protein can further comprise a signal peptide at the N-terminus or in the middle HA head domain of HA protein (i.e., in the antigenic site Sa region of H1 protein or the antigenic site B region of H3 protein which are located on the top of the HA glycoprotein).

In some embodiments, the chimeric HA protein comprises an amino acid sequence having a formula selected from the group consisting of:

$X_1$-([hM2e]$_n$-[sM2e]$_n$-[aM2e]$_n$)$_n$-$X_2$, $X_1$-([hM2e]$_n$-[aM2e]$_n$-[sM2e]$_n$)$_n$-$X_2$, $X_1$-([sM2e]$_n$-[hM2e]$_n$-[aM2e]$_n$)$_n$-$X_2$, $X_1$-([sM2e]$_n$-[aM2e]$_n$-[hM2e]$_n$)$_n$-$X_2$, $X_1$-([aM2e]$_n$-[sM2e]$_n$-[hM2e]$_n$)$_n$-$X_2$, and $X_1$-([aM2e]$_n$-[hM2e]$_n$-[sM2e]$_n$)$_n$-$X_2$;

wherein "$X_1$" consists of a signal peptide of HA protein, wherein "$X_2$" consists of an HA protein domain other than the signal peptide, wherein "hM2e" consists of a human M2e domain,
wherein "sM2e" consists of a swine M2e domain,
wherein "aM2e" consists of an avian M2e domain,
wherein each "n" is independently an integer from one to five, and
wherein "-" consists of nothing or a peptide linker or a peptide bond.

In some embodiments, the chimeric HA fusion protein comprises an amino acid sequence having a formula selected from the group consisting of:

$X_3$-[hM2e]-$X_4$, $X_3$-[sM2e]-$X_4$, and $X_3$-[aM2e]-$X_4$, wherein "$X_3$" consists of from aa1 to aa171 of an HA derived from A/PR8 virus or seasonal influenza vaccine strains (i.e., before the antigenic site Sa region of H1 protein or the antigenic site B region of H3 protein),
wherein "hM2e" consists of a human M2e domain,
wherein "sM2e" consists of a swine M2e domain,
wherein "aM2e" consists of an avian M2e domain,
wherein "$X_4$" consists of from aa172 to the end of HA derived from A/PR8 virus or seasonal influenza vaccine strains (i.e., after the antigenic site Sa region of H1 protein or the antigenic site B region of H3 protein),
wherein "-" consists of nothing or a peptide linker or a peptide bond.

In some embodiments, the chimeric HA fusion protein comprises an amino acid sequence having a formula selected from the group consisting of:

$X_1$-(hM2e-hM2e-sM2e-aM2e-aM2e)$_n$-$X_2$, $X_3$-[hM2e]-$X_4$, $X_3$-[sM2e]-$X_4$, and $X_3$-[aM2e]-$X_4$.

wherein "$X_1$" consists of a signal peptide of HA protein,
wherein "$X_2$" consists of an HA protein domain other than the signal peptide,
wherein "$X_3$" consists of from aa1 to aa171 of an HA derived from A/PR8 virus or seasonal influenza vaccine strains,
wherein "$X_4$" consists of from aa172 to the end of HA derived from A/PR8 virus or seasonal influenza vaccine strains,
wherein "hM2e" consists of a human M2e domain,
wherein "sM2e" consists of a swine M2e domain,
wherein "aM2e" consists of an avian M2e domain,
wherein each "n" is independently an integer from one to five, and
wherein "-" consists of nothing or a peptide linker or a peptide bond.

In some embodiments, the chimeric HA fusion protein comprises an amino acid sequence having a formula selected from the group consisting of:

$X_1$-[RSV G]-$X_2$, $X_1$-[RSV F]-$X_2$, $X_3$-[RSV G]-$X_4$, and $X_3$-[RSV F]-$X_4$, wherein "$X_1$" consists of a signal peptide,
wherein "$X_2$" consists of an HA protein domain other than the signal peptide,
wherein "$X_3$" consists of from aa1 to aa171 of HA derived from A/PR8 virus or seasonal influenza vaccine strains,
wherein "$X_4$" consists of from aa172 to the end of HA derived from A/PR8 virus or seasonal influenza vaccine strains,
wherein "RSV G" consists of a human RSV G central domain,
wherein "RSV F" consists of a human RSV F neutralizing domain, and
wherein "-" consists of nothing or a peptide linker or a peptide bond.

For example, in some embodiments, the RSV G central domain comprises amino acids 131-230 of RSV G protein. In addition, in some embodiments, the RSV F neutralizing domain comprises amino acids 255-275, 165-319, 228-309, 243-294, 368-497, 386-475, or 402-460 of RSV F protein.

The disclosed recombinant influenza virus can be formulated as a whole inactivated virus, split viral vaccine, or live attenuated influenza vaccine.

In some embodiments, the influenza virus used as a backbone of the disclosed recombinant influenza virus is an A/Ann Arbor/6/60 (H2N2), A/PR/8/34 (H1N1), or A/Leningrad/134/17/57 (H2N2), influenza virus type A strain.

Also disclosed is a cross-protective vaccine comprising a recombinant influenza virus disclosed herein. In some embodiments, the disclosed vaccine further comprises an adjuvant. For example, the adjuvant can be selected from the group consisting of AS04 (alum plus monophosphoryl lipid A), MF59 (oil-in-water emulsion adjuvant), or toll-like receptor agonist adjuvants (monophosphoryl lipid A plus CpG). In some embodiments, the disclosed vaccine further comprises a neuraminidase for improved cross-protection. In some embodiments, the disclosed vaccine further comprises a tandem repeat M2e vaccine for improved cross-protection.

Also disclosed are polynucleotides having nucleic acid sequences encoding the fusion proteins disclosed herein. In some cases, these polynucleotides are operably linked to an expression control sequence. Also disclosed are vectors containing these polynucleotides and cells containing these vectors.

Also disclosed is a method of vaccinating a subject for influenza A comprising administering the recombinant LAIV vaccine to a subject in need thereof by intranasal, intramuscular, subcutaneous, transdermal, or sublingual administration.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 15A to 15C show histopathological changes in lungs from mice after RSV challenge. (A) Photomicrographs of H&E, PAS, and H&CR stained lung tissue sections from mice at day 5 p.c. Scale bars for H&E and PAS indicate 100 μm and for H&CR indicate 20 μm. The insets in H&CR images are details of eosinophil infiltration in lungs. (B) Percentages of PAS positive staining. Tissue sections stained with PAS were scored as percentages of 10 individual airways in each mouse. Each symbol represents one airway. (C) Inflammation scores of H&CR staining. Pulmonary eosinophils per 40× field counts in two different regions of each mouse. Data represent mean±SEM. Statistically significance was determined by 1-way ANOVA. Asterisks indicate significant differences (***p<0.001) compared with the results in the FI-RSV group.

FIGS. 16A to 16D depict chimeric HA constructs. FIG. 16A is a schematic comparing the structure of wild-type HA to chimeric M2e4x-HA construct. FIG. 16B shows sequences for human (SEQ ID NO:5), swine (SEQ ID NO:6), and avian (SEQ ID NO:7) M2e depicted in FIG. 16A. FIG. 16C shows Connector 1 (C1, SEQ ID NO:13) and Connector 2 (C2, SEQ ID NO:12) linkers for use in construct of FIG. 16A. FIG. 16D is a graph comparing M2e reactivity of wild-type HA, M2e4x-HA using C1, and M2e4x-HA using C2.

FIGS. 17C and 17D show virus reactivity of chimeric M2e4x-HA protein to HA and M2e monoclonal antibodies.

FIG. 19A is a graph showing antibody response of prime and boost immune sera from wild-type and recombinant virus. FIG. 19B shows HAI titers to homologous A/PR8 after inoculation with recombinant or wild-type virus. FIG. 19C shows antibody levels to human, swine, and avian M2e antigens after prime and boos inoculation.

FIGS. 20A to 20E show cross-protection after inoculation with M2e4x-HA. FIGS. 20A and 20B are graphs showing body weight (%) after infection with A/California (H1N1, FIG. 20A) or A/Philippines (H3N2, FIG. 20B) in mice that received recombinant virus immune sera, wild-type virus immune sera, or naïve serum. FIG. 20C shows viral titer in lungs in mice treated with immune sera. FIGS. 20D and 20E show body weight (%) after infection with A/Mandarin duck (avian rgH5N1, FIG. 20D) or A/Vietnam (rgH5N1, FIG. 20E) in mice that received immune sera.

FIG. 21A shows sequences for PR8 $WT_{168-175}$ (SEQ ID NO:16), PR8/RSV HA-$F_{258-275}$ (SEQ ID NO:17), PR8/RSV HA-$F_{262-276}$ (SEQ ID NO:18), and PR8/RSV HA-$F_{262-273}$ (SEQ ID NO:19). FIGS. 21B and 21C show antigenic properties (FIG. 21B) and viral growth kinetics (FIG. 21C) of the chimeric constructs.

FIGS. 22A to 22D are graphs showing inactivated PR8/RSV HA-$F_{262-276}$ vaccination is effective in inducing RSV neutralizing antibodies. FIGS. 22A and 22B show RSV F-specific antibodies three weeks after boost. FIGS. 22C and 22D show virus neutralization titers (FIG. 22C) and HI titers (FIG. 22D) after immunization.

FIG. 23A shows lung virus load in mice vaccinated with PR8/RSV HA-$F_{262-276}$. FIGS. 23B to 23D show IL-5 (FIG. 23B), IL-13 (FIG. 23C), and exotoxin (FIG. 23D) levels in lung extracts in immunized mice.

FIGS. 24A to 24D show inactivated PR8/RSV HA-$F_{262-276}$ vaccine does not cause pulmonary pathology. FIG. 24A contains pulmonary histopathology images of immunized mice upon RSV infection. FIGS. 24B to 24D are bar graphs showing inflammation pathology scores of airways (FIG. 24B), blood vessels (FIG. 24C), and interstitial spaces (FIG. 24D) from the histopathology images.

DETAILED DESCRIPTION

Figure 1A:
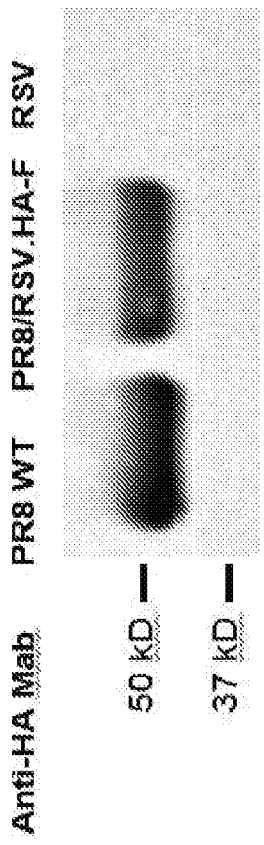
FIGS. 1A to 1E show characterization of recombinant PR8/RSV.HA-F virus in vitro and in vivo. (A) Schematic representation of WT HA and mutant HA-F constructs. (B) Western blot of PR8 WT virus, recombinant PR8/RSV.HA-F, and RSV using mouse anti-HA monoclonal antibody (IC5-4F8) or palivizumab under reducing conditions. (C) In vitro growth kinetics. Eggs were infected with a 15 EID50 (50% egg infectious dose) of PR8 WT and PR8/RSV.HA-F virus. Samples were taken at 0, 12, 24, 36, and 48 h post-infection. The viral titer in the samples was determined by EID50 assay. (D-E) Mice were inoculated intranasally with 1,000 EID50 of the PR8 WT and PR8/RSV.HA-F virus. (D) Body weight changes were monitored daily for 6 days after inoculation. (E) Lung viral titers were determined by EID50 assay at 6 days after inoculation. CT, cytoplasmic tail; TM, transmembrane domain. WT; wild-type.

Due to limitations of current vaccines in inducing cross protection against antigenically different influenza viruses, a universal vaccine that is based on the relatively conserved domains of the influenza virus is disclosed. Also disclosed is a recombinant live attenuated influenza virus (LAIV) vaccines expressing foreign (RSV) neutralizing epitopes.

The extracellular domain of the influenza M2 protein (M2e) remains nearly invariant among different strains (Liu, W., et al. Microbes Infect 2005 7:171-177), suggesting that M2 would be a promising candidate antigen for developing universal influenza vaccines. Previous studies have focused on influenza A vaccines based on the small extracellular domain of M2 (M2e), attempting to develop universal vaccines. Due to poor immunogenicity of M2e, chemical or genetic conjugates of M2e to carrier vehicles were most often used and protective efficacies were determined using a mouse model. However, severe weight loss and incomplete protection were reported even with using potent adjuvants (Andersson, A. M., et al. PloS one 2012 7:e46395; De Filette, M., et al. Vaccine 2006; De Filette, M., et al. J Biol Chem 283:11382-11387 2008; Eliasson, D. G., et al. Vaccine 2008 26:1243-1252; Ernst, W. A., et al. Vaccine 2006 24:5158-5168; Fan, J., et al. Vaccine 2004 22:2993-3003; Jegerlehner, A., et al. J Immunol 2004 172:5598-5605; Tompkins, S. M., et al. Emerg Infect Dis 2007 13:426-435; Wu, F., et al. Vaccine 2009 27:4320-4324). In the virion, M2 immunogenicity is low because it is a small protein potentially masked by the major surface glycoproteins, and because it is presented in low amounts.

Most children are infected with RSV or affected by RSV-associated disease by 2 to 3 years of age. RSV is the leading cause of high mortality and hospitalizations worldwide in infants, the elderly, and high-risk patients. Formalin inactivated RSV vaccines caused vaccine enhanced respiratory disease. Replicating vaccinia virus-vectored vaccines expressing the full-length RSV attachment (G) or fusion (F) proteins have been tested but may have safety concerns. Many RSV vaccine platforms have been tested but not yet successful partially because of safety concerns.

Disclosed are molecular design and genetic engineering techniques that overcome challenging difficulties of low immunogenicity of M2e as a universal vaccine. Disclosed novel findings include the generation of recombinant chimeric influenza viruses expressing HA fusion chimeric proteins with highly conserved M2e proteins, which provide broader cross protection against different strains of influenza viruses.

Also disclosed are recombinant chimeric influenza viruses containing protective RSV epitopes in an HA fusion proteins, which can confer protection against RSV infection without vaccine-enhanced RSV disease (ERD).

Definitions

It must be noted that as used herein and in the appended claims, the singular forms "a," "an," and "the" include plural referents unless the context clearly dictates otherwise. Thus, for example, reference to "a peptide" includes a plurality of such peptides, reference to "the peptide" is a reference to one or more peptides and equivalents thereof known to those skilled in the art, and so forth.

In this specification and in the claims that follow, reference will be made to a number of terms that shall be defined to have the following meanings:

"Optional" or "optionally" means that the subsequently described event or circumstance can or cannot occur, and that the description includes instances where the event or circumstance occurs and instances where it does not. For example, the phrase "optionally a signal peptide" means that the signal peptide may or may not be included.

The term "universal influenza A vaccine" refers to vaccine capable of providing cross-protection against at least two, including three, four, five or more, subtypes of influenza A.

The term "individual," "host," "subject," and "patient" are used interchangeably to refer to any individual who is the target of administration, treatment, or vaccination. The subject can be a vertebrate, for example, a mammal. Thus, the subject can be a human or veterinary patient.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The terms "peptide," "protein," and "polypeptide" are used interchangeably to refer to a natural or synthetic molecule comprising two or more amino acids linked by the carboxyl group of one amino acid to the alpha amino group of another.

The term "protein domain" refers to a portion of a protein, portions of a protein, or an entire protein showing structural integrity; this determination may be based on amino acid composition of a portion of a protein, portions of a protein, or the entire protein.

The term "nucleic acid" refers to a natural or synthetic molecule comprising a single nucleotide or two or more nucleotides linked by a phosphate group at the 3' position of one nucleotide to the 5' end of another nucleotide. The nucleic acid is not limited by length, and thus the nucleic acid can include deoxyribonucleic acid (DNA) or ribonucleic acid (RNA).

The term "variant" refers to an amino acid sequence having conservative amino acid substitutions, non-conservative amino acid substitutions (i.e. a degenerate variant), or a peptide having 60%, 65%, 70%, 71%, 72%, 73%, 74%, 75%, 76%, 77%, 78%, 79%, 80%, 81%, 82%$, 83%, 84%, 85%, 86%, 87%, 88%, 89%, 90%, 91%, 92%, 93%, 94%, 95%, 96%, 97%, 98%, or 99% sequence identity to the recited sequence.

The term "percent (%) sequence identity" or "homology" is defined as the percentage of nucleotides or amino acids in a candidate sequence that are identical with the nucleotides or amino acids in a reference nucleic acid sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

A "fusion protein" refers to a polypeptide formed by the joining of two or more polypeptides through a peptide bond formed between the amino terminus of one polypeptide and the carboxyl terminus of another polypeptide. The fusion protein can be expressed as a single polypeptide from nucleic acid sequence encoding the single contiguous fusion protein. A single chain fusion protein is a fusion protein having a single contiguous polypeptide backbone. Fusion proteins can be prepared using conventional techniques in molecular biology to join the two genes in frame into a single nucleic acid, and then expressing the nucleic acid in an appropriate host cell under conditions in which the fusion protein is produced.

A "spacer" or "linker" as used herein refers to a peptide that joins the proteins of a fusion protein. Generally a spacer has no specific biological activity other than to join the proteins or to preserve some minimum distance or other spatial relationship between them. However, the constituent amino acids of a spacer may be selected to influence some property of the molecule, such as the folding, net charge, or hydrophobicity of the molecule.

Fusion Proteins

Disclosed are chimeric fusion proteins for use in recombinant chimeric influenza virus vaccines expressing highly conserved M2e proteins or RSV neutralizing epitopes, and/or recombinant chimeric live attenuated influenza vaccines (LAIVs) expressing highly conserved M2e proteins or RSV neutralizing epitopes. Fusion proteins, also known as chimeric proteins, are proteins created through the joining of two or more genes which originally coded for separate proteins. Translation of this fusion gene results in a single polypeptide with function properties derived from each of the original proteins. Recombinant fusion proteins can be created artificially by recombinant DNA technology for use in biological research or therapeutics.

The functionality of fusion proteins is made possible by the fact that many protein functional domains are modular. In other words, the linear portion of a polypeptide which corresponds to a given domain, such as a tyrosine kinase domain, may be removed from the rest of the protein without destroying its intrinsic enzymatic capability. Thus, any of the herein disclosed functional domains can be used to design a fusion protein.

A recombinant fusion protein is a protein created through genetic engineering of a fusion gene. This fusion typically involves an insertion of the second protein at the beginning of the first protein or removing the stop codon from a cDNA sequence coding for the first protein, then appending the cDNA sequence of the second protein in frame through ligation or overlap extension PCR. That DNA sequence will then be expressed by a cell as a single protein. The protein can be engineered to include the full sequence of both original proteins, or only a portion of either.

If the two entities are proteins, often linker (or "spacer") peptides are also added which make it more likely that the proteins fold independently and behave as expected. Especially in the case where the linkers enable protein purification, linkers in protein or peptide fusions are sometimes engineered with cleavage sites for proteases or chemical agents which enable the liberation of the two separate proteins.

Chimeric HA-M2e Fusion Constructs

Chimeric HA-M2e fusion proteins are disclosed that contain one or more M2 ectodomain (M2e) epitope sequences conjugated to the N-terminal or head domain of the influenza A hemagglutinin (HA) protein. In some embodiments, the disclosed vaccine comprises a fusion protein containing heterologous M2 ectodomain (M2e) epitope sequences from different influenza types. For example, the fusion protein can contain at least 2, 3, 4, 5, or more different M2e peptides from 2, 3, 4 or more influenza types. The fusion protein can comprise at least 2, 3, 4, 5, or more heterologous M2e domains. In some embodiments, the fusion protein contains M2e peptides from human, swine, and avian (e.g., H5, H7, H9, or any combination thereof) influenza subtypes. As an example, the fusion protein can contain the following five influenza A virus subtype M2e sequences: 2× Human, 1× Swine, 1× Avian Type I, and 1× Avian Type II.

In some embodiments, the human M2e sequence comprises the amino acid sequence PIRNEWGSRSN (SEQ ID NO:1), or a conservative variant thereof having at least about 70%, 80%, or 90% sequence identity to SEQ ID NO:1 (i.e., one, two, or three conservative amino acid substitutions). For example, human M2e isolates H1N1 (A/PR8, A/NC/99) and H3N2 (A/Phil/82) have the amino acid sequence SLLTEVET PIRNEWGSRSN DSSD (SEQ ID NO:5).

In some embodiments, amino acids that are conserved across species are maintained, e.g., Arg at position three and nine, Trp at position six, and Cys at position eight of SEQ ID NO:1. In other embodiments, conserved residues are conservatively substituted, e.g., Arg to Lys. In some embodiments, amino acids that are unique to a given species are conserved to increase heterogeneity and cross-protection, e.g., Ile at position two and Asp at position eleven of SEQ ID NO:1.

In some embodiments, the swine M2e sequence comprises the amino acid sequence PTRSEWESRSS (SEQ ID NO:2), or a conservative variant thereof having at least 70%, 80%, or 90% sequence identity to SEQ ID NO:2. For example, swine M2e isolates from the 2009 H1N1 pandemic (A/California/4/2009) have the amino acid sequence SLLTEVET PTRSEWESRSS DSSD (SEQ ID NO:6).

In some embodiments, the avian M2e sequence (referred to herein as "avian type I") comprises the amino acid sequence PTRX$_1$X$_2$WESRSS (SEQ ID NO:3), wherein X$_1$ is N, H, or K, wherein X$_2$ is E or G, or a conservative variant thereof having at least 70%, 80%, or 90% sequence identity to SEQ ID NO:3. For example, avian type I M2e isolates from H5N1 (A/Vietnam/1203/04, A/Indonesia/05, A/mandarin/kr/2010, A/ck/kr/2006) have the amino acid sequence SLLTEVET PTRNEWESRSS DSSD (SEQ ID NO:7). Avian type I M2e isolates from H7N3 (A/dk/Kr/2007), H9N2 (A/ck/Kr/2012) have the amino acid sequence SLLTEVET PTRNGWECRCS DSSD (SEQ ID NO:8). Avian type I M2e isolates from H5N1 (A/ck/Kr/Gimje/2008) have the amino acid sequence SLLTEVET PTRHEWECRCS DSSD (SEQ ID NO:9). Avian type I M2e isolates from H5N1 (A/ck/Vietnam/2011) have the amino acid sequence SLLTEVET PTRKEWECRCS DSSD (SEQ ID NO:10).

In some embodiments, the avian M2e sequence (referred to herein as "avian type II") comprises the amino acid sequence LTRNGWGCRCS (SEQ ID NO:4), or a conservative variant thereof having at least 70%, 80%, or 90% sequence identity to SEQ ID NO:4. For example, avian type II M2e isolates from H5N1 (A/HK/156/97), H9N2 (A/HK/1073/99) have the amino acid sequence SLLTEVET LTRNGWGCRCS DSSD (SEQ ID NO:11).

To increase heterogeneity, the fusion protein can contain at least one avian type I M2e domain comprising the amino acid sequence SEQ ID NO:2 or 3 or an amino acid sequence having at least 70%, 80%, or 90% sequence identity to SEQ ID NO:2 or 3.

HA-RSV Fusion Constructs

Chimeric HA fusion proteins are disclosed that contain one or more neutralizing respiratory syncytial virus (RSV) G or F epitope sequences conjugated to the N-terminal or head domain of the influenza A hemagglutinin (HA) protein.

In some embodiments, the neutralizing RSV epitope comprises RSV fusion (F) protein, or an antigenic fragment thereof. An example sequence for RSV F protein can be found at Accession No. AC083301. In some embodiments, the fusion protein comprises amino acids 228-309 of an RSV F glycoprotein. In some embodiments, the fusion protein comprises amino acids 243-294 of an RSV F glycoprotein. In some embodiments, the fusion protein comprises amino acids 255-275 of an RSV F glycoprotein. In some embodiments, the fusion protein comprises amino acids 258-275 of an RSV F glycoprotein. In some embodiments, the fusion protein comprises amino acids 262-276 of an RSV F glycoprotein. In some embodiments, the fusion protein comprises amino acids 262-273 of an RSV F glycoprotein. Alternative RSV F neutralizing epitopes sequences include amino acids 165-319, 368-497, 386-475, 402-460.

In some embodiments, the neutralizing RSV epitope comprises RSV attachment (G) protein, or an antigenic fragment thereof. An example sequence for RSV G protein can be found at Accession No. AIY60644. In some embodiments, the RSV attachment (G) protein comprises amino acids 130-230 of an RSV G glycoprotein. In some embodiments, the fusion protein comprises amino acids 164-176 of an RSV G glycoprotein.

Vaccine Compositions

Disclosed are vaccine compositions that comprise one or more of the fusion proteins described above. Although not required, the vaccine compositions optionally contain one or more immunostimulants. An immunostimulant refers to essentially any substance that enhances or potentiates an immune response (antibody or cell-mediated) to an exogenous antigen. One preferred type of immunostimulant is an adjuvant.

Many adjuvants contain a substance designed to protect the antigen from rapid catabolism, such as aluminum hydroxide or mineral oil, and a stimulator of immune responses, such as monophosphoryl lipid A. The adjuvant may be a submicron oil-in-water emulsion of a metabolizable oil and an emulsifying agent. For example, the adjuvant may comprise MF59™, which is a sub-micron oil-in-water emulsion of a squalene, polyoxyethylene sorbitan monooleate (Tween™ 80) and sorbitan trioleate. The adjuvant may also be a combination of the TLR4 agonist MPL (3-O-desacyl-4'-monophosphoryl lipid A) and aluminum salt, e.g., AS04 (GlaxoSmithKline, Philadelphia, Pa.).

Combinations

The disclosed vaccine can be used to supplement existing human vaccines to improve cross protection. Therefore, the disclosed vaccine can further include (or be administered in combination with) a whole inactivated virus, split viral vaccine, live attenuated influenza vaccine, or an influenza virus-like particle (VLP) vaccine. For example, the disclosed vaccine can be combined with a trivalent inactivated vaccine (TIV) (e.g., containing killed A/H1N1, A/H3N2, and B), trivalent live attenuated influenza vaccine, trivalent split vaccines, or trivalent subunit influenza vaccines.

The disclosed vaccine can further include (or be administered in combination with) one or more of classes of antibiotics, steroids, analgesics, anti-inflammatory agents, anti-histaminic agents, or any combination thereof.

Methods of Vaccinating a Subject

A method of vaccinating a subject for influenza A is disclosed that involves administering the disclosed cross-protective influenza vaccine to a subject in need thereof. The disclosed vaccine may be administered in a number of ways. For example, the disclosed vaccine can be administered intramuscularly, intranasally, or by microneedle in the skin. The compositions may be administered orally, intravenously, subcutaneously, transdermally (e.g., by microneedle), intraperitoneally, ophthalmically, vaginally, rectally, sublingually, or by inhalation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. A typical dosage of the disclosed vaccine used alone might range from about 1 µg/kg to up to 100 mg/kg of body weight or more per vaccination, such as 10 µg/kg to 50 mg/kg, or 50 µg/kg to 10 mg/kg, depending on the factors mentioned above.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Recombinant Influenza Virus (PR8/RSV.HA-F) Expressing an RSV $F_{243-294}$ Neutralizing Epitope in the Hemagglutinin (HA) as a Chimeric Protein Materials and Methods Construction of PR8/RSV.HA-F Cells and viruses including influenza virus A/PR/8/1934 (H1N1, abbreviated PR8) virus and FI-RSV were obtained. Recombinant viruses were rescued using the pHW2000-based eight-plasmid system (Hoffmann, E., et al., 2000. Proc Natl Acad Sci USA 97, 6108-6113). The RSV $F_{727-882}$ nucleotide fragment (Genbank accession number FJ614814) was ligated between the 3' end of the HA signal peptide and the nucleotide encoding the N-terminal domain of the HA1 ectodomain of pHW2000-HA plasmid using a strategy similar to that described by Li et al. (Li, Z. N., et al., 2005. J Virol 79, 10003-10012). The inserted sequence was followed by an AAAPGAA (SEQ ID NO:12) peptide linker helping to facilitate the proper folding of the inserted fragment as an independent domain (HA-F, FIG. 1A).

To generate recombinant virus PR8/RSV.HA-F, 293T cells were cotransfected with the chimeric HA-F (FIG. 1A) gene along with the remaining gene segments derived from the PR8 strain. After 48 h post-transfection, the supernatant was harvested and then inoculated into embryonated chicken eggs. After 72 h post-inoculation, the presence of the rescued recombinant virus was confirmed by hemagglutination of chicken red blood cells. Characterization of the PR8/RSV.HA-F virus was performed by western blot using mouse anti-HA monoclonal antibody IC5-4F8 (BEI resources, Manassas, Va.) and palivizumab (MedImmune, Gaithersburg, Md.).

Immunizations and RSV Challenge of Mice

For animal experiments, 6- to 8-week-old female BALB/c mice (n=5; Harlan Laboratories) were intranasally immunized with 500 $EID_{50}$ dose (50% egg infective dose, $EID_{50}$) of PR8/RSV.HA-F and PR8 wild-type (PR8 WT) or $2\times10^5$ PFU of RSV A2 strain or phosphate-buffered saline (PBS) under isoflurane anesthesia. The FI-RSV control group was intramuscularly immunized with 50 μl of FI-RSV (2 μg) precipitated with aluminium hydroxide adjuvant (2 mg/ml) (Prince, G. A., et al., 2001. The Journal of general virology 82, 2881-2888). Blood samples were collected at 7 weeks after immunization. Immunized mice were challenged with RSV A2 strain ($2\times10^5$ PFU) or a lethal dose ($2\times LD_{50}$) of PR8 influenza virus at 8 weeks after immunization. The individual lungs and bronchoalveolar lavage fluid (BALF) samples were collected aseptically at day 5 post-challenge (p.c.), and lung homogenates were prepared as described (Kwon, Y. M., et al., 2014. Antiviral Res 104, 1-6). All animal experiments presented in this study were approved by the Georgia State University IACUC review boards (IACUC A11026).

Pulmonary Histology of RSV-Infected Mice

For histological analysis of lung tissues, the lungs were fixed in 10% neutral buffered formalin for 24 hrs, transferred to 70% ethanol, embedded in paraffin, sectioned into a thickness of 5 μm and stained with hematoxylin and eosin (H&E), periodic acid-Schiff stain (PAS) or hematoxylin and congo red (H&CR) (Meyerholz, D. K., et al., 2009. Toxicologic pathology 37, 249-255). At least ten sections per mouse were obtained for histopathologic analysis. For numerical assessment of histopathology and pneumonia in lung tissues, the bronchioles, vessels and interstitial space were initially scored on a scale of 0 to 3 by blinded observers using a previously described severity scoring system (Meyerholz, D. K., et al., 2009. Toxicologic pathology 37, 249-255).

Results

Figure 1B:
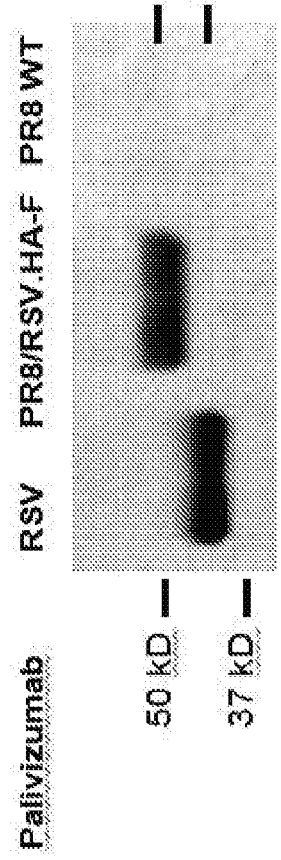

Generation of Recombinant Influenza Virus Containing an RSV F Neutralizing Epitope As a proof-of-concept, the PR8 influenza virus reverse genetics system was used to explore whether a recombinant influenza virus carrying an RSV F neutralizing epitope could provide protection against RSV. The N-terminus of HA was reported to be a site where relatively long foreign gene segments could be inserted without interfering with the biological function of HA (Hatziioannou, T., et al., 1999. Hum Gene Ther 10, 1533-1544). The RSV F domain of amino acids 243-294 ($F_{243-294}$) selected in this example contains the RSV F neutralizing epitope amino acids 255 to 275, the antigenic site II of F, which is recognized by palivizumab (Synagis) (McLellan, J. S., et al., 2011. J Virol 85, 7788-7796). Since the $F_{225-275}$ epitope has a linear conformation, a longer length of F fragment might be effective in forming a native-like structure of F epitopes present in RSV. A chimeric recombinant influenza virus containing the RSV $F_{243-294}$ domain in the N-terminal HA after the signal peptide was generated (PR8/RSV.HA-F, FIG. 1). The expression of the chimeric HA-F protein in recombinant PR8/RSV was observed in a slightly lifted position by western blot when probed either by HA specific monoclonal antibody or RSV F epitope specific monoclonal antibody palivizumab (FIG. 1B).

Figure 1C:
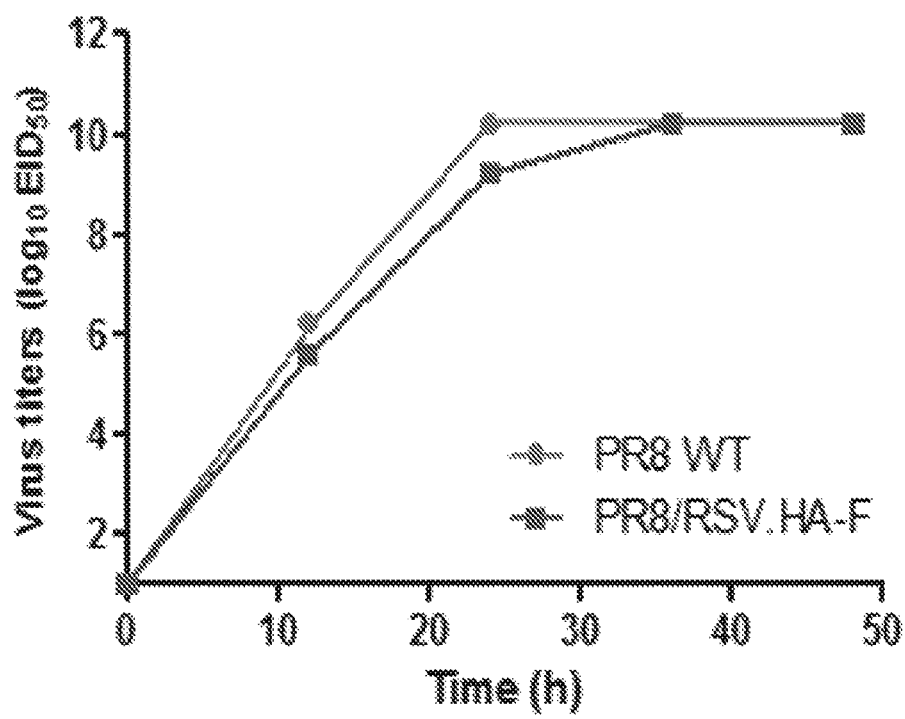

To determine in vitro viral growth kinetics, eggs were infected at a 15 $EID_{50}$ of PR8 WT or PR8/RSV.HA-F. The viral titers in allantoic fluids were quantified by an egg infectious dose ($EID_{50}$) assay at various times after infection (FIG. 1C). The growth kinetics of PR8/RSV.HA-F resembled that of PR8 WT virus. Moreover, PR8/RSV.HA-F maintained the chimeric HA-F expression over multiple passages, indicating its genetic stability.

Figure 1D:
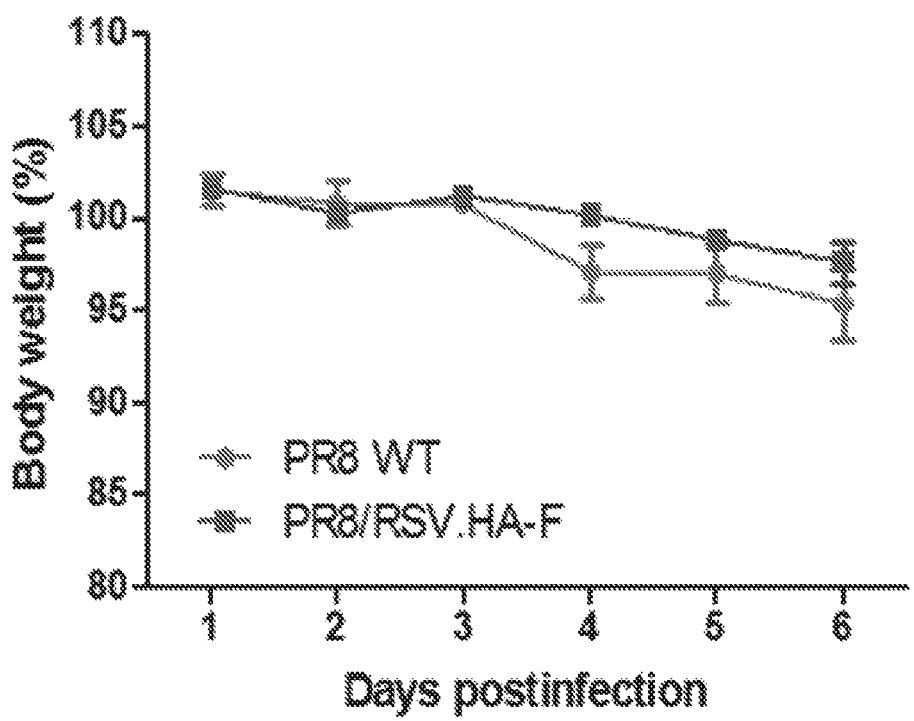
Figure 1E:
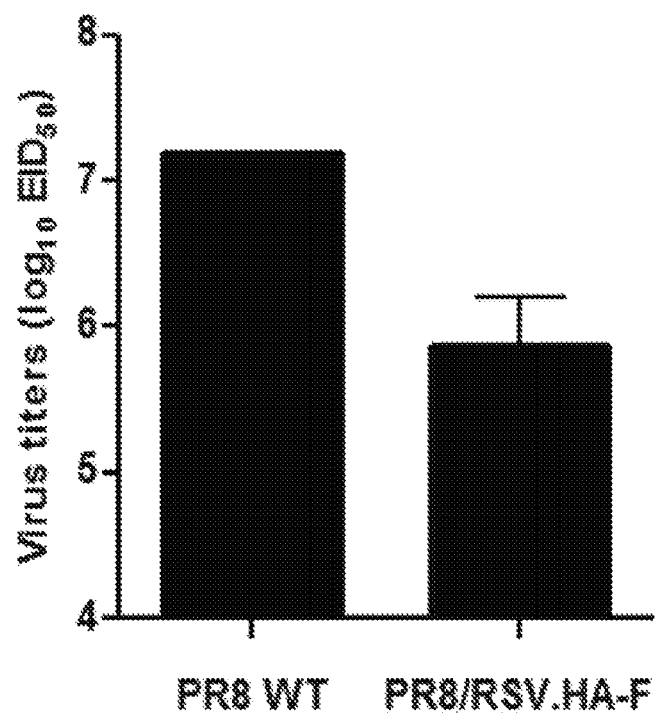

To compare the pathogenicity of PR8/RSV.HA-F virus and PR8 WT, mice were infected with 1,000 $EID_{50}$ of each virus. PR8/RSV.HA-F virus caused slightly less morbidity than the PR8 WT virus (FIG. 1D). The lung viral titers of the PR8/RSV.HA-F group were 21.5-fold lower than those in the PR8 WT group, but there was no significant difference between groups (FIG. 1E). In contrast to similar growth kinetics in eggs, a recombinant PR8/RSV.HA-F virus was slightly less pathogenic than PR8 WT virus in mice.

PR8/RSV.HA-F Virus Induces RSV Neutralizing Antibodies

Figure 2A:
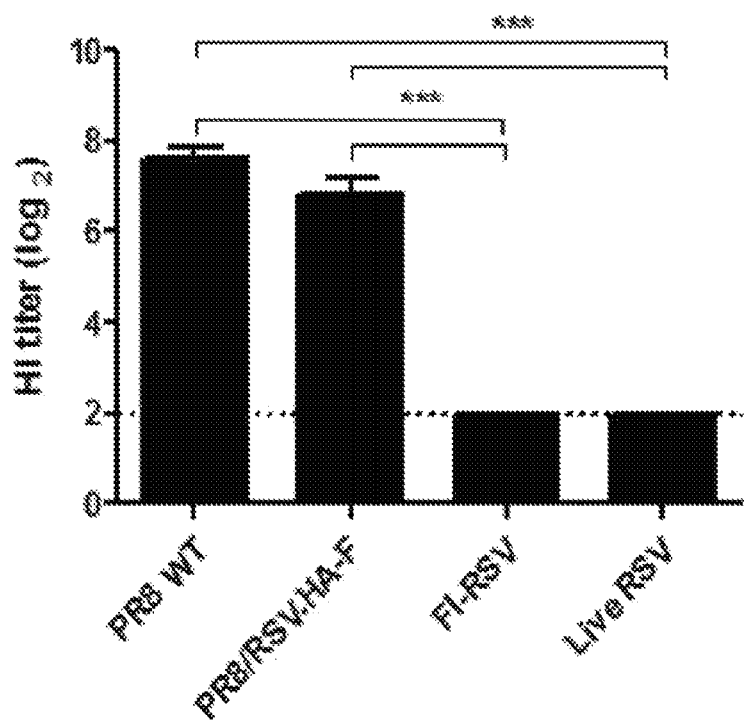
FIGS. 2A to 2C show immunogenicity of recombinant PR8/RSV.HA-F virus in mice. Mice were inoculated intranasally with 500 EID50 of the PR8 WT and PR8/RSV.HA-F virus or 2×105 P indicate significant differences (p<0.01, and *p<0.001) compared with the results in the FI-RSV.
Figures 8A, 8B:
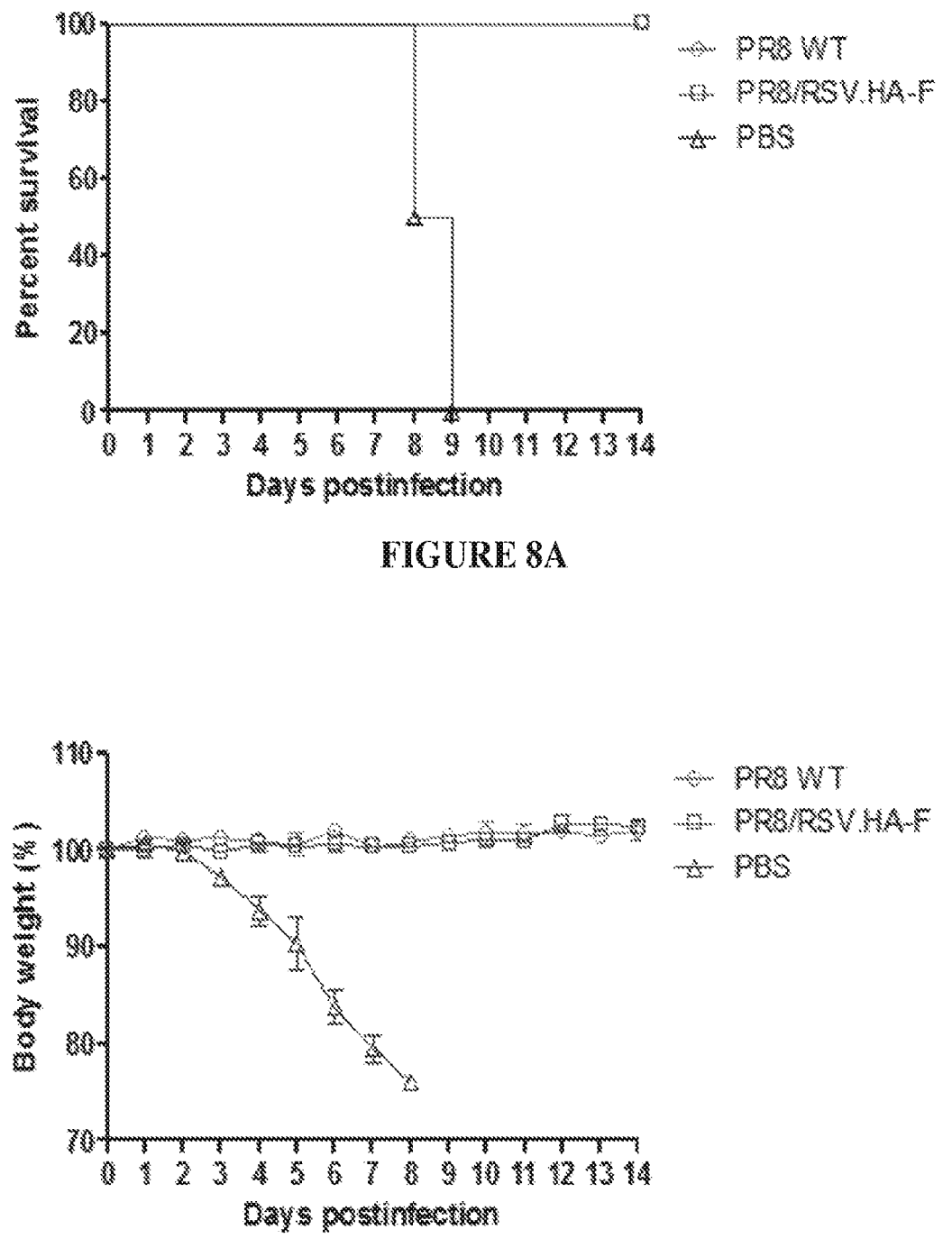

For immunization studies, a dose of 500 $EID_{50}$ was chosen that was found to induce immune responses but did not cause weight loss or disease symptoms. Immunogenicity of recombinant PR8/RSV.HA-F virus was determined in mice that received a single intranasal immunization with PR8/RSV.HA-F or PR8 WT. Influenza virus and RSV-specific antibody responses were measured using HI and neutralization assays at 7 weeks after immunization (FIG. 2). PR8 WT and PR8/RSV.HA-F groups showed high titers of HI activity up to 7.6±0.2 log 2 and 6.8±0.4, respectively (FIG. 2A). Influenza virus neutralizing titers in sera from PR8 WT and PR8/RSV.HA-F groups were significantly higher than those from the FI-RSV and live RSV groups. Also, mice that were inoculated with PR8 WT or PR8/RSV.HA-F virus were well protected against influenza virus lethal infection (FIGS. 8A and 8B).

Figure 2B:
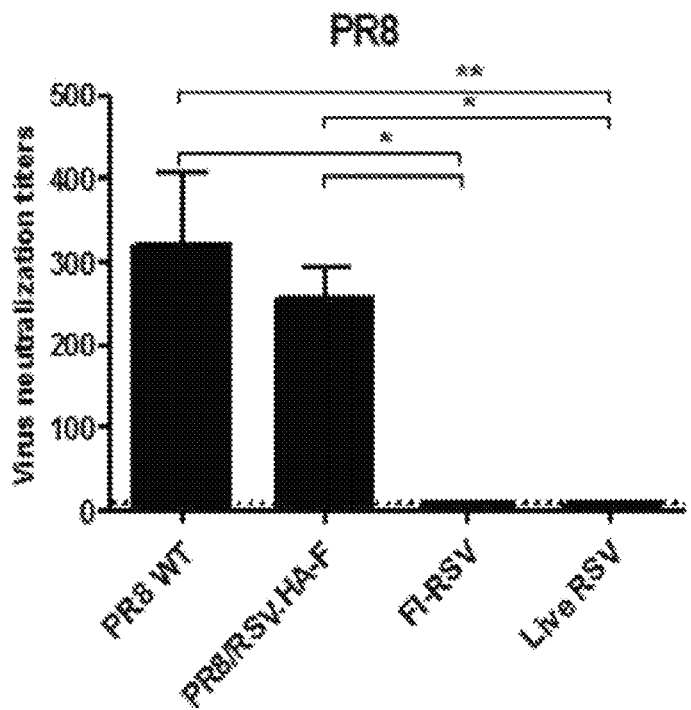
Figure 2C:
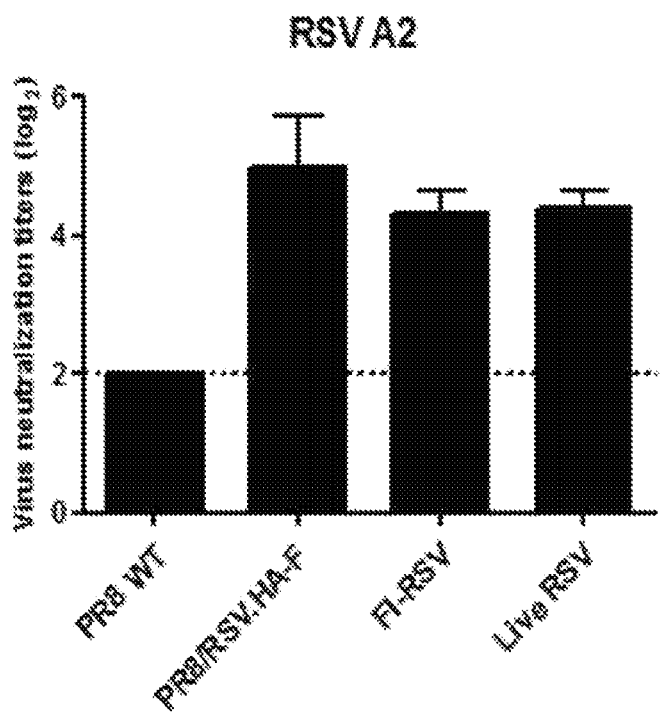

Moreover, PR8/RSV.HA-F showed high neutralizing antibody titers of 5.0±0.7 log 2 against RSV similar to that of live RSV infection or FI-RSV immunization sera (FIG. 2B). There were no significant differences in RSV neutralizing titers between the recombinant PR8/RSV.HA-F and FI-RSV-immunized groups.

Recombinant PR8/RSV.HA-F Virus Confers Protection Against RSV

Figure 3A:
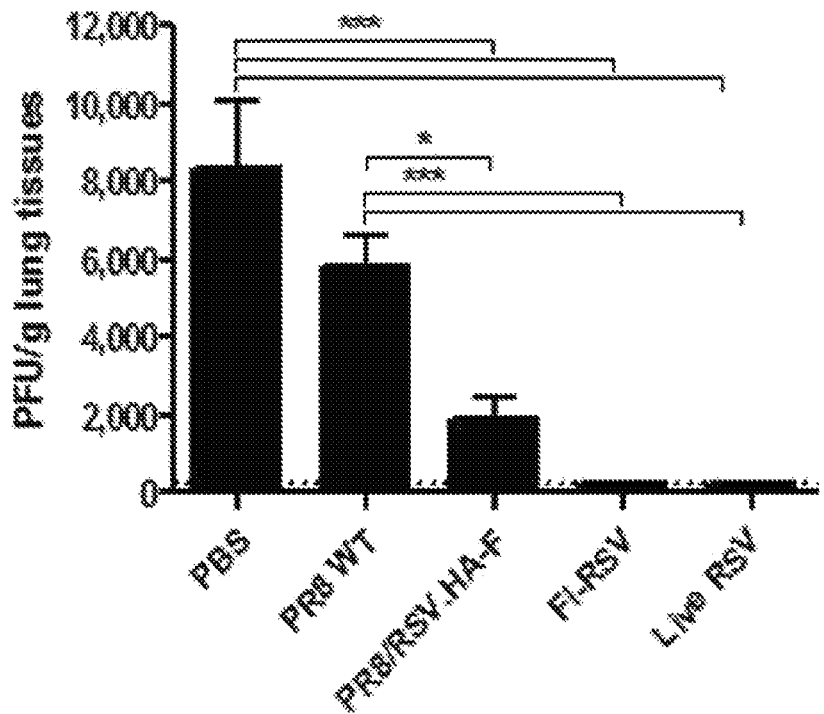
Figure 3B:
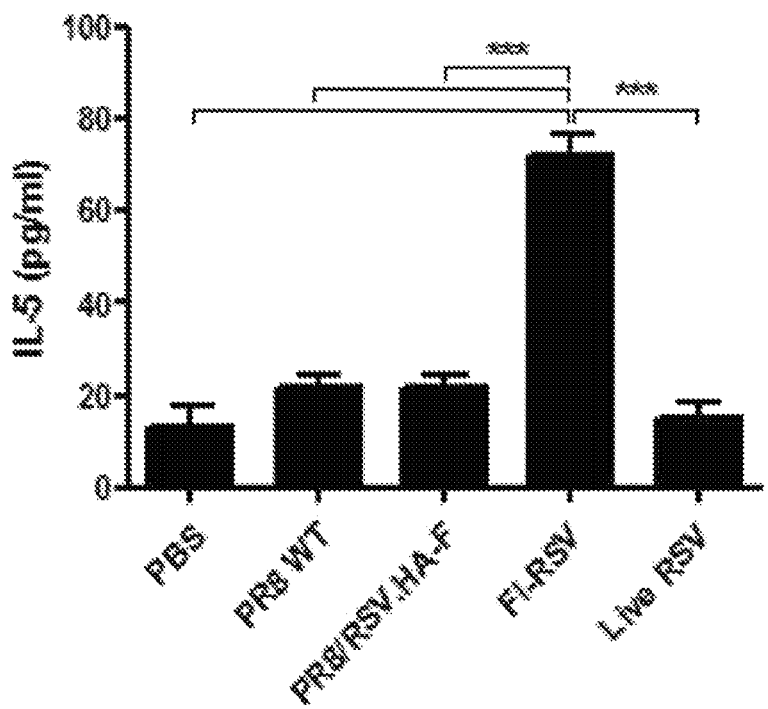
Figure 3C:
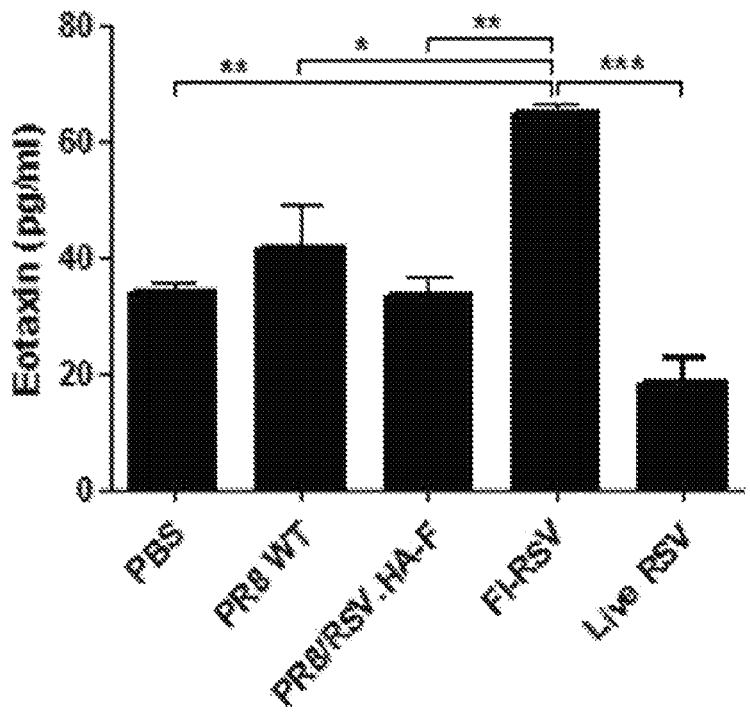

To assess the protective efficacy of recombinant PR8/RSV.HA-F vaccine, groups of mice were challenged with RSV A2 ($2\times10^5$ PFU/mouse) at 8 weeks after immunization. A dose of $2\times10^5$ PFU was chosen that was recently reported to be sufficient to assess the efficacy of RSV vaccines (Garg, R., et al., 2014. J Gen Virol 95, 1043-1054; Johnson, T. R., et al., 2014. Mol Ther 22, 196-205; Kim, E., et al., 2014. J Virol 88, 5100-5108; Murata, Y., et al., 2012. Vaccine 30, 5382-5388; Nguyen, T. N., et al., 2012. PLoS One 7, e34331; Schmidt, M. R., et al., 2012. J Virol 86, 11654-11662). PBS or PR8 WT group of mice that were infected with $2\times10^5$ PFU RSV showed a high titer of approximately up to $10^4$ PFU from lungs at day 5 post infection (FIG. 3A). Groups of mice that were intranasally inoculated with recombinant PR8/RSV.HA-F or live RSV or intramuscularly immunized with FI-RSV displayed significantly lower lung RSV titers compared with those in PBS-immunized mice (p<0.001, FIG. 3A). Cytokine and chemokine levels in BALF were determined at day 5 p.c. The levels of IL-5 (FIG. 3B) and eotaxin (FIG. 3C) in mice immunized with FI-RSV were significantly higher than those in the PR8/RSV.HA-F or other groups.

Figure 4A:
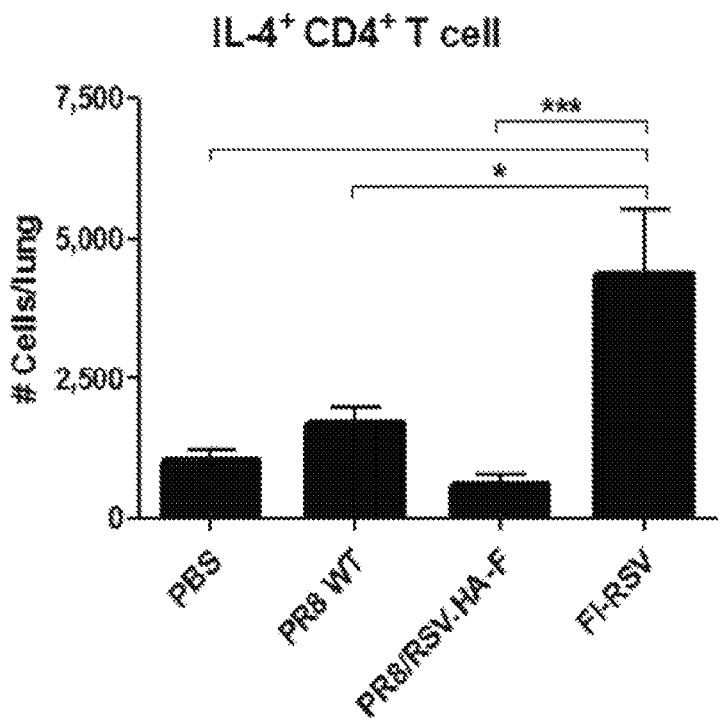
Figure 4B:
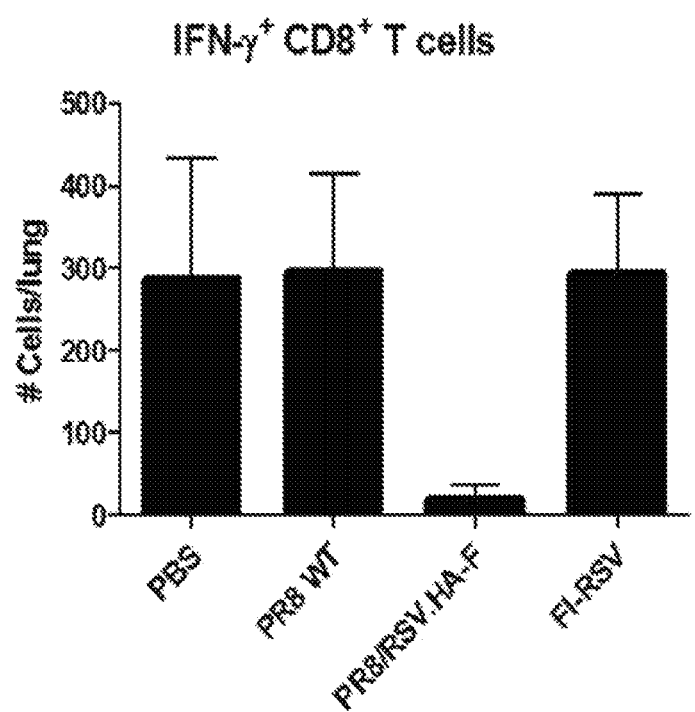

To determine T cell responses, IFN-γ or IL-4 cytokine-producing lung cells were measured after in vitro stimulation with $G_{183-195}$ and $F_{85-93}$ peptide by intracellular cytokine flow cytometry analysis (FIG. 4). Immunization with PR8/RSV.HA-F did not induce $G_{183-195}$-specific IL-4-producing CD4$^+$ T cells at a substantial level in contrast to the FI-RSV group that showed high levels of IL-4-producing CD4$^+$ T cells (p<0.001, FIG. 4A). Furthermore, IFN-γ-producing $F_{85-93}$-specific CD8$^+$ T cells were also low in the PR8/RSV.HA-F group (FIG. 4B). It was reported that IFN- γ-producing F-specific CD8$^+$ T cells were induced in the lungs from PBS-immunized (placebo) mice after RSV infection (De Baets, S., et al., 2013. J Virol 87, 3314-3323; Garg, R., et al., 2014. J Gen Virol 95, 1043-1054; Johnson, J. E., et al., 2013. Immunol Lett 150, 134-144). Concordant with these findings, PBS, PR8 WT, and FI-RSV groups showed small numbers of IFN-γ-producing F$_{85-93}$-specific CD8$^+$ T cells compared to IL-4-producing CD4+ T cells, and there was no significant difference among the groups. Also, the live RSV group did not show significant levels of IL-4- or IFN-γ-producing T cell responses.

Figure 5A:
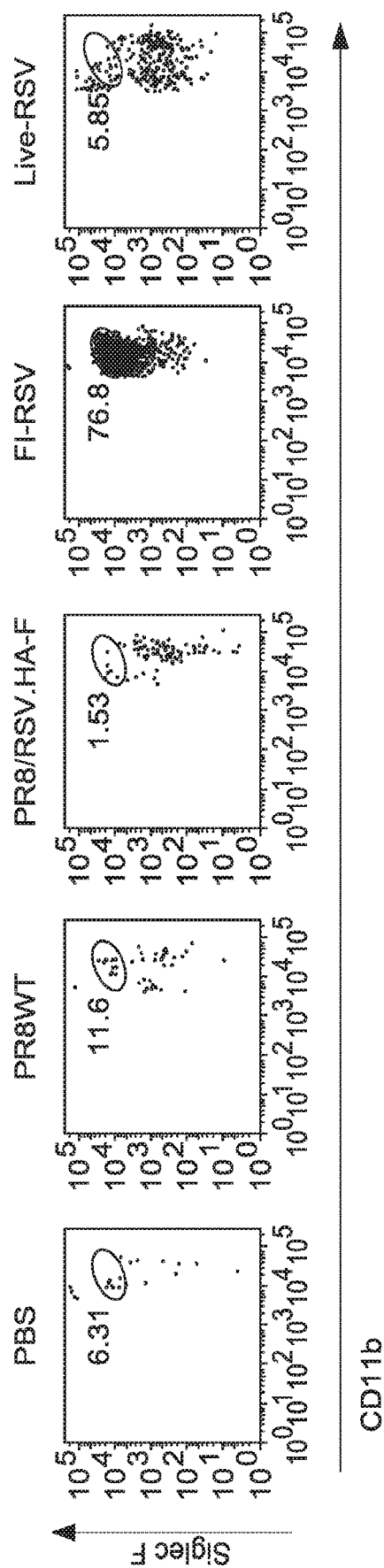
Figure 5B:
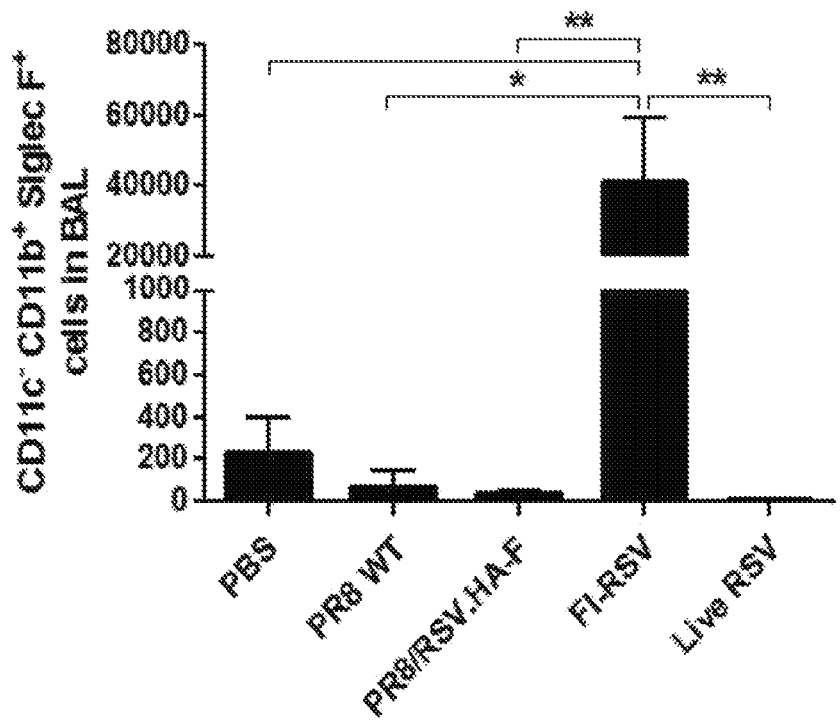
Figure 5C:
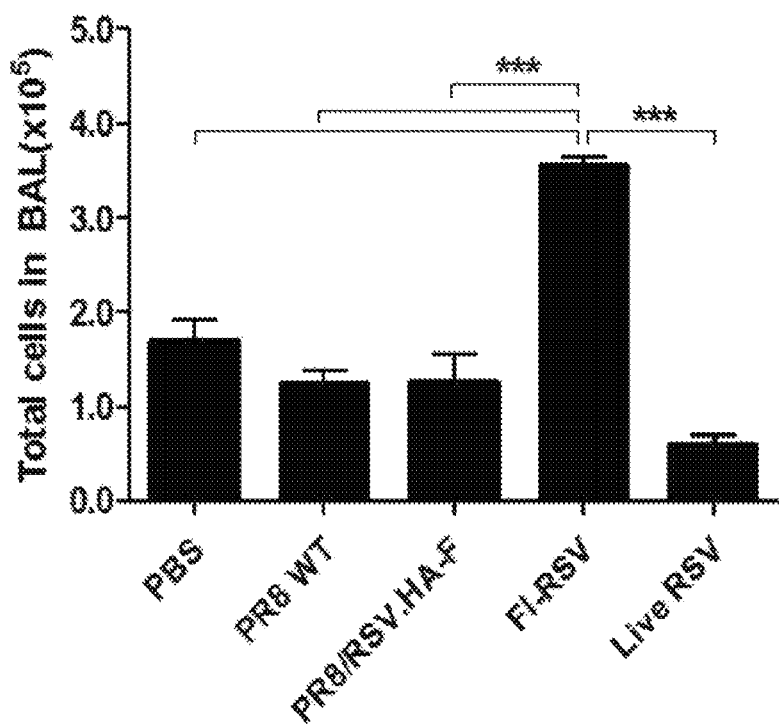

PR8/RSV.HA-F Immunization does not Induce Eosinophil Infiltration Upon RSV Infection Eosinophils are known to have the phenotypes of CD45$^+$ CD11c$^-$CD11b$^+$ Siglec F$^+$ in inflammatory tissues (Stevens, W. W., et al., 2007. J Immunol Methods 327, 63-74). At day 5 p.c., eosinophils were markedly enhanced in brochoalveolar airway fluids from the FI-RSV group (FIGS. 5A and 5B). However, the group of PR8/RSV.HA-F, PR8 WT, or live RSV mice did not show such a distinct population of CD11b$^+$SiglecF$^+$ cells in BAL fluids (FIGS. 5A and 5B). Moreover, cellularity of infiltrating cells in BAL fluids was significantly higher from mice in the FI-RSV group compared to those from recombinant PR8/RSV.HA-F or other groups (FIG. 5C).

Recombinant PR8/RSV.HA-F Virus does not Cause Pulmonary RSV Disease

Figure 6A:
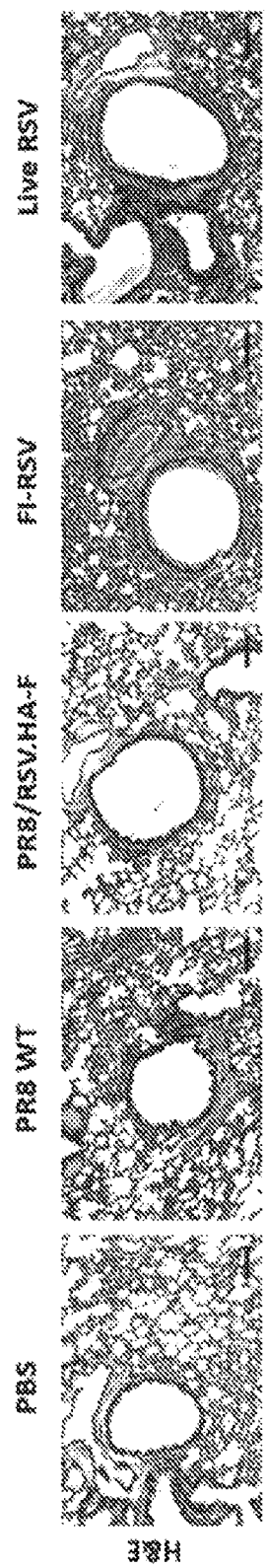
Figure 6B:
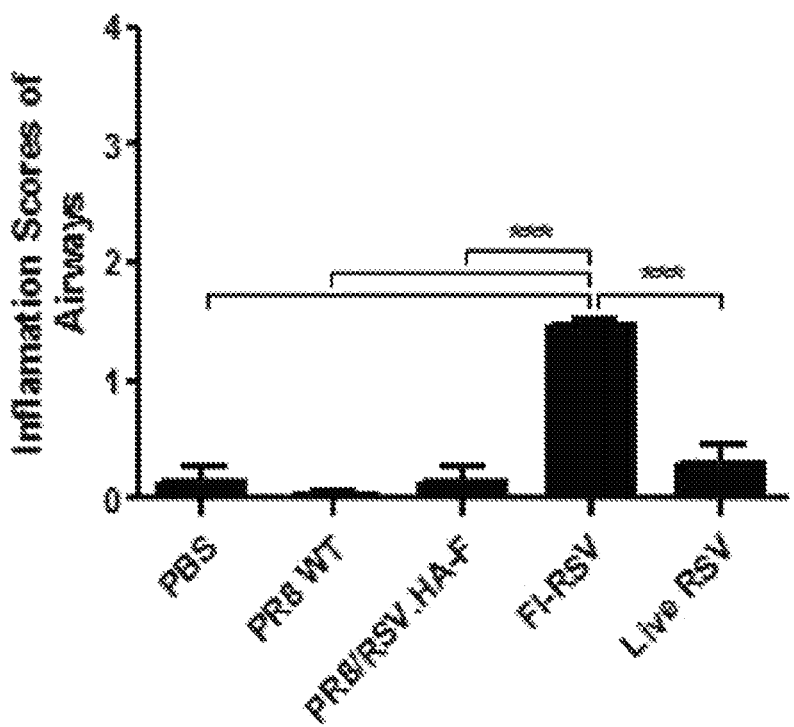
Figure 6C:
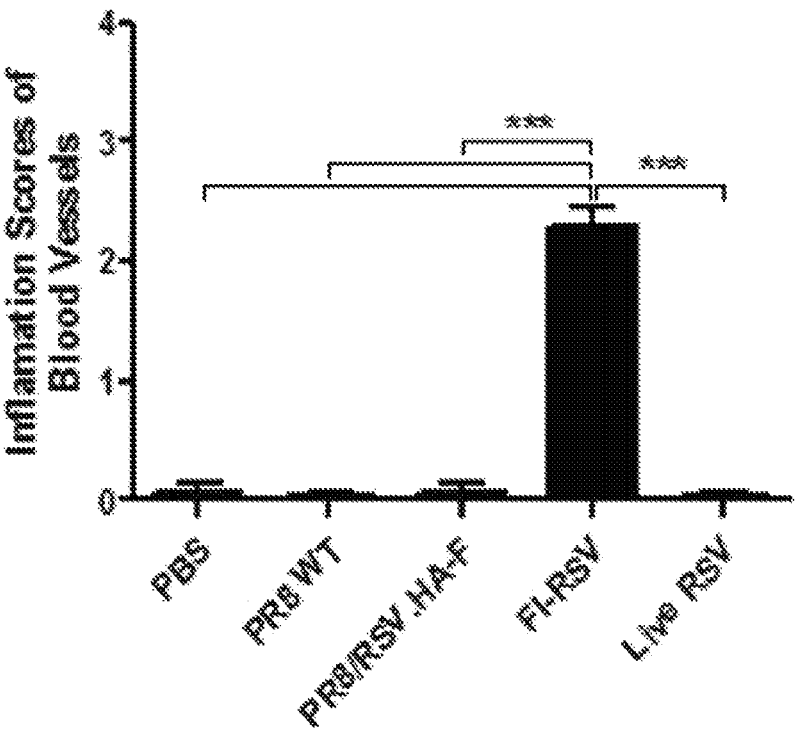
Figure 6D:
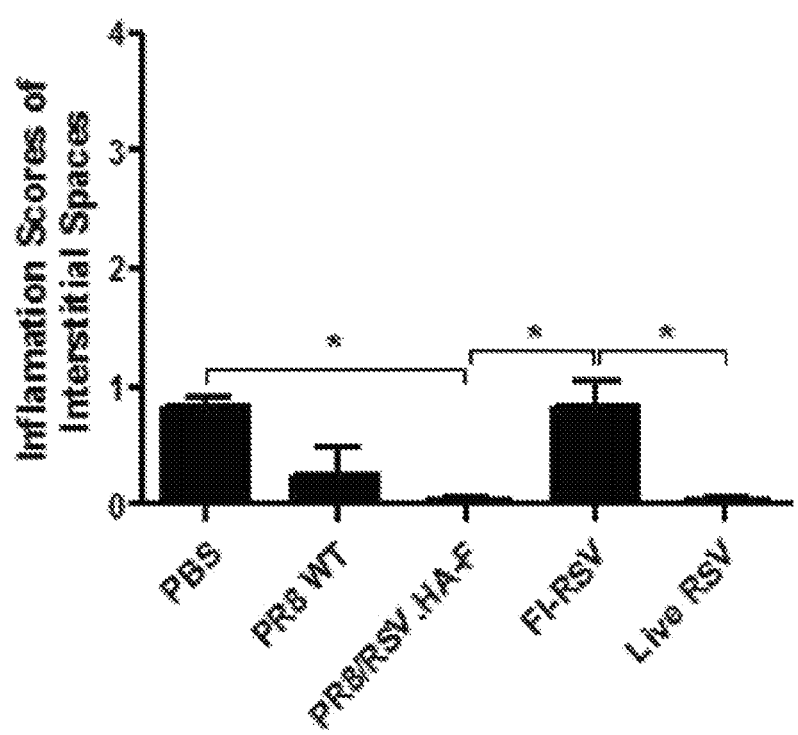

Pulmonary histopathology is an important parameter for assessing the safety of RSV vaccine candidates in preclinical studies. Lung samples from FI-RSV immunized mice showed a massive influx of inflammatory cells around pulmonary airways (pathology score 1.5, FIG. 6A, 6B), blood vessels (pathology score 2.3, FIG. 6A, 6C), and in the peribronchial and perivasicular spaces (pathology score 0.8, FIG. 6A, 6D) as well as epithelial cell thickening of airway linings. Thus, despite lung viral control, FI-RSV immunization of mice induced severe inflammatory histopathology of lungs upon RSV infection. In contrast, lung tissues from the mice immunized with PR8/RSV.HA-F and live RSV did not show overt inflammation. Alveolar epithelium appeared to be normal in lung tissue histology from mice that were immunized with PR8/RSV.HA-F. PBS-immunized RSV-challenged mice showed a low level of cellular infiltration in the interstitial area (FIG. 6D), as previously reported (Blanco, J. C., et al., 2014. Vaccine 32, 1495-1500; Castilow, E. M., et al., 2008. Future Virol 3, 445-454; Cherukuri, A., et al., 2012. Immun Ageing 9, 21; Smith, G., et al., 2012. PLoS One 7, e50852).

Figure 7A:
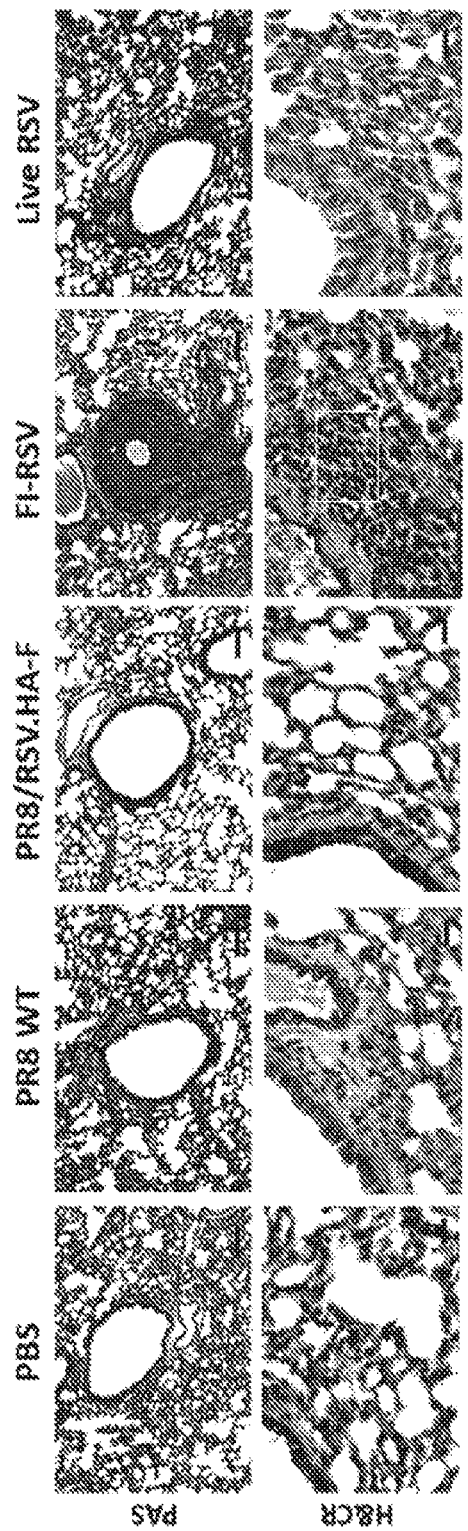
Figure 7B:
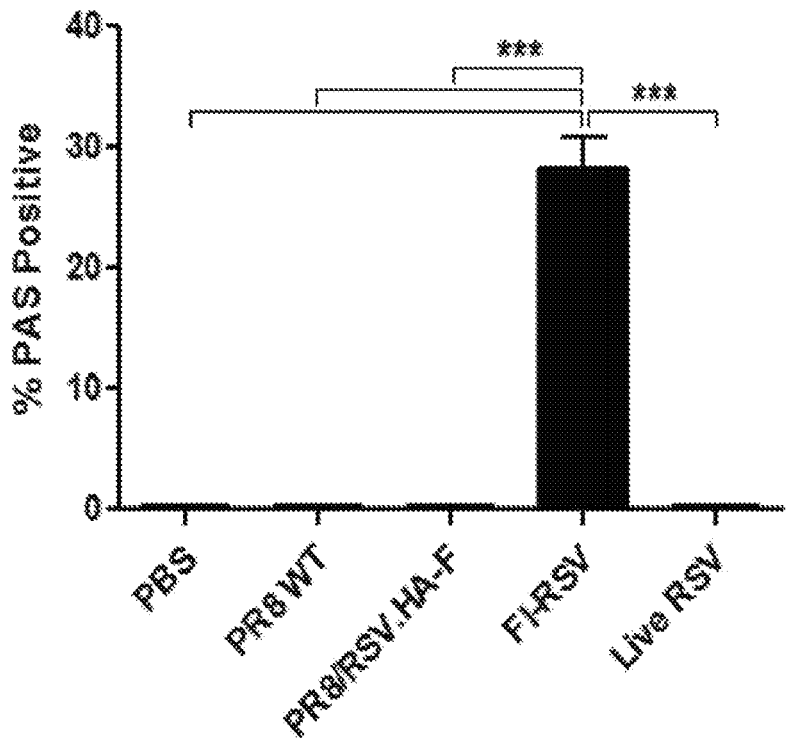

Mucus production is another characteristic observed in severe inflammatory RSV lung disease, which can be detected by PAS staining (Jafri, H. S., et al., 2004. J Infect Dis 189, 1856-1865). To visualize mucus-associated carbohydrate materials, lung sections from mice were stained with PAS (FIG. 7A). Airway linings showing PAS staining were presented by quantitative scores (FIG. 7B). PR8/RSV.HA-F-immunized mice showed no PAS stained-linings along the airways (FIG. 7B).

Figure 7C:
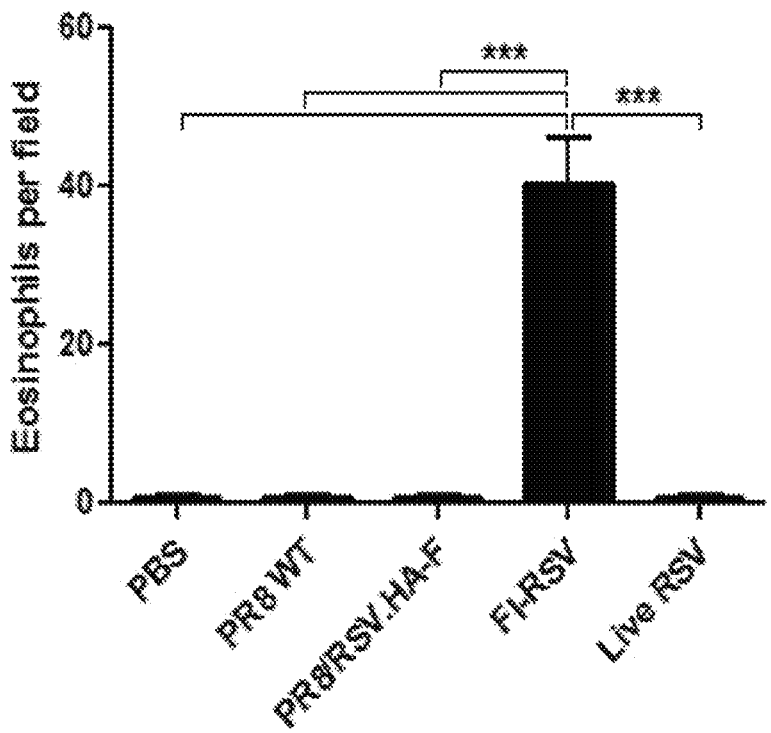

To estimate the degree of lung eosinophilia, H&CR-stained eosinophils were examined in the lung sections (lower row, FIG. 7A). The accumulation of H&CR positive eosinophils was significantly high in lungs of FI-RSV immunized-mice but was not observed in the lung tissue sections from mice that were vaccinated with the recombinant PR8/RSV.HA-F or control PR8 WT or live RSV (p<0.001, FIG. 7C).

Example 2: Recombinant Influenza Virus (PR8/RSV.HA-G) Carrying the Chimeric Constructs of Hemagglutinin (HA) and Central Conserved-Domains of the RSV G Protein Materials and Methods
Cells and Viruses 293T cells (DuBridge, R. B., et al., 1987. Mol Cell Biol 7, 379-387) and HEp2 cells (Quan, F. S., et al., 2011. J Infect Dis 204, 987-995) were obtained from ATCC and maintained in DMEM media. The RSV strain A2 was obtained. Influenza virus A/PR/8/1934 (H1N1, abbreviated as PR8) was grown in 10-day-old embryonated hen's eggs at 37° C. for 2 days. The allantoic fluid was harvested and stored at −70° C. until used. The viruses were inactivated by mixing the virus with formalin at a final concentration of 1:4000 (v/v) as described previously (Quan, F. S., et al., 2008. Journal of virology 82, 1350-1359). The viruses were purified by using discontinuous sucrose gradient ultracentrifugation with layers of 20 and 60% (wt/vol) as previously described (Song, J. M., et al., 2011. PLoS One 6, e14538).

Construction of PR8/RSV.HA-G1 and PR8/RSV.HA-G2

Recombinant viruses were rescued using the pHW2000-based eight-plasmid system as described (Hoffmann, E., et al., 2000. Proc Natl Acad Sci USA 97, 6108-6113). The sequence encoding RSV G protein aa131-230 was inserted between the 3' end of the HA signal peptide sequence and the nucleotide sequences encoding the N-terminal domain of the HA1 ectodomain of pHW2000-HA plasmid as described (Li, Z. N., et al., 2005. J Virol 79, 10003-10012). The inserted sequence was followed by a GGGGS (SEQ ID NO:13) or AAAPGAA (SEQ ID NO:12) peptide linker to facilitate the proper folding of the inserted polypeptides as independent domains, respectively (FIG. 9A).

Figure 9A:
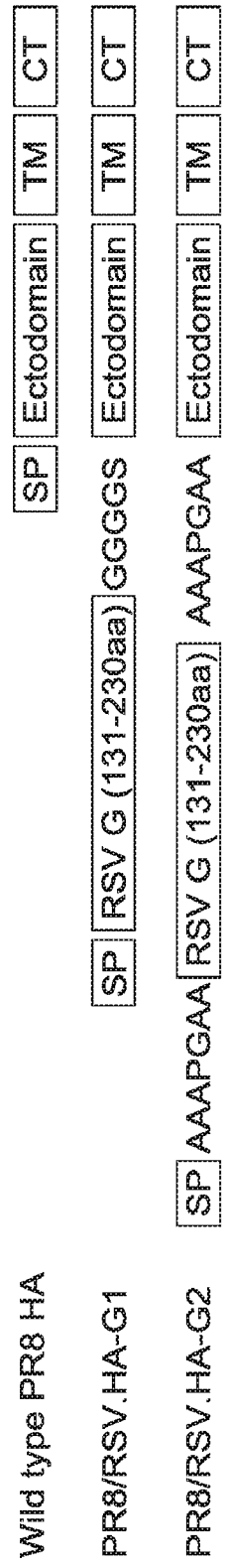

To generate recombinant viruses PR8/RSV.HA-G1 and PR8/RSV.HA-G2, 293T cells were cotransfected with eight pHW2000 plasmids of influenza virus gene segments including the chimeric HA-G constructs (FIG. 9A). After 48 h, the medium was collected and inoculated to embryonated chicken eggs. After 72 h, the presence of the rescued recombinant viruses in the allantoic fluids was confirmed by hemagglutination of chicken red blood cells. Purified viruses (2×10$^8$ PFU/ml) were prepared by discontinuous sucrose gradient ultracentrifugation of each crude stock (2×10$^6$ PFU/ml) and then by resuspending in PBS to have the same PFU amount of virus. To determine the incorporation of recombinant HA-G proteins, the reactivity to RSV specific monoclonal antibody 131-2G was analyzed using equal amounts of virus.

Immunizations and RSV Challenge of Mice

For animal experiments, 6- to 8-week-old female BALB/c mice (n=5; Harlan Laboratories) were intranasally inoculated with phosphate-buffered saline (PBS) or 500 EID$_{50}$ dose (50% egg infective dose, EID$_{50}$) of PR8/RSV.HA-G1, PR8/RSV.HA-G2, or PR8 wild-type (PR8 WT) or 2×10$^5$ PFU of RSV A2 strain under isoflurane anesthesia. The FI-RSV control group (n=5) was intramuscularly immunized with 50 μl of FI-RSV (2 μg) adsorbed to aluminium hydroxide adjuvant (2 mg/ml) (Prince, G. A., et al., 2001. The Journal of general virology 82, 2881-2888). Blood samples were collected at 7 weeks after immunization. All immunized mice were challenged with RSV A2 strain (2×10$^5$ PFU) at 8 weeks after immunization. The individual lungs, spleens, and bronchoalveolar lavage fluid (BALF) samples were removed aseptically at day 5 post-challenge (p.c.), and lung homogenates were prepared as described (Kwon, Y. M., et al., 2014. Antiviral Res 104, 1-6). All animal experiments presented in this study were approved by the Georgia State University IACUC review boards (IACUC A11026).

Assays for Antibody Responses and Virus Titration

RSV G protein-specific antibodies (IgG, IgG1, and IgG2a) were determined in samples by enzyme-linked immunosorbent assay (ELISA) as previously described (Kim, S., et al., 2012. PLoS One 7, e32226). Briefly, the extracellular domain of RSVG protein with over 95% purity (200 ng/ml, Sino biological, Beijing, China) or inactivated influenza virus (4 µg/ml) was used as a coating antigen. The wells were washed with PBS containing 0.05% Tween 20 (PBST) and blocked with PBST containing 3% BSA for 2 h at 37° C. Serially diluted serum samples were added and incubated for 1.5 h at 37° C. then horseradish peroxidase (HRP)-conjugated goat anti-mouse IgG, IgG1, and IgG2a (Southern Biotechnology) were used as secondary antibodies. The tetramethybenzidine (TMB) peroxidase substrate (Sigma-Aldrich, St. Louis, Mo.) was used to develop color and optical density was read at 450 nm. RSV-specific neutralizing antibody titers in mouse sera were measured by a slightly modified version of a standard method as described previously (Anderson, L. J., et al., 1988. J Virol 62, 4232-4238). Briefly, mouse sera were heat-inactivated at 56° C. for 45 min and serially diluted two-fold in growth medium. Equal volumes of diluted sera were mixed with RSV A2 to yield 300 PFU/well. RSV with or without immune serum mixture was incubated at 33° C., 5% $CO_2$ for 1 h before incubation in the HEp2 monolayers. The next steps were followed by an immunoplaque assay procedure as described (Quan, F. S., et al., 2011. J Infect Dis 204, 987-995). After fixing with ice-cold acetone-methanol and air drying, individual plaques were visualized using anti-RSV F monoclonal antibody (131-2A, Millipore), HRP conjugated anti-mouse IgG antibody, and 3,3'-diaminobenzidine tetrahydrochloride substrate (Invitrogen).

Analysis of Cytokines

Cytokine levels in BALF were determined using ELISA kits for IL-5 (eBioscience) and eotaxin (R&D Systems, Minneapolis, Minn.) according to the manufacturers' instructions in duplicate against a standard curve.

Flow Cytometric Analysis

For analyzing phenotypes of cell population, BAL cells were collected and then stained with fluorochrome-conjugated antibodies (anti-CD3, CD45, CD11b, CD11c, and SiglecF antibodies) as described (Lee, J. S., et al., 2014. J Interferon Cytokine Res). The lung tissues were homogenized and cells were then passed through strainer and spun on 44 and 67% Percoll gradients at 2800 rpm for 20 min. A band of cells was harvested and washed with PBS. To determine intracellular cytokine production, lung cells were stimulated with 5 µg/ml of peptides corresponding to the CD4 T cell epitope $G_{183-195}$ peptide (WAICKRIPNKKPG, SEQ ID NO:14) and the CD8 T cell epitope $F_{85-93}$ peptide (KYKNAVTEL, SEQ ID NO:15) with Brefeldin A (BFA) (20 µg/ml) at 37° C. for 5 h and then stimulated lung cells were surface stained for anti-CD45-peridinin chlorophyll protein complex, anti-CD4-allophycocyanin (APC) and anti-CD8α-r-phycoerythrin (PE) antibodies and then were permeable using the Cytofix/Cytoperm kit (BD Biosciences). Intracellular cytokines were revealed by staining the cells with or anti-IL-4-fluorescein isothiocyanate or anti-IFN-γ-APC-Cy7 antibodies. All antibodies were purchased from eBiosciences or BD Bioscience. Stained BAL and lung cells were analyzed using LSRFortessa (BD Biosciences) and FlowJo software (Tree Star Inc.).

Lung Histology of RSV-Infected Mice

For histological analysis, lung samples were fixed in 10% neutral buffered formalin for 48 hrs, transferred to 70% ethanol, embedded paraffin blocks, sectioned into a thickness of 5 µm and stained with hematoxylin and eosin (H&E), periodic acid-Schiff stain (PAS) or hematoxylin and congo red (H&CR) (Meyerholz, D. K., et al., 2009. Toxicologic pathology 37, 249-255). At least eight sections per mouse were obtained for histopathologic analysis.

Statistical Analysis

All results are expressed as the mean±standard error of the mean (SEM). Significant differences among treatments were evaluated by 1-way or 2-way ANOVA where appropriate. P-values of less than or equal to 0.05 were considered statistically significant.

Results

Figure 9B:
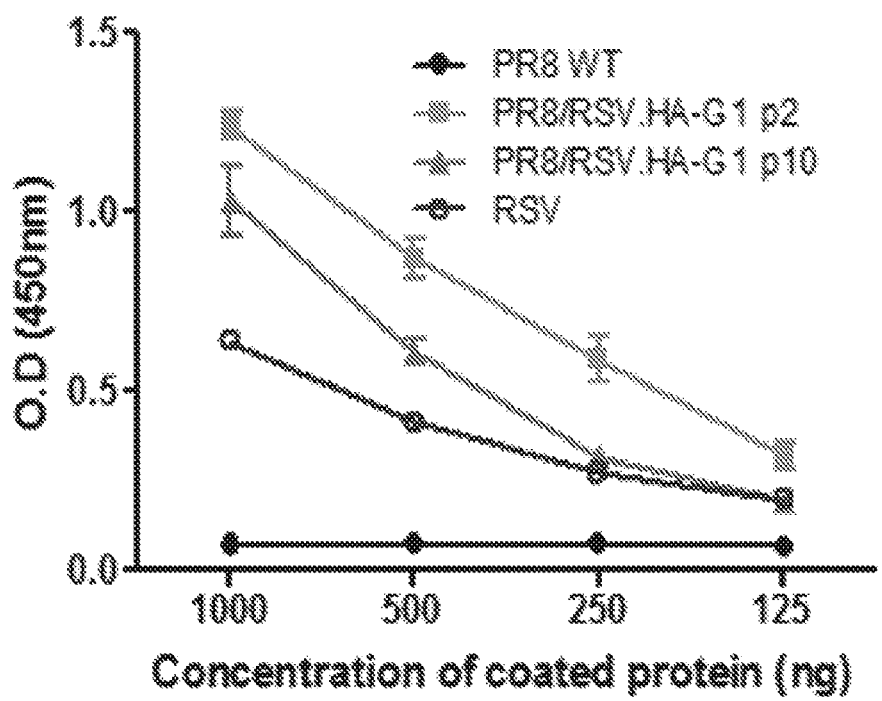
Figure 9C:
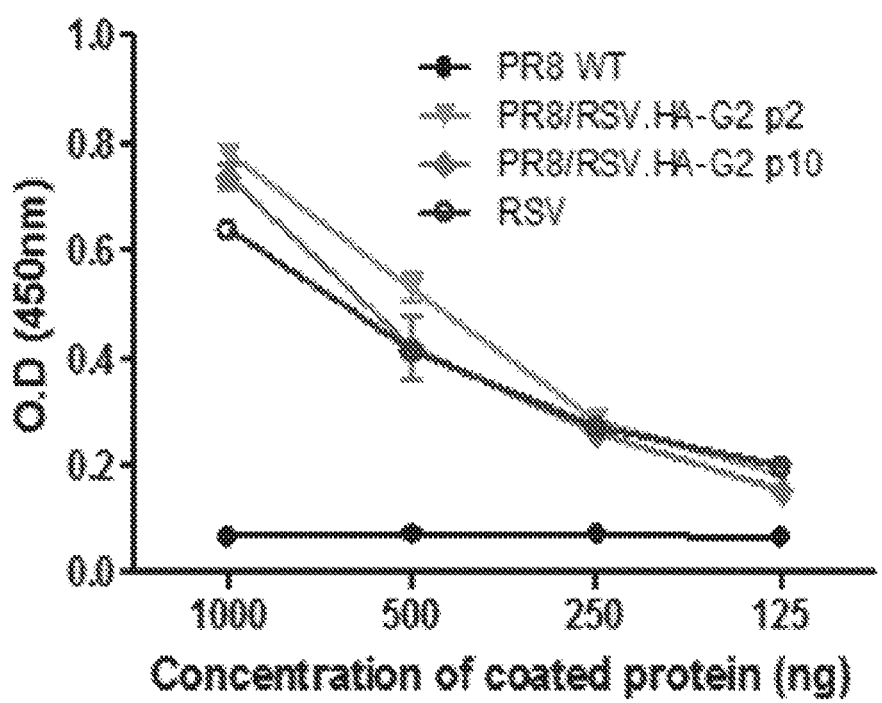

Generation of Recombinant Influenza Virus Containing an RSV G Protein Conserved-Domain As a proof-of-concept study to explore whether a recombinant influenza virus carrying an RSV G conserved-central domain could provide protection against RSV, the PR8 influenza virus reverse genetics system was used. Two chimeric recombinant PR8/RSV viruses were generated, each containing the RSV G conserved-domain (aa131-230) but with different linkers (PR8/RSV.HA-G1 with a GGGGS (SEQ ID NO:13) linker, PR8/RSV.HA-G2 with AAAPGAA (SEQ ID NO:12) linkers at both conjugate sites, FIG. 9). For quantitative determination of G domain expression on recombinant influenza/RSV viruses, PR8/RSV.HA-G1, -G2, parental PR8 WT, and RSV were compared for its reactivity to G protein-specific monoclonal antibody 131-2G by ELISA (FIGS. 1B and 1C). PR8/RSV.HA-G1 with a shorter linker was found to have 4-fold higher reactivity to 131-2G antibody than RSV. The reactivity of 131-2G antibody to PR8/RSV.HA-G2 was similar to that of RSV. These results suggest that recombinant influenza/RSV viruses contain RSV G domains at higher or similar levels compared to those in WT RSV, which is important. In addition, the stability of the G domain expression in the PR8/RSV.HA-G viruses was ascertained by serially passaging the virus in eggs (FIGS. 9B and 9C). The reactivity of 131-2G antibody to PR8/RSV.HA-G viruses slightly decreased after 10 serial passages probably due to a fraction of virus that might not express a conjugate HA-G but the reactivity for RSV G domain contents was still higher than RSV.

Recombinant PR8/RSV.HA-G Viruses Show Attenuated Phenotypes

Figures 10A, 10B:
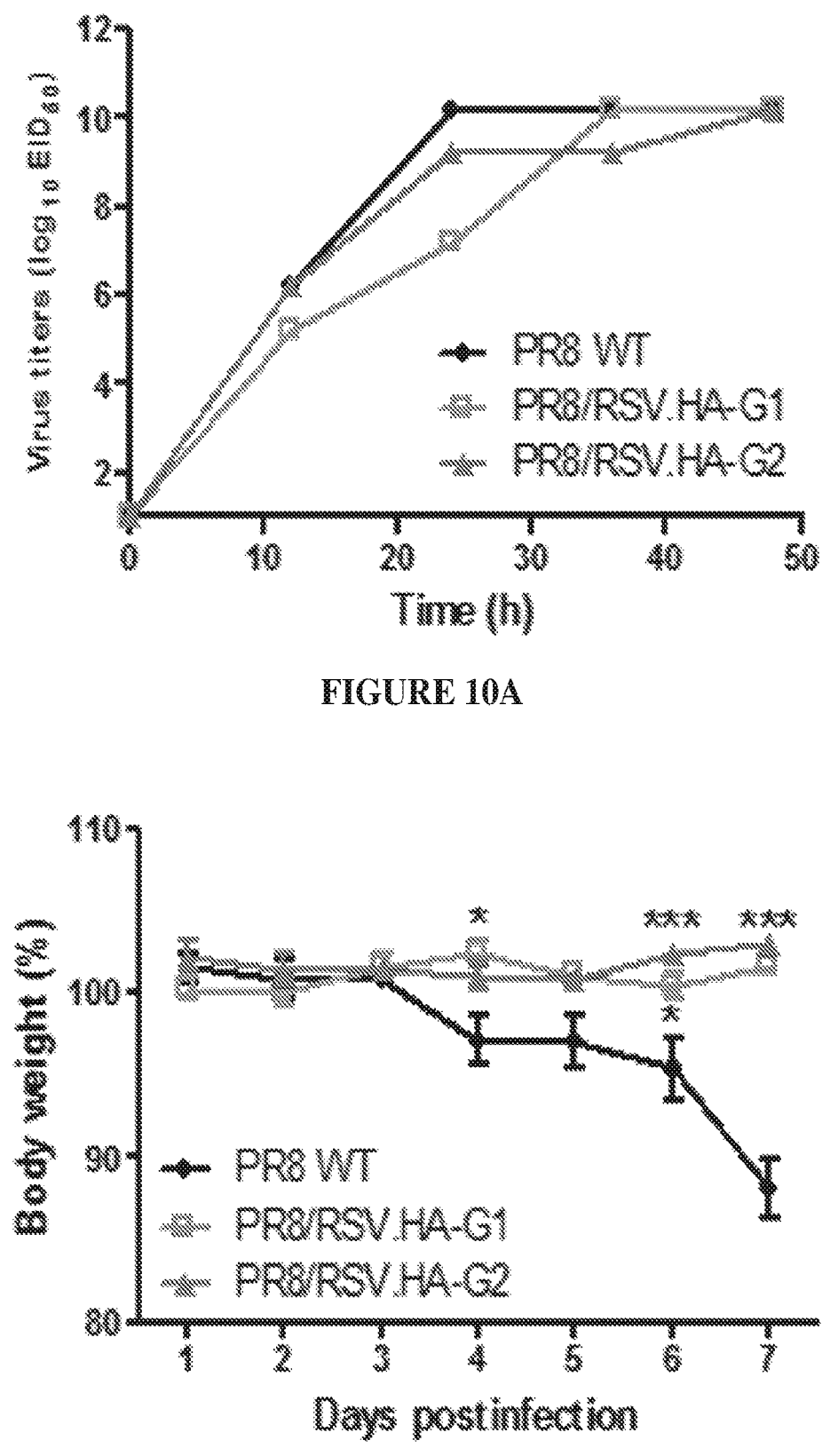

To determine in vitro viral growth kinetics, eggs were infected at a 15 $EID_{50}$ (50% egg infective dose) of PR8 WT, PR8/RSV.HA-G1 or PR8/RSV.HA-G2. At various times after infection, viral titers in allantoic fluids were quantified by $EID_{50}$ assay (FIG. 10A). The growth kinetics of PR8/RSV.HA-G1 or PR8/RSV.HA-G2 in eggs was found to be comparable to that of PR8 WT.

To compare replication and pathogenicity of PR8/RS-V.HA-G and PR8 WT viruses, BALB/c mice were infected with 1,000 $EID_{50}$ of each virus. Mice infected with PR8 WT virus showed a progressive weight loss over 12% from day 4 to day 7 post-infection. In contrast, mice inoculated with PR8/RSV.HA-G viruses did not display weight losses (FIG. 10B). The recombinant viral vaccine-inoculated mice showed significantly lower lung viral titers compared with those in PR8 WT-inoculated mice (p<0.001, FIG. 10C). Despite similar growth kinetics in eggs, the recombinant PR8/RSV.HA-G viruses were attenuated in terms of viral replication and did not cause weight losses in mice compared to PR8 WT.

Inoculation with PR8/RSV.HA-G Viruses Induces RSV G Specific Antibody

Figures 10C, 11A:
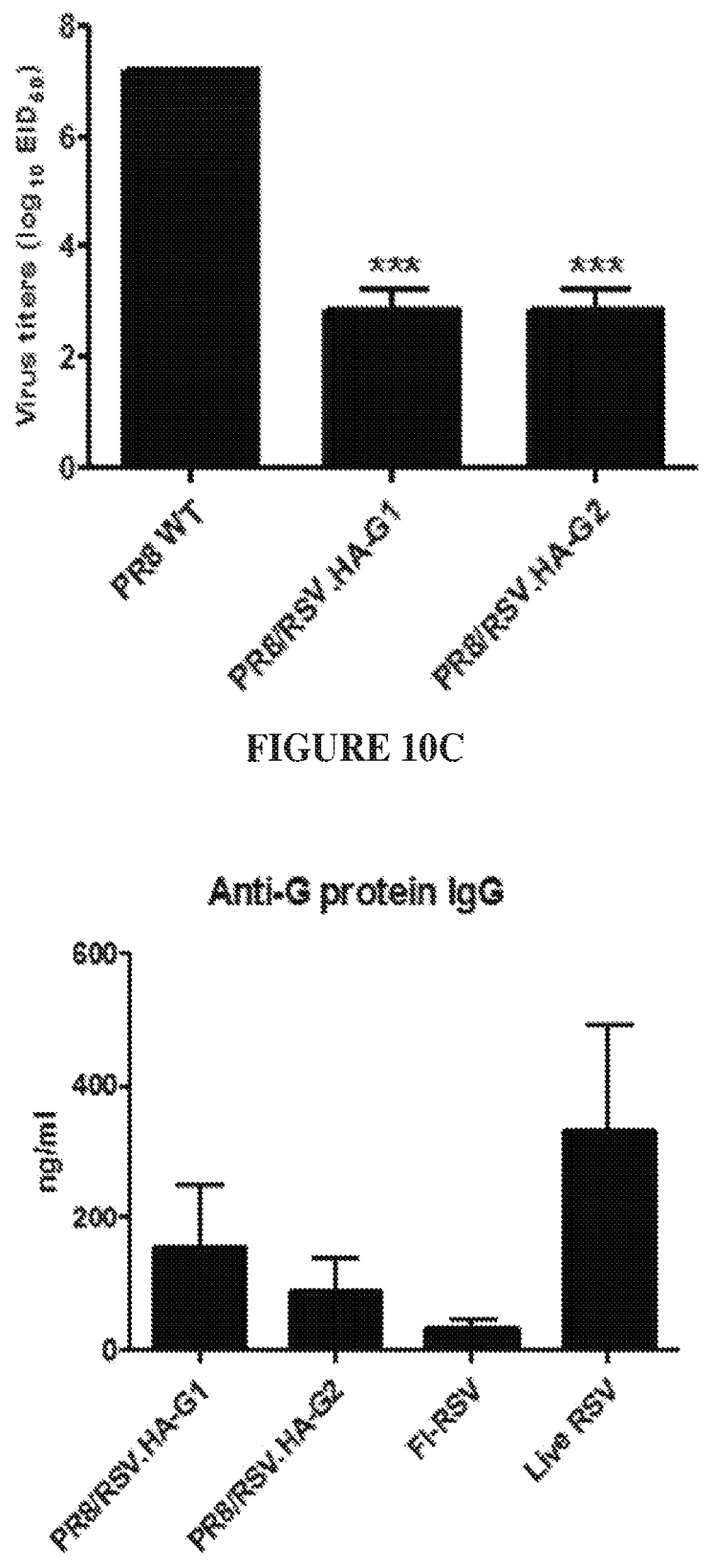
Figure 11B:
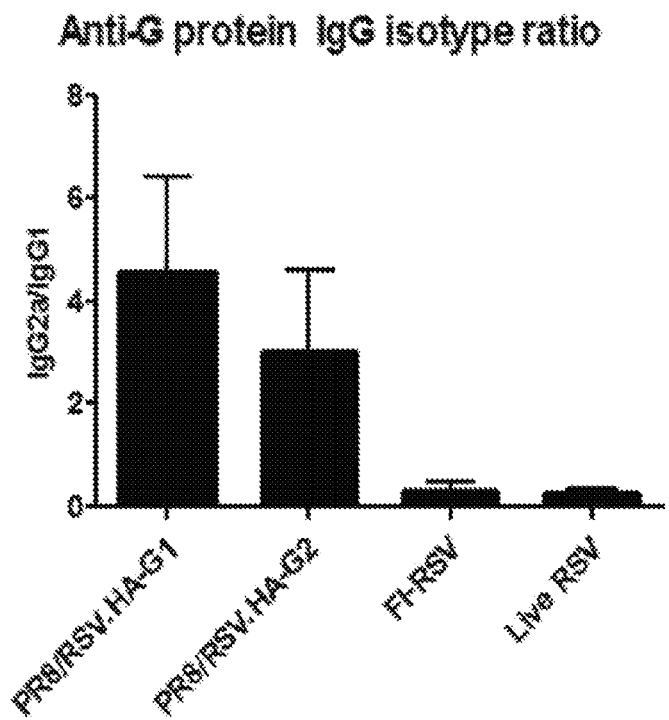
Figure 11C:
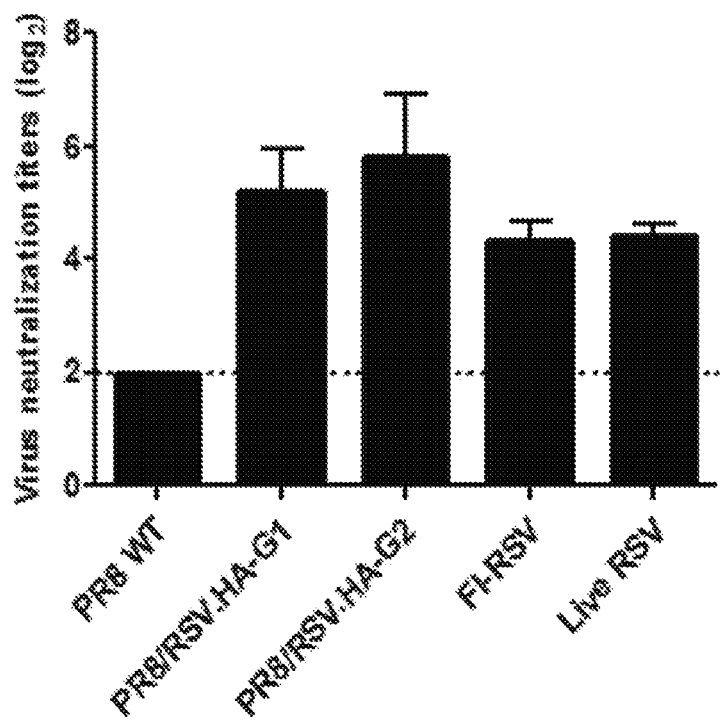
Figure 11D:
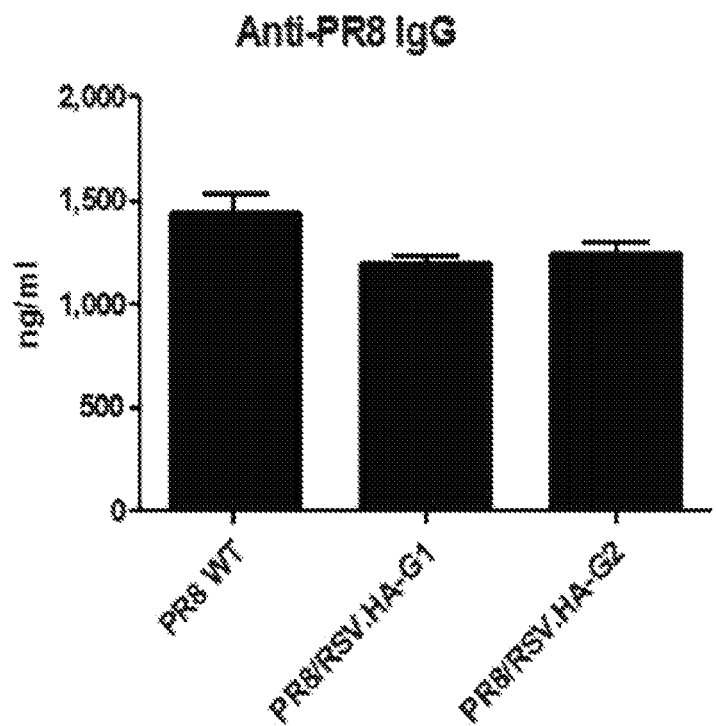

BALB/c mice received a single intranasal administration with PR8/RSV.HA-G1, PR8/RSV.HA-G2, or PR8 WT at 500 $EID_{50}$ dose. Seven weeks after immunization, serum antibody titers were measured (FIG. 11). RSV G-specific IgG antibodies were detected at high levels in the live RSV group (331.3±158.5 ng/ml). RSV G-specific IgG antibody concentrations in the PR8/RSV.HA-G1 (155.6±95.4 ng/ml) and the PR8/RSV.HA-G2 group (90.4±48.9 ng/ml) were approximately 4.6- and 2.5-fold higher than those in the FI-RSV group (33.8±11.6 ng/ml) (FIG. 11A). Moreover, the PR8/RSV.HA-G1 and PR8/RSV.HA-G2 groups showed higher ratios of IgG2a/IgG1 isotype antibodies than the FI-RSV and live RSV group (FIG. 11B). The PR8/RSV.HA-G1 and PR8/RSV.HA-G2 groups showed RSV neutralizing antibody titers of 5.2±0.73 $\log_2$ and 5.8±1.11 $\log_2$, respectively. The FI-RSV and live RSV group showed lower RSV neutralizing titers of 4.3±0.3 and 4.4±0.2 $\log_2$, respectively (FIG. 11C), but there were no significant differences among the groups. Due to the insertion of a partial domain (aa131-230) of RSV G protein to recombinant viruses, RSV G-specific IgG antibody concentrations in the PR8/RSV.HA-G groups could be lower than those in the live RSV group. Nonetheless, small amount of conserved domain-specific antibody from the PR8/RSV.HA-G groups seem to be enough to neutralize RSV comparable to live RSV. All mice immunized with recombinant or PR8 WT virus showed similar levels of PR8 virus specific-IgG antibodies (FIG. 11D). These results provide evidence that recombinant influenza/RSV viruses are able to raise RSV neutralizing antibody responses.

Recombinant PR8/RSV.HA-G Virus Confers Protection Against RSV Infection

Figure 12A:
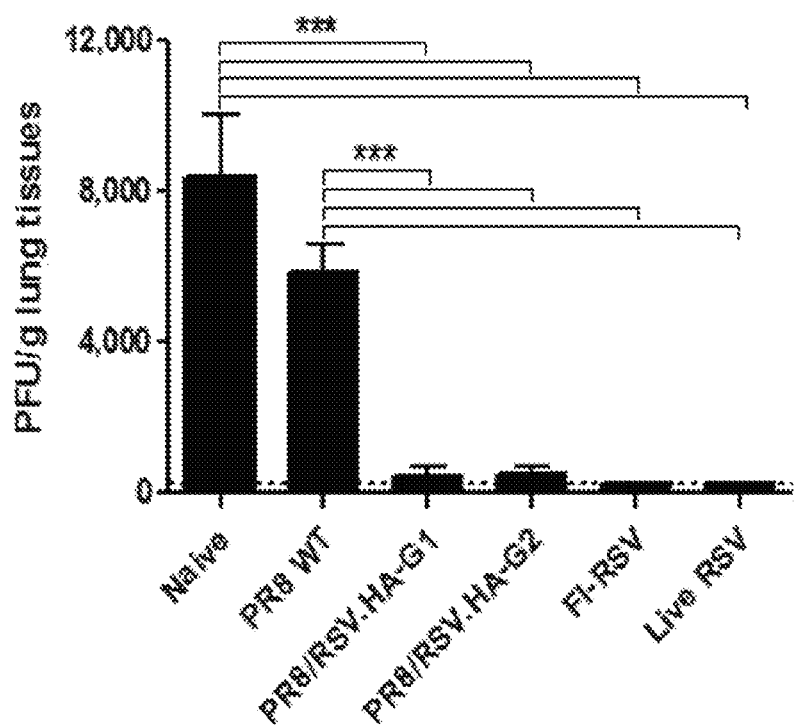

To assess the protective efficacy of recombinant influenza/RSV vaccines, groups of mice were challenged with RSV A2 ($2 \times 10^5$ PFU/mouse) at 8 weeks after immunization. PBS-immunized mice showed moderate weight loss (~4%) after RSV challenge. By contrast, weight loss was not observed with PR8/RSV.HA-G1, PR8/RSV.HA-G2, FI-RSV, or live RSV-immunized mice, improving clinical outcomes after RSV challenge. Clearance of lung viral loads is an important parameter in assessing the efficacy of protection against RSV infection. Lung tissues were collected from individual mice at day 5 p.c. and viral titers in lung samples were determined using an immunoplaque assay. The highest RSV titer was detected in PBS-immunized mice. FI-RSV, live RSV and recombinant PR8/RSV.HA-G-inoculated mice showed significantly lower lung RSV titers compared with those in PBS-immunized mice (p<0.001, FIG. 12A).

Figure 12B:
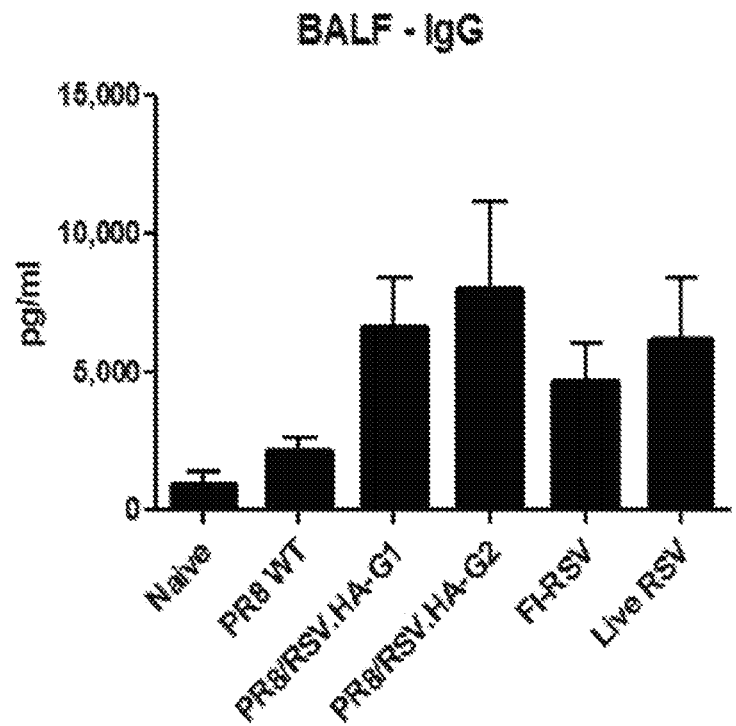
Figure 12C:
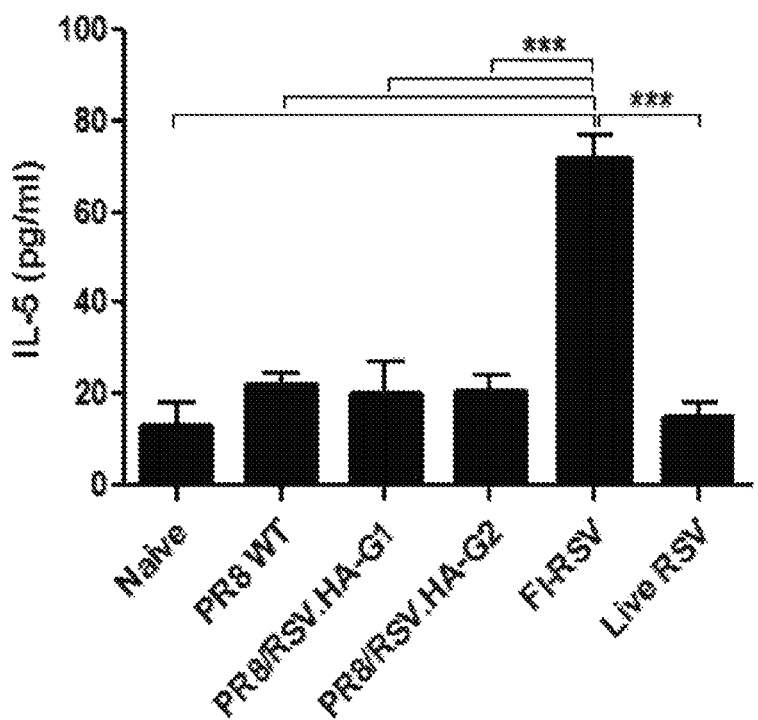
Figure 12D:
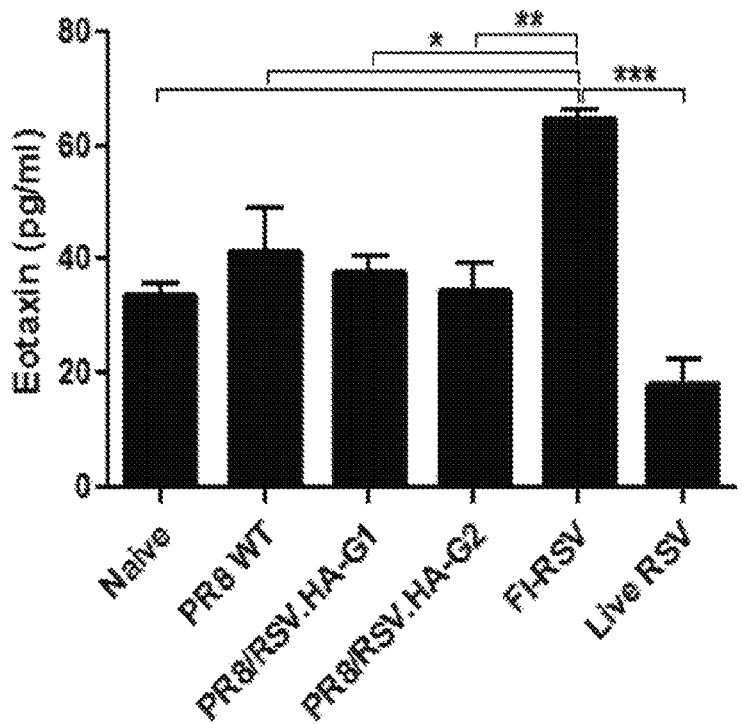

To better understand mechanism of protection by recombinant viral RSV vaccines, RSV G-specific antibody and immune responses in BALF were determined at an early time post challenge. BALF samples from the groups of mice that were immunized with PR8/RSV.HA-G1 and PR8/RSV.HA-G2 showed higher levels of RSV G-specific IgG concentrations than those from PBS, PR8 WT, FI-RSV, and live RSV-immunized mice at day 5 p.c. (FIG. 12B). The levels of IL-5 (FIG. 12C) and eotaxin (FIG. 12D) in mice immunized with FI-RSV were significantly higher than those in the other groups.

Figure 13A:
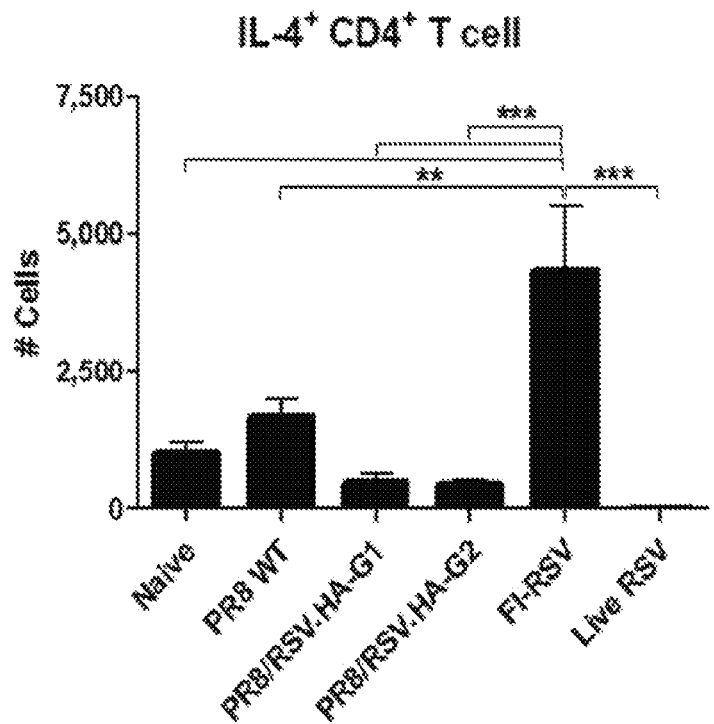
Figure 13B:
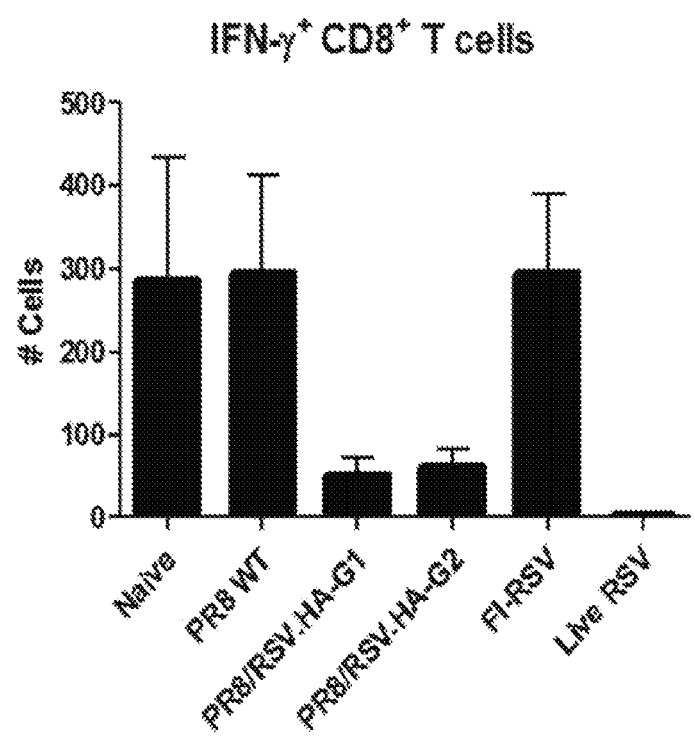

To determine T cell responses, IFN-γ or IL-4 cytokine-producing lung cells were measured after in vitro stimulation with $G_{183-195}$ and $F_{85-93}$ peptide (FIG. 13). FI-RSV immune mice showed the highest levels of IL-4-producing $G_{183-195}$-specific $CD4^+$ T cells whereas the PR8/RSV.HA-G1 and PR8/RSV.HA-G2 groups did not induce RSV specific CD4 T cell responses (FIG. 13A). IFN-γ-producing $G_{183-195}$-specific $CD4^+$ T cells were not significantly induced in the recombinant PR8/RSV vaccine groups compared with the FI-RSV or PR8 WT group (p<0.001, FIG. 13B). Also, IFN-γ producing $F_{85-93}$-specific $CD8^+$ T cells were not induced in the PR8/RSV.HA-G1 and PR8/RSV.HA-G2 groups. Previously, it was reported that IFN-γ-producing F-specific $CD8^+$ T cells were induced in the lungs from RSV-infected naive mice (sDe Baets, S., et al., 2013. J Virol 87, 3314-3323; Garg, R., et al., 2014. J Gen Virol 95, 1043-1054; Johnson, J. E., et al., 2013. Immunol Lett 150, 134-144). Concordantly, the PBS, FI-RSV, and PR8 WT groups showed low levels of IFN-γ producing $F_{85-93}$-specific $CD8^+$ T cells (FIG. 13B) with variations compared to $IL4^+$ $CD4^+$ T cells. IL-4- or IFN-γ-producing T cells were not detected at a significant level in the live RSV group (FIG. 13). It is speculated that no induction of RSV-specific T cells may be due to the complete control of lung viral loads in this live RSV group.

PR8/RSV.HA-G Virus does not Cause Pulmonary Inflammation Upon RSV Infection

Figure 14A:
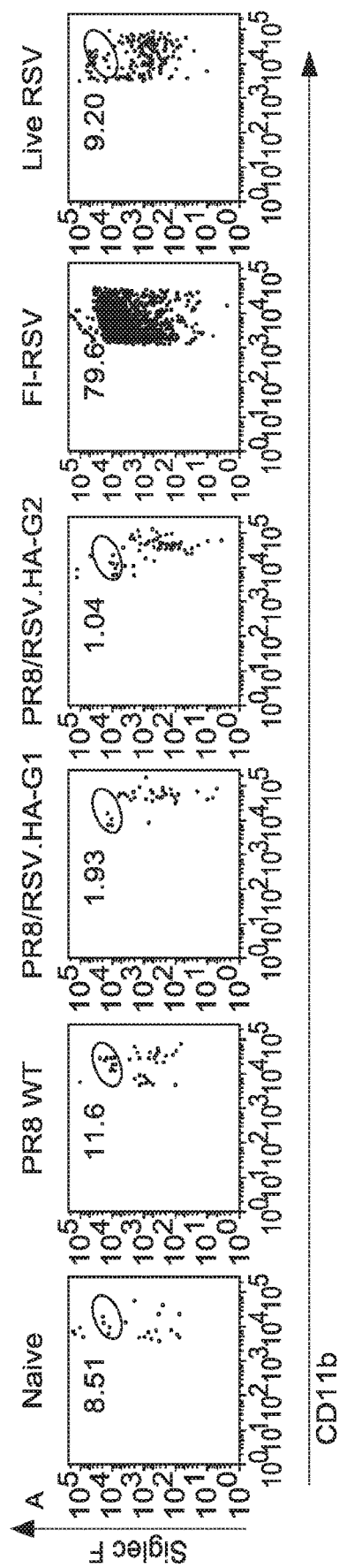
FIGS. 14A to 14C show PR8/RSV.HA-G1 and PR8/RSV.HA-G2 viruses do not induce eosinophil infiltration upon RSV challenge. Cells in BALF samples collected at 5 day p.c. were stained with anti-CD45, CD11b, CD11c, and Siglec-F antibodies. (A) Representative dot plots of CD11b+ SiglecF+ cells (eosinophils). Number in the dot plots indicates percentages among CD45+CD11c-granulocytes. (B) The mean percentage data are presented as mean±SEM. (C) Total BAL cell counts were determined. Data represent mean±SEM. Statistically significance was determined by 1-way ANOVA. Asterisks indicate significant differences (*p<0.05, p<0.01, and *p<0.001) compared with the results in the FI-RSV group.
Figure 14B:
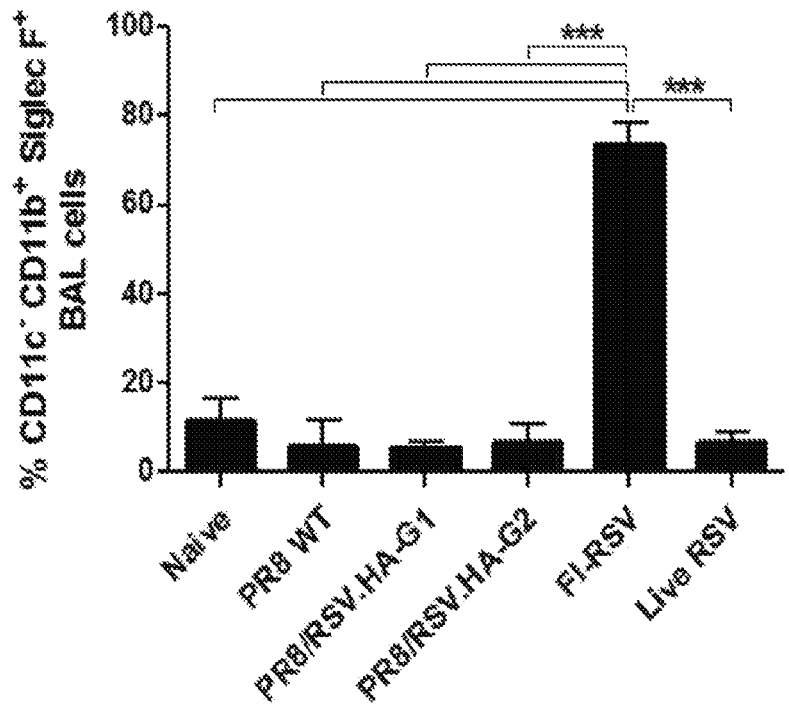
Figure 14C:
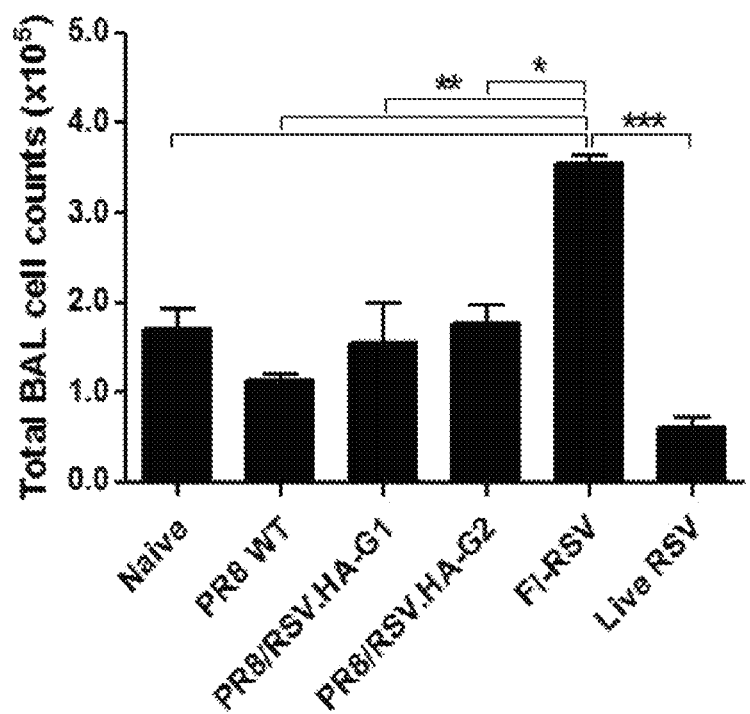

Eosinophils with the phenotypes of $CD45^+CD11c^-CD11b^+$ Siglecr are known to be enriched in inflamed lung tissues (Stevens, W. W., et al., 2007. J Immunol Methods 327, 63-74). At day 5 p.c., the FI-RSV group prominently induced a population with $CD45^+CD11c^-CD11b^+SiglecF^+$ cells (FIG. 14A), which was approximately 73% out of the $CD45^+CD11c^-$ granulocyte populations (FIG. 14B). Importantly, the group of mice immunized with PR8/RSV.HA-G1, PR8/RSV.HA-G2, PR8 WT, and live RSV did not show such a distinct population of $CD11b^+SiglecF^+$ cells (FIGS. 14A and 14B). Moreover, there was significantly higher cellularity of infiltrating cells in BAL fluids from mice in the FI-RSV group compared to those from other groups (FIG. 14C).

Figure 15A:
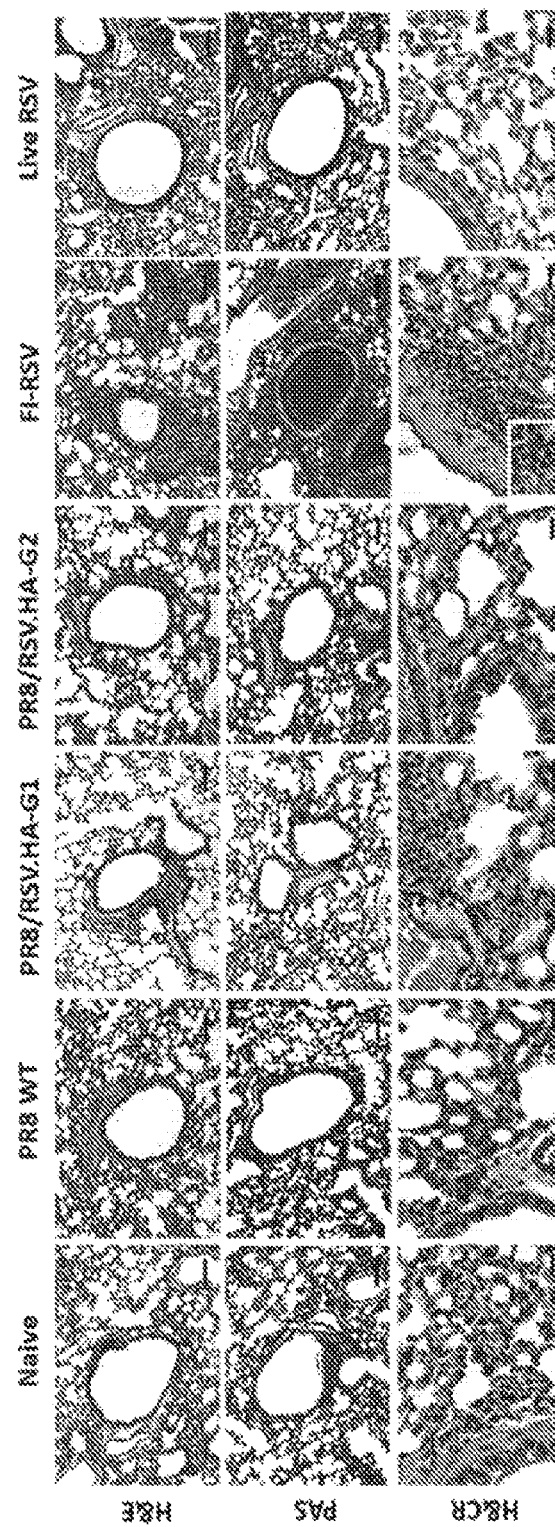

Examination of pulmonary histopathology is important in assessing the safety of RSV vaccine candidates. Lung tissue sections in each group of mice were examined for inflammation at day 5 p.c. (FIG. 15). FI-RSV-immunized mice displayed a massive influx of inflammatory cells around pulmonary airways and thickened alveolar layers, presenting heavily inflamed lung tissues. In contrast, lung tissues from mice immunized with PR8/RSV.HA-G1, PR8/RSV.HA-G2, or live RSV did not show an obvious sign of inflammation (FIG. 15A). Alveolar epithelium appeared to be normal in lung tissue histology from recombinant influenza/RSV or live RSV-immunized mice. PBS or PR8 WT control mice infected with RSV showed a slight level of interstitial pneumonia as indicated by infiltrates of inflammatory cells and thickened alveolar layers in the H&E staining of lung tissue sections.

Figures 15B, 15C:
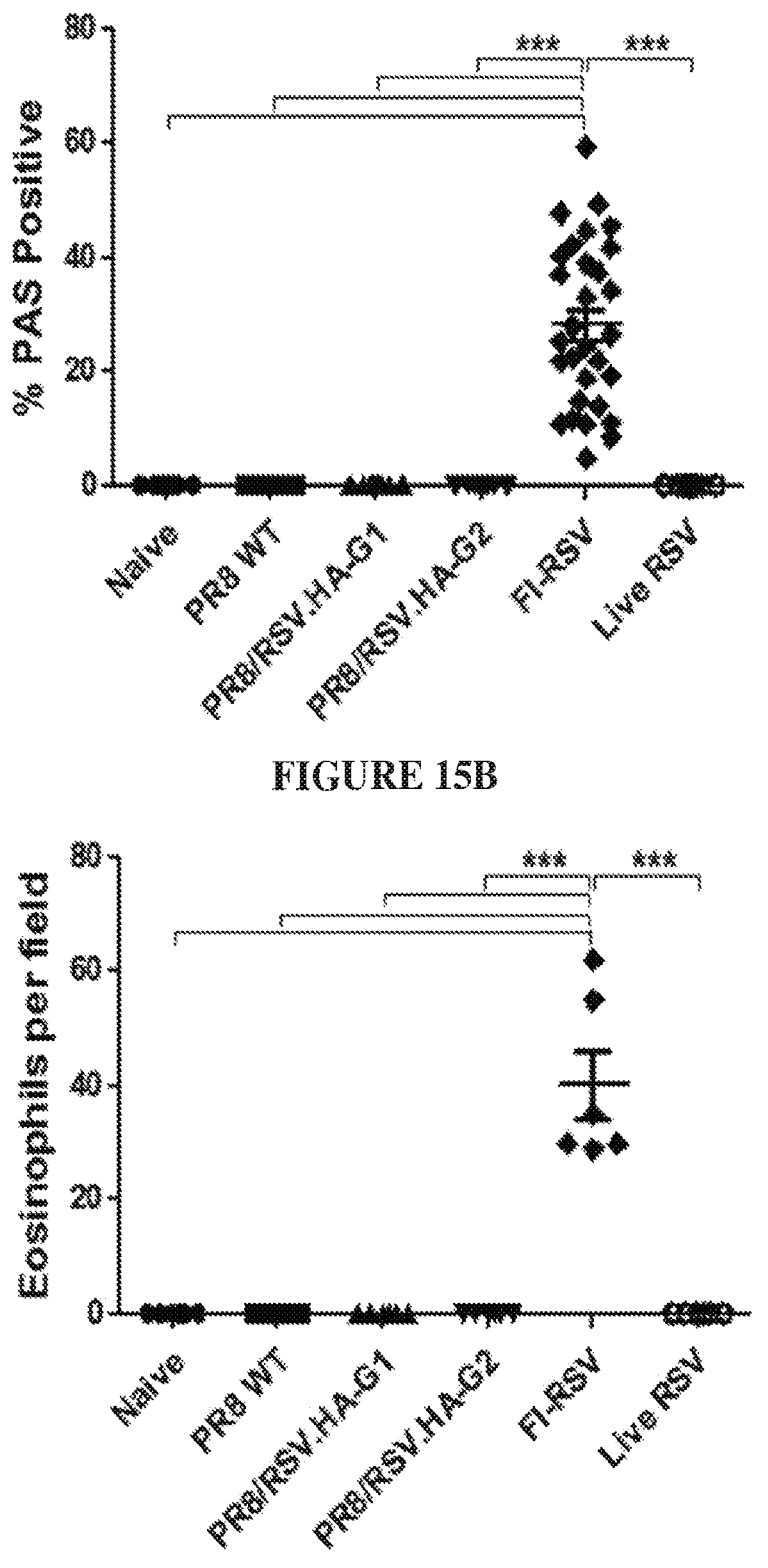

Lung sections were stained with PAS to visualize mucus production. Representative PAS-stained sections of lungs from the mice are shown in the middle row of FIG. 6A. These sections were scored for percentages of airway linings showing PAS staining (FIG. 15B). The recombinant influenza/RSV immunized-mice showed significantly less PAS staining than the FI-RSV-immunized mice (p<0.001). To estimate the degree of lung eosinophilia, H&CR stained lung sections were examined (bottom row, FIG. 15C). The accumulation of H&CR positive eosinophils was significantly greater in lungs of FI-RSV immunized-mice than in those of animals that were vaccinated with recombinant influenza/RSV.HA-G, PR8 WT or live RSV (p<0.001).

Example 3: Recombinant Influenza Viruses Carrying M2 Extracellular Domains in a Chimeric Hemagglutinin Conjugate are Effective in Inducing Cross-Protective Antibody Responses Materials and Methods Cells and Viruses 293T cells were obtained from ATCC. The influenza A viruses, A/PR/8/34 (A/PR8, H1N1), A/California/04/09 (A/California, H1N1), A/Philippines/2/82 (A/Philippines, H3N2), A/Vietnam/1203/2004 (A/Vietnam, rgH5N1 with NA and 6 internal genes from A/PR8) (Song et al., 2011) and A/Mandarin Duck/Korea/PSC24-24/2010 (A/Mandarian duck, avian rgH5N1 containing HA with polybasic residues removed, NA and M genes from A/Mandarin Duck, and the remaining backbone genes from A/PR8 virus), were grown in 10-day-old chicken eggs at 37° C. for 2 days. The viruses were inactivated using formalin (Quan et al., 2008. J Virol 82, 1350-1359).

Generation of Recombinant Virus

Replication competent recombinant viruses (rg/M2e4x-HA) were rescued using the pHW2000-based eight-plasmid system described by Hoffmann et al. (Hoffmann et al., 2000. Proc Natl Acad Sci USA 97, 6108-6113). In brief, the sequence encoding 4x tandem repeat of heterologous M2e sequences derived from human, swine, and avian influenza viruses (FIG. 16A) was designed and synthesized (Genscript) to be inserted between the HA signal peptide sequence and N-terminal domain of the HA' ectodomain (M2e4x-HA) of wild-type A/PR8 virus (FIG. 16A). A M2e4x-HA gene fragment was inserted into pHW2000 plasmid. To generate recombinant virus, 293T cells were co-transfected with a chimeric M2e4x-HA pHW2000 plasmid and seven other pHW2000 plasmids containing A/PR8 virus backbone genes. After 48 hours, the supernatant was inoculated into 10-day-old chicken eggs. After 72 hours, the presence of the virus was confirmed by a hemagglutination assay.

Characterization and Pathogenicity of Recombinant Viruses

Rescued recombinant viruses were exposed to multiple passages from 2 to 10 times and the passaged recombinant viruses (passage #2, #6, and #10) were characterized. Influenza A virus M2 monoclonal antibody (14C2, Abcam Inc., Cambridge, Mass.) or HA specific monoclonal antibody (IC5-4F8, BEI) was used for detection of HA or M2e protein by western blot or ELISA. To assess viral growth kinetics, chicken eggs were infected with 15 times of 50% egg infectious dose ($EID_{50}$) of recombinant (rg/M2e4x-HA) or wild-type influenza viruses and incubated to 48 hours. The allantoic fluids were harvested every 12 hour, and virus titers were assayed as $EID_{50}$/ml.

To verify pathogenicity of recombinant viruses comparing to wild-type virus, 6-8-week-old female BALB/c mice (N=6 or 3, respectively; Harlan Laboratories) were intranasally inoculated with 2,000 or 4,000 $EID_{50}$ of recombinant or wild-type viruses. At day 7, lung samples were collected from three mice of each group to titer viruses. Lung extracts were prepared and the viral titers were determined (Kim et al., 2013. Antiviral Res 99, 328-335).

Immunogold Electron Microscopy of Purified Recombinant M2e4x-HA Virus

Sucrose gradient purified wild-type A/PR8 and recombinant rg/M2e4x-HA viruses (1 µg) were adsorbed onto formvar/carbon-coated copper grids (Electron Microscopy Sciences, Fort Washington, Pa.). After 15 min incubation, 4 µg of primary M2e monoclonal antibody (14C2, Abcam) was applied to grid for 1 h at room temperature. Following washing with 100 volumes of PBS, secondary 6 nm gold-conjugated anti-mouse antibody (Abcam) was added for 15 min at room temperature. The grids were then washed with 100 volumes of PBS, and negatively stained with 1.5% phosphotungstic acid (pH 7.0) for 30 sec. The images of stained wild type A/PR8 or recombinant M2e4x-HA viruses were captured using a JEOL JEM 2100 transmission electron microscope (TEM).

Immunizations of Mice

Six to eight-week-old female BALB/c mice (N=8; Harlan Laboratories) were intranasally inoculated with 500 $EID_{50}$ as prime, and 5,000 $EID_{50}$ of recombinant or wild-type viruses as boost 5 weeks later. Blood samples were collected at 4 weeks after each inoculation.

Antibody Responses and Hemagglutinin Inhibition (HAI) Assay

Virus-specific antibody responses were determined by ELISA using A/PR/8/1934 virus as a coating antigen (2 µg/ml) and M2e-specific antibody responses were determined using human, swine, and avian M2e-antigens as previously described (Quan et al., 2008. J Virol 82, 1350-1359). Hemagglutination inhibition (HAI) assay was determined against homologous and heterosubtypic influenza viruses as described (Kim et al., 2014. Molecular therapy: the journal of the American Society of Gene Therapy 22, 1364-1374; Quan et al., 2010. PLoS One 5, e9161).

Cross-Protective Efficacy Test of Immune Sera

To test cross-protective efficacy, immune sera were collected at 4 weeks after boost inoculation. In brief, sera were heat-inactivated at 56° C. for 30 min and the serum samples were mixed with the same volume of $2 \times LD_{50}$ of influenza viruses, A/California (pdmH1N1), A/Philippines (H3N2), A/Mandarian duck (avian rgH5N1) or A/Vietnam (rgH5N1), and incubated at room temperature for 1 hour. The mixture was intranasally administered to naive mice (N=3, BALB/c) and body weight and survival rates were daily monitored for 14 days.

Results

Figure 16D:
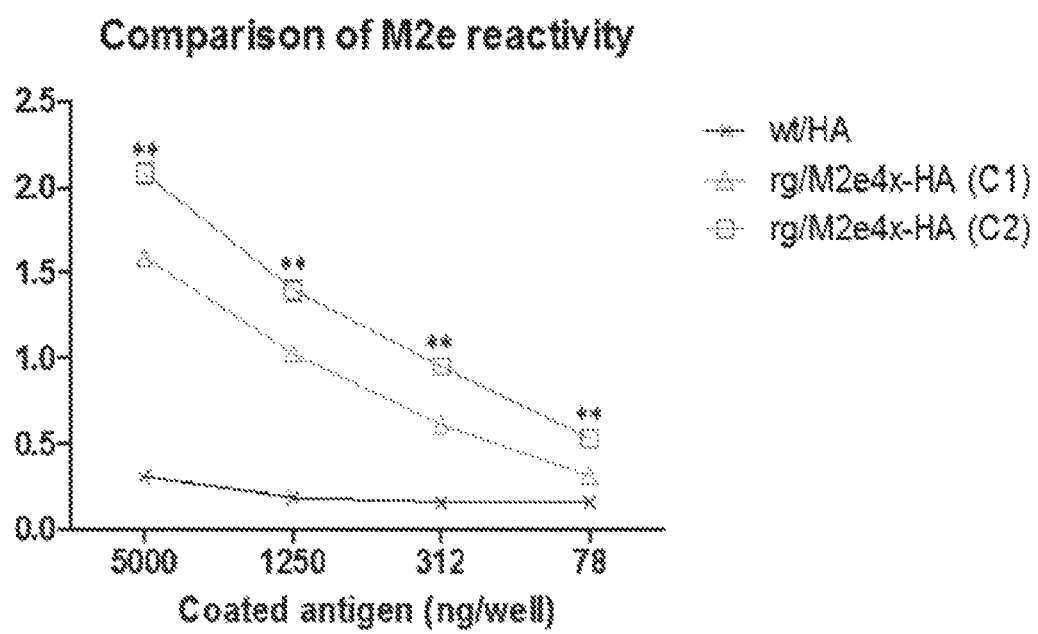

Replicable Recombinant Virus Carrying Chimeric M2e4x-HA Protein Expresses M2e Epitopes at High Levels In an attempt to overcome the strain-specific immune responses to HA, chimeric HA constructs (M2e4x-HA) containing a tandem repeat of heterologous M2e (M2e4x) at the N-terminus of HA were generated (FIG. 16A). The M2e4x is composed of human M2e (2x), swine M2e, and avian M2e (FIG. 16B). This tandem repeat M2e domain was conjugated to HA by either GGGGS or AAAPGAA connector, to facilitate the proper folding of the inserted polypeptides as independent domains (FIG. 16C). Using the reverse genetics system, replication-competent recombinant viruses could be recovered. Incorporation of M2e into recombinant virus was determined in comparison with wild-type A/PR8 virus by ELISA using M2e monoclonal antibody (FIG. 16D). The M2e epitope of wild-type virus was detected at a minimal level. In contrast, two recombinant viruses showed high reactivity to M2e monoclonal antibody and the reactivity of recombinant virus containing AAAPGAA (connector 2, SEQ ID NO:12) was approximately two times higher than that of recombinant virus containing GGGGS (connector 1, SEQ ID NO:13). In the follow up experiments, focus was on the recombinant virus (connector 2) that showed higher reactivity to M2e monoclonal antibody.

Figure 17A:
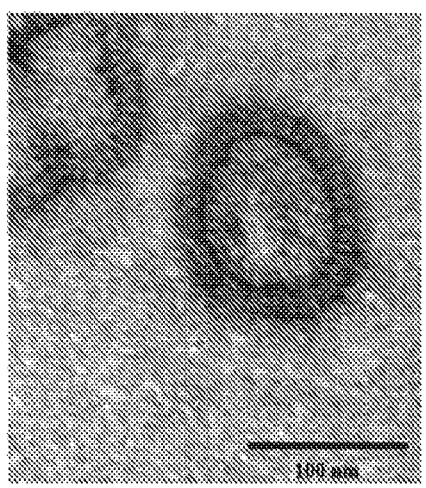
FIGS. 17A and 17B are electron microscopy images showing morphological integrity of recombinant virus carrying chimeric M2e4x-HA conjugate and M2e epitope presentation.
Figure 17B:
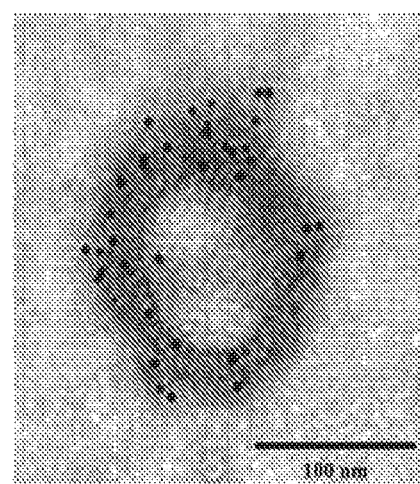

Recombinant Virus Maintains Morphological Integrity of Virus Nanoparticles Presenting M2e Epitopes on the Surfaces Experiments were conducted to examine morphological integrity of recombinant virus carrying chimeric M2e4x-HA conjugate and M2e epitope presentation using electron microscope (FIGS. 17A and B). The overall structural morphology of membrane enveloped recombinant virus was similar to that of wild-type influenza virus, and both spherical virus particles showed an average size of 100 nm size. To probe the M2e epitope presentation on the virus particles, M2e primary and 6 nm gold particle-conjugated secondary antibodies were incubated with virus particles. M2 proteins of wide-type influenza virus were not exposed to the envelope surfaces being inaccessible to antibodies (FIG. 17A). In contrast, many gold particles were clearly visible on the surfaces of recombinant virus with M2e4x-HA, suggesting that M2e epitopes are sufficiently well exposed to M2e antibodies reactive to gold particle secondary antibodies (FIG. 17B). Frilly spherical morphology with spike projections surrounding the virus envelope on the recombinant virus might be due to antibodies bound to the M2e4x-HA molecules on the surfaces. These results suggest that the recombinant virus maintains structural and morphological integrity of virus particles with substantial M2e epitopes accessible to antibodies in HA conjugate molecules on the spherical surfaces.

Recombinant Virus Stably Expresses M2e4x-HA Protein

Figure 17D:
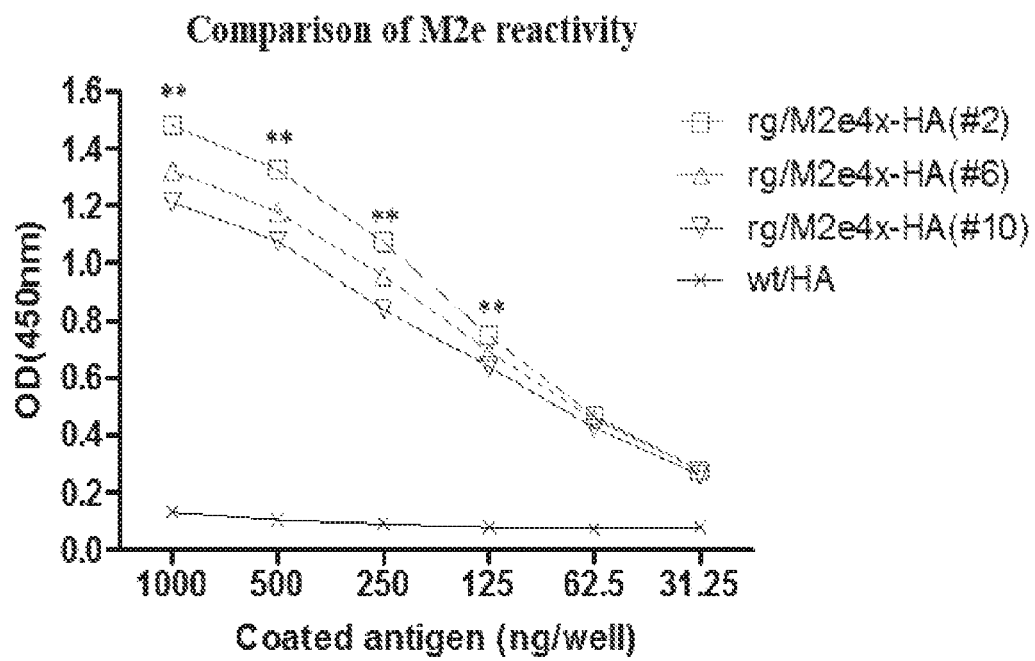

It is important to test the stability of chimeric M2e4x-HA protein in recombinant viruses. Recombinant viruses were harvested at 2, 6, 10 passages and determined the expression of chimeric M2e4x-HA proteins (FIGS. 17C and D). The incorporation of M2e4x-HA and HA proteins was determined in recombinant and with wild-type viruses (FIG. 17C). Wild-type and recombinant viruses showed a similar level of HA protein expression (FIG. 17C, top). When probed with M2e monoclonal antibody (14C2), only recombinant viruses containing chimeric M2e4x-HA showed M2e reactivity at the corresponding HA position. A similar intensity of M2 bands was observed in the passaged recombinant and wild-type viruses (FIG. 17C, bottom). In quantitative determination of chimeric M2e4x-HA protein at the passage #2, #6, and #10, the M2e reactivity in recombinant virus at passage #10 was maintained approximately 80% of M2e reactivity comparing to the passages #2 (FIG. 17D).

Recombinant Virus is Replication-Competent and Shows an Attenuated Phenotype

Figure 18A:
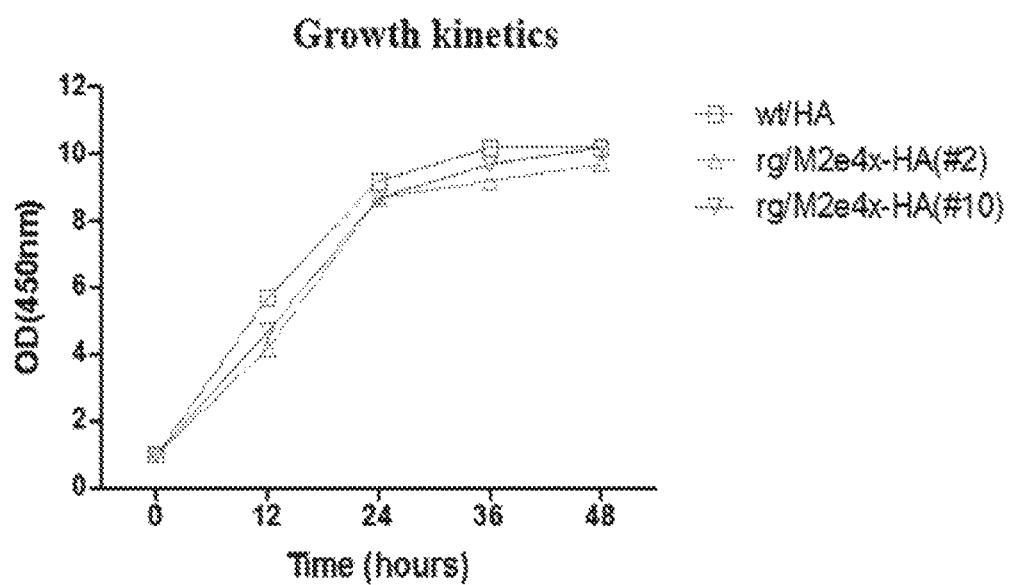
FIGS. 18A to 18D show viral growth kinetics (FIG. 18A), pathogenicity (FIGS. 18B and 18C), and lung viral titer after wild-type virus or M2e4x-HA viruses were inoculated into chicken embryonated eggs.
Figure 18B:
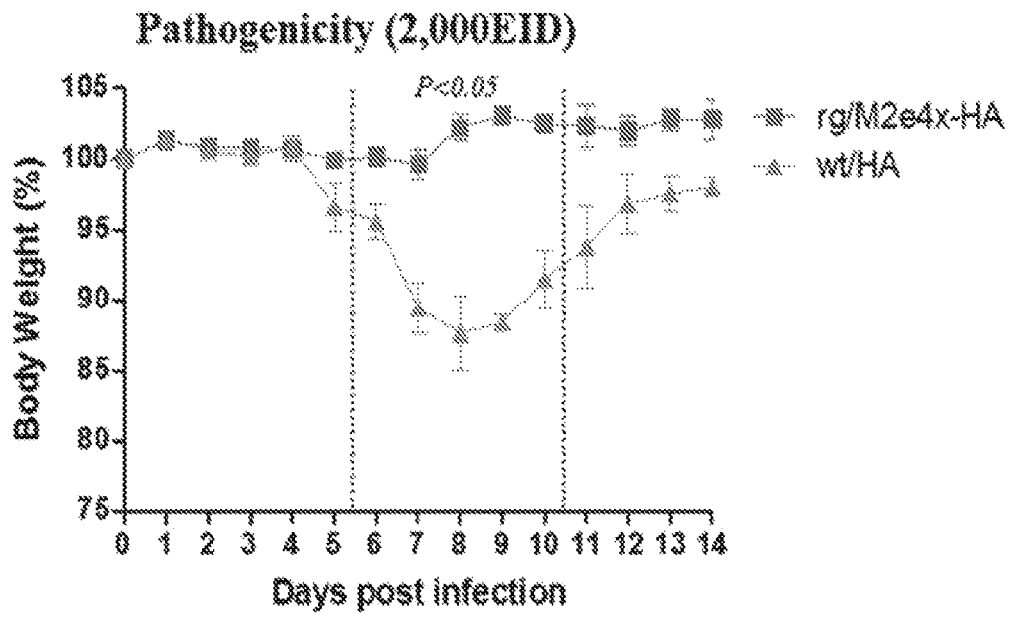
Figure 18C:
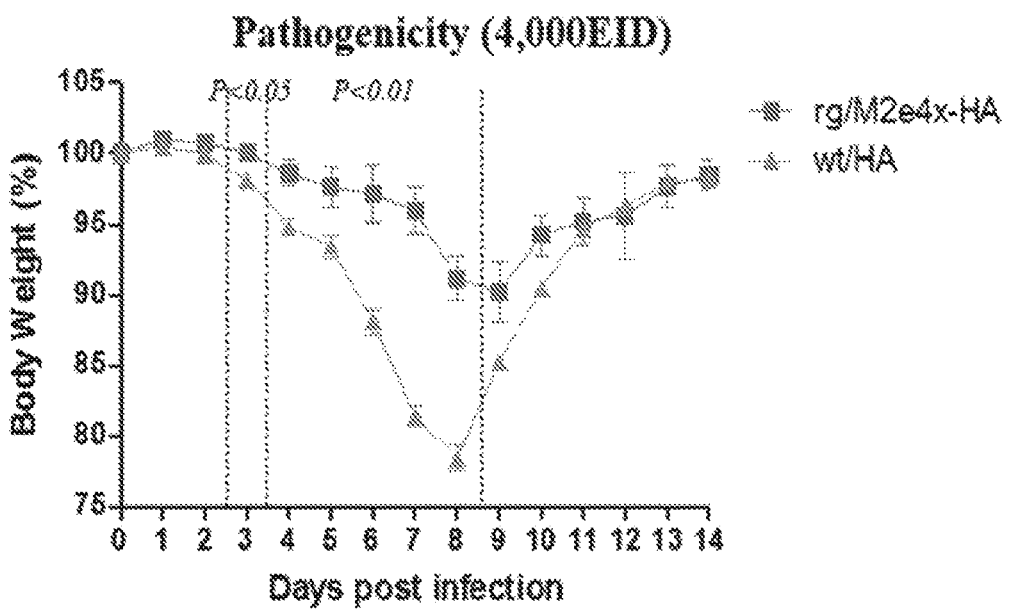
Figure 18D:
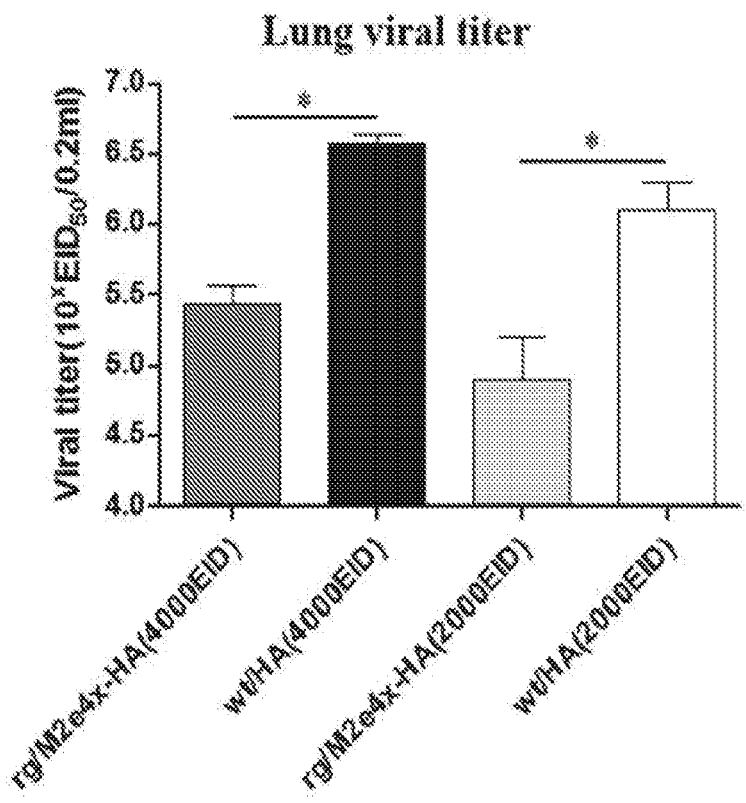

To determine in vitro viral growth kinetics, 15 $EID_{50}$ of wild-type virus or recombinant viruses rg/M2e4x-HA) of passage #2 and #10 were inoculated into chicken embryonated eggs and viral titers were quantified by $EID_{50}$ (FIG. 18A). A similar pattern of growth kinetics was observed in both the recombinant and wild-type virus. These results indicate that recombinant virus is replication-competent and well propagated in chicken eggs without compromising growth properties in eggs. In pathogenicity test of recombinant virus comparing to wild-type virus, mice that received 2,000 $EID_{50}$ of recombinant virus did not show weight loss whereas mice that were infected with wild-type virus displayed significant weight loss up to 13% (FIG. 18B). A high dose (4,000 $EID_{50}$) inoculation with recombinant virus was moderately pathogenic, causing approximately 10% loss of body weight but wild-type virus led to more severe disease as over 22% (FIG. 18C). At day 7 after inoculation, viral titers in mice with recombinant virus were approximately 10 times lower comparing those in mice with wild-type virus (FIG. 18D). These results indicate that the recombinant virus is moderately attenuated in pathogenicity and replication compared to the parental wild-type virus in mice.

Figure 19A:
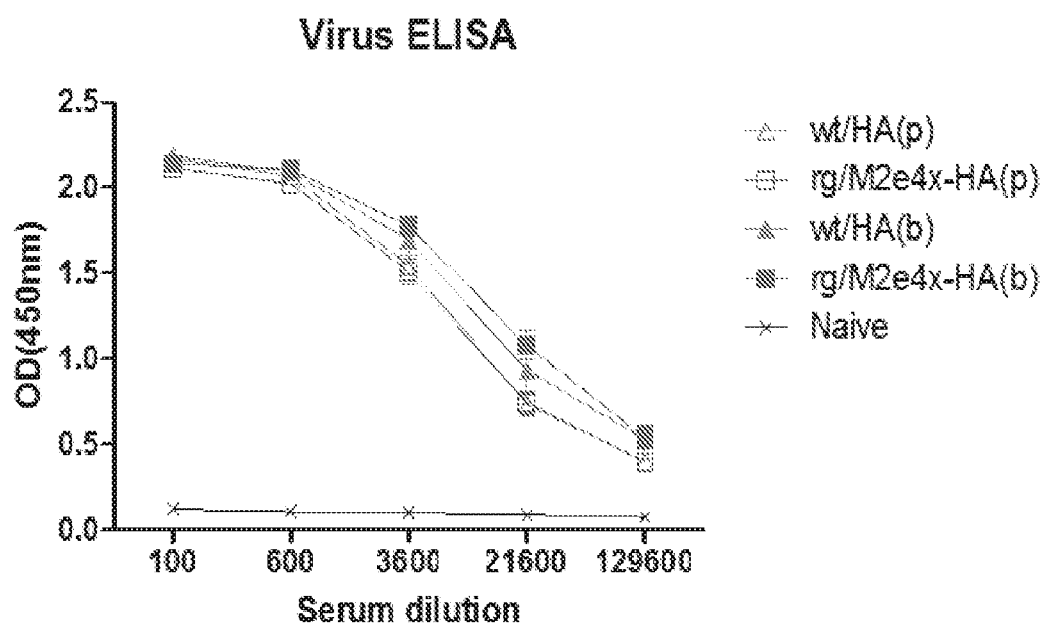
FIGS. 19A to 19C show antibody response after immunization.
Figure 19B:
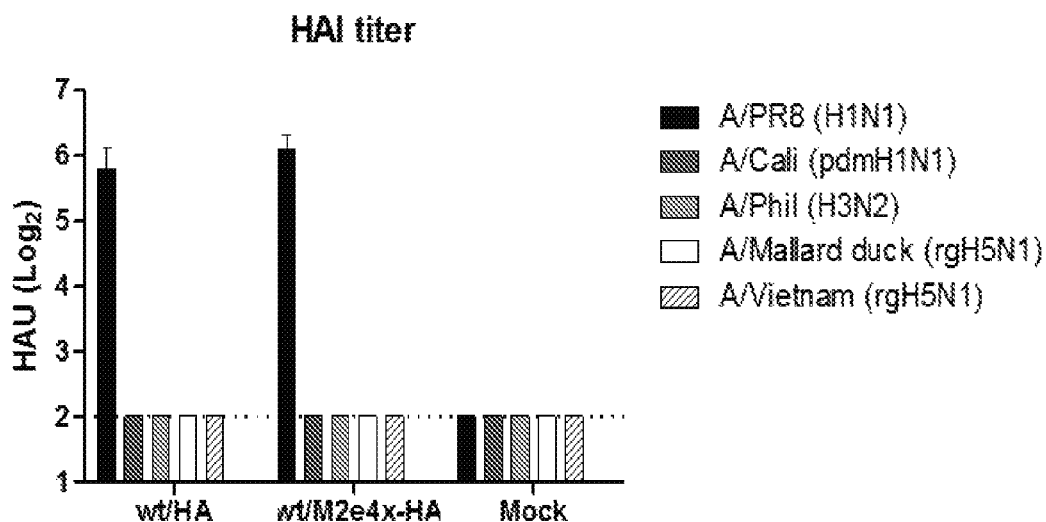
Figure 19C:
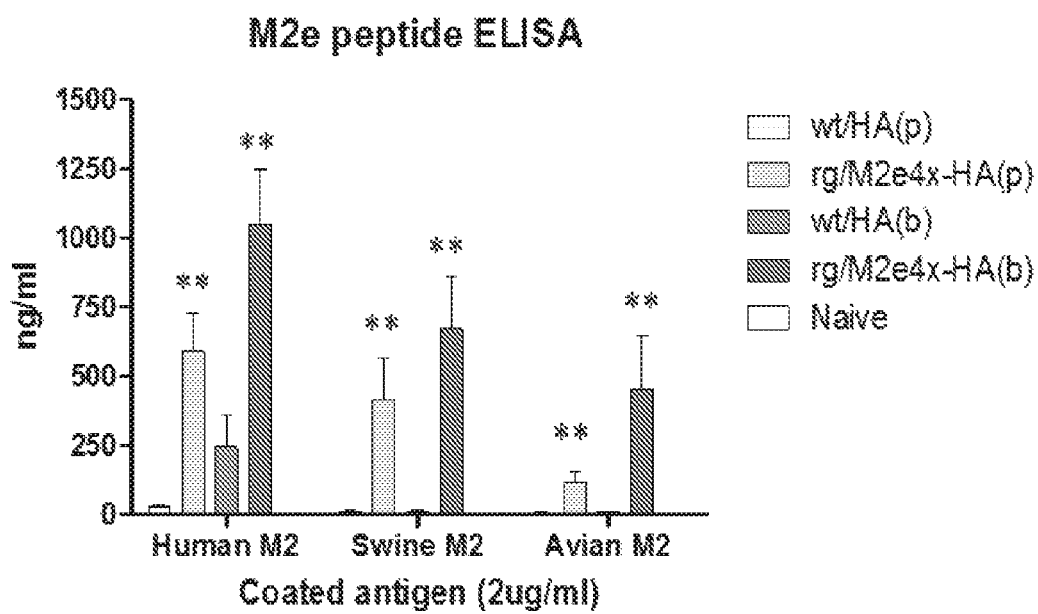

Recombinant Virus is Significantly More Effective than Wild-Type Virus in Inducing Systemic M2e Antibodies without Compromising Virus Immunogenicity Four weeks after each immunization, serum antibody titers to virus and M2e specific peptides were measured. Both prime and boost immune sera from wild-type and recombinant viruses showed high levels of antibody responses specific for virus (FIG. 19A). Mice that were inoculated with recombinant virus (rg/M2e4x-HA) showed similar HAI titers to homologous A/PR8 virus compared to those in wild-type virus immune sera (FIG. 19B). Thus, recombinant virus retains viral immunogenicity without a defect in inducing immune responses to virus compared to wild-type virus. In contrast to HA viral immunogenicity, the group of mice with recombinant virus induced significantly higher levels of M2e antibodies reactive to human, swine, and avian M2e antigens after prime inoculation comparing to the wild-type virus group (FIG. 19C). After boost inoculation, immune sera with recombinant virus showed further enhanced levels of M2e antibodies. These results suggest that recombinant virus (rg/M2e4x-HA) is superior to wild-type virus in inducing M2e specific antibodies without compromising virus immunogenicity.

Immune Sera from Recombinant Virus with M2e4x-HA Confer Enhanced Cross-Protection.

Figure 20A:
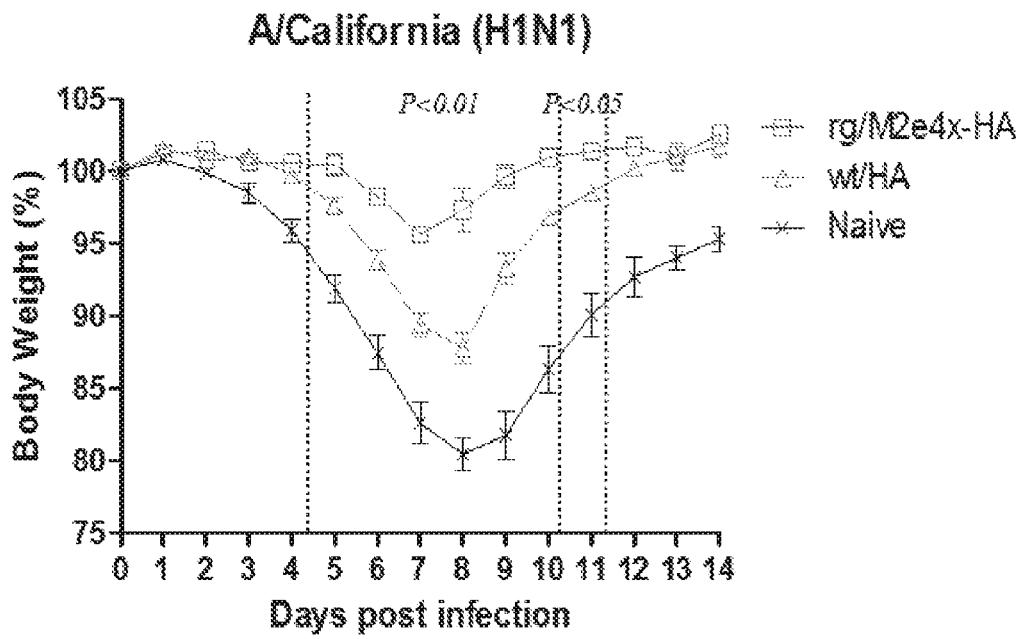
Figure 20B:
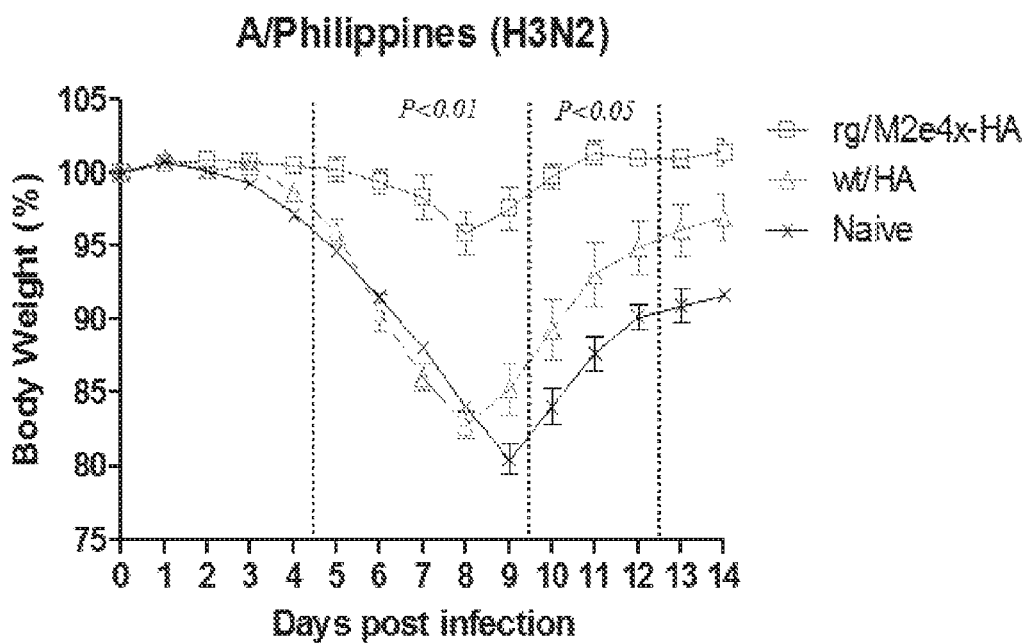
Figures 20C, 20D:
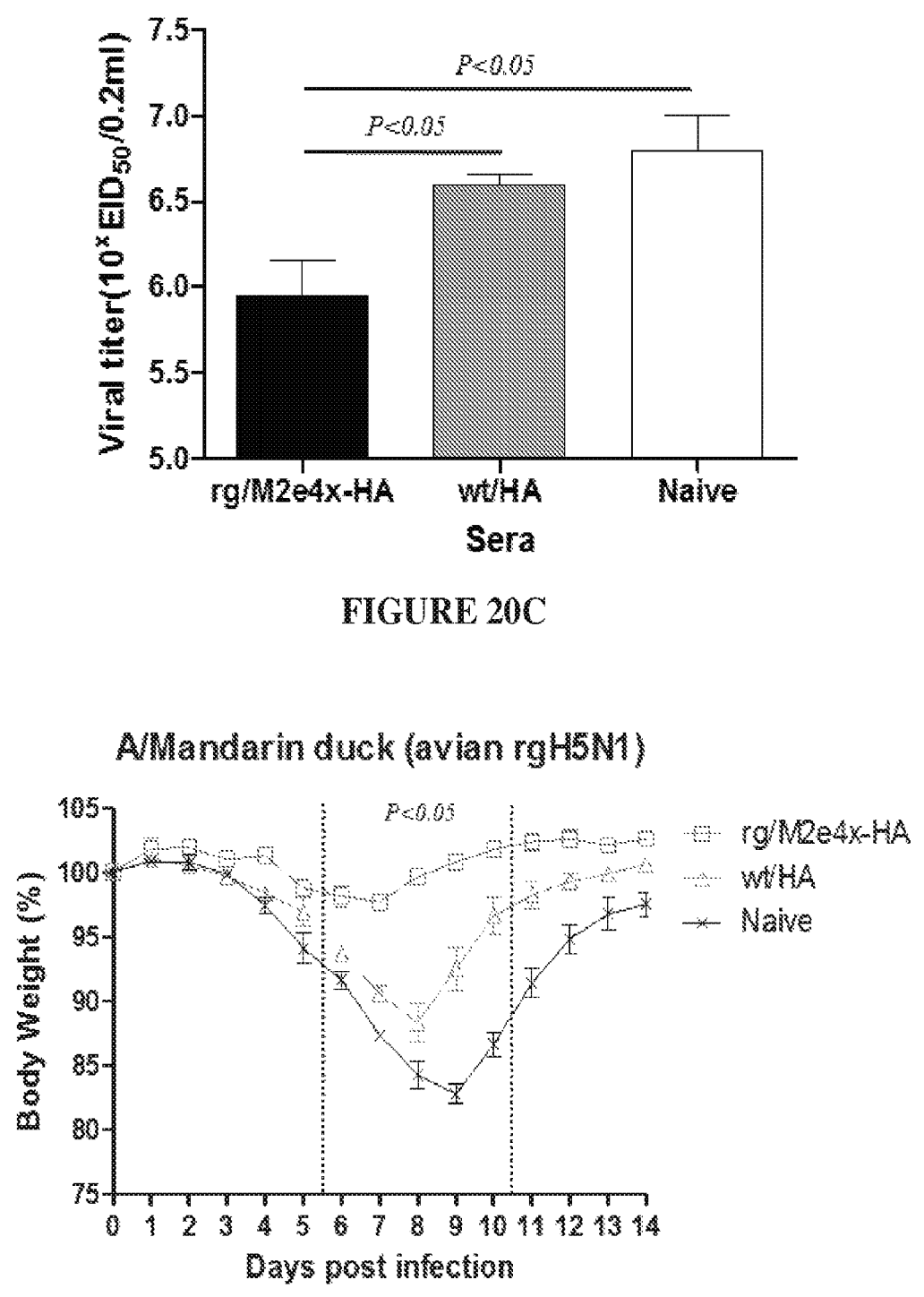
Figure 20E:
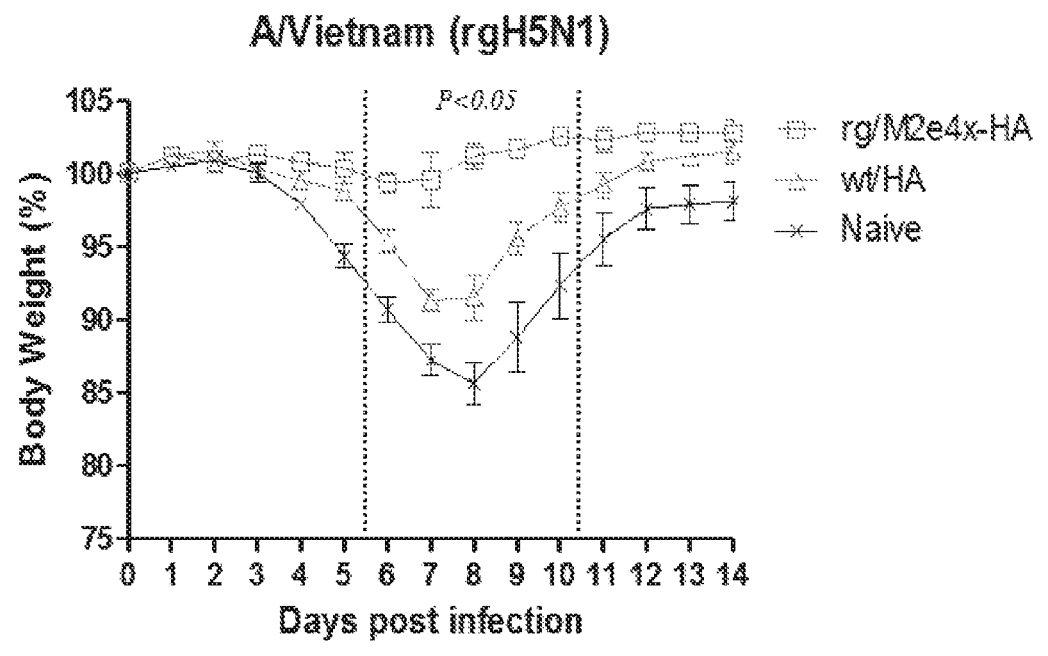

Naïve mice that received recombinant virus (A/PR8, H1N1) immune sera containing various M2e antibodies with pathogenic virus were well protected against A/California/7/2009 (pdmH1N1) and A/Philippines/2/1982 (H3N2) as shown by less than 5% weight loss and then quick recovery (FIGS. 20A and B). Whereas naïve mice that received immune sera of wild-type virus (A/PR8, H1N1) showed approximately 13% and 17% losses, respectively, experiencing severe morbidity. Naïve serum-treated mice exhibited most severe morbidity by showing approximately 18-20% losses (FIGS. 20A and B). Viral titer in lung is an important criterion for viral replication. At day 5 after infection with H3N2 virus, the group of naïve mice that received recombinant virus immune sera showed approximately 5-fold lower replication than that of wild-type virus from lung samples (FIG. 20C). The efficacy of cross-protection against H5N1 influenza viruses, A/Mandarin duck (avian rgH5N1) was further determined with avian M2 and A/Vietnam (rgH5N1) (FIGS. 20D and E). The groups of naïve mice that received M2e antibodies-containing immune sera showed protection against both rgH5N1 viruses without weight loss. In contrast, the groups of naïve mice that were treated with parental wild-type virus immune sera showed significant weight loss of 10-12%. The naïve serum-treated mice exhibited more severe weight loss of 15-17%. These results suggest that recombinant virus (rg/M2e4x-HA) can induce antibodies that confer broadly cross-protection against H1, H3, and H5 subtype influenza viruses. Therefore, universal antibodies to various M2e specific antigens are important for conferring cross protection against antigenically diverse HA subtype influenza A viruses.

Figure 21A:
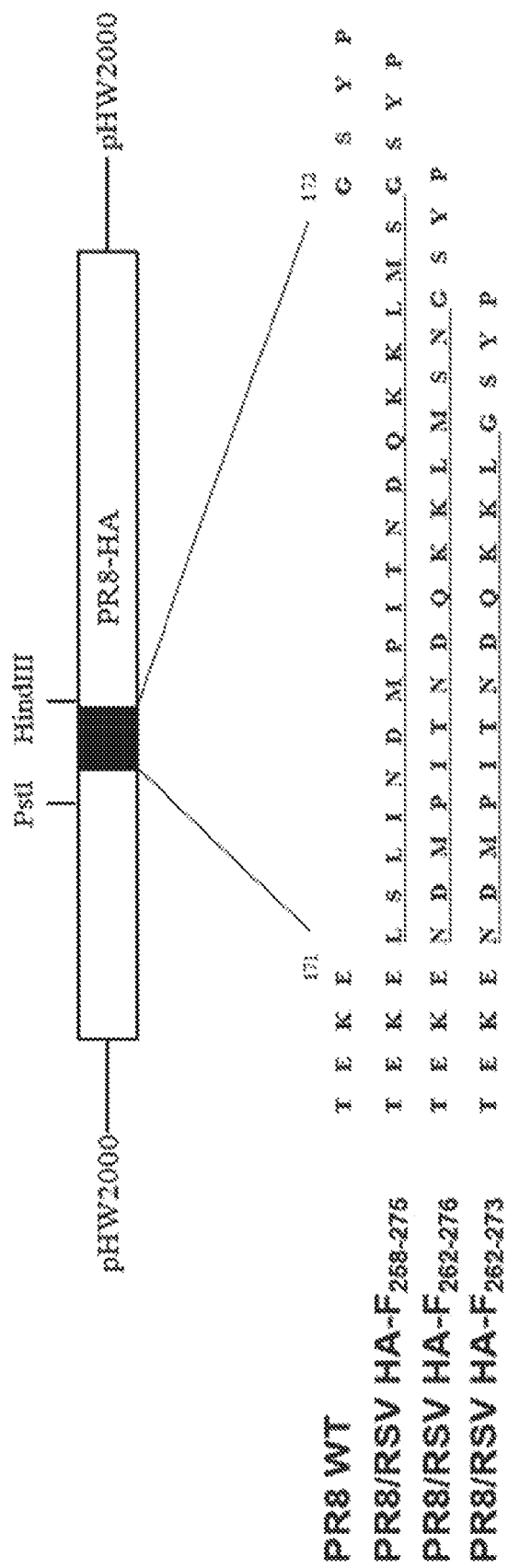
FIGS. 21A to 21C show effect of inserting RSV F nucleotide fragments into the PR8 HA gene to produce chimeric PR8/RSV HA-F constructs.

Example 4: Protection Against Respiratory Syncytial Virus by Inactivated Influenza Virus Carrying a Fusion Protein Neutralizing Epitope in a Chimeric Hemagglutinin Materials and Methods Construction of Chimeric Recombinant PR8/RSV HA-F By introducing silent mutations, a PstI restriction enzyme site was generated at nucleotide position 489 and removed at nucleotide position 74 of the PR8 HA gene. Moreover, new HindIII restriction enzyme site was introduced at nucleotide position 563 of the HA gene. The resulting plasmid was designated PR8-mHA. All silent mutations in the PR8-mHA were introduced by site-directed mutagenesis using the QuikChange Muli Site-Directed Mutagenesis Kit (Agilent Technologies, Boblingen, Germany) by use of a strategy similar to that employed by Li et al. (Li et al., 1993; Li et al., 1992). Three recombinant plasmids of chimeric HA-F constructs were generated by inserting the RSV $F_{772-825}$, $F_{784-828}$, and $F_{784-819}$ nucleotide fragment (Genbank accession number FJ614814) into the PR8-mHA plasmid using PstI and HindIII restriction enzymes, respectively (FIG. 21A).

Recombinant viruses PR8/RSV HA-$F_{258-275}$, PR8/RSV HA-$F_{262-276}$, and PR8/RSV HA-$F_{262-273}$ were generated by reverse genetics using the pHW2000-based eight-plasmid system as described by Hoffmann et al. (Hoffmann et al., 2000). Briefly, 293T cells were cotransfected with eight pHW2000 plasmids containing eight influenza virus gene segments including the chimeric HA-F constructs (FIG. 21A). After 48 h transfection, the supernatant was collected and further inoculated into embryonated chicken eggs. Seventy-two hours after inoculation, the presence of the recovered recombinant viruses was proved by hemagglutination of chicken red blood cells. To determine the incorporation of the antigenic site II of the RSV F protein into recombinant HA-F chimeric proteins, the reactivity to palivizumab (MedImmune, Gaithersburg, Md.) was analyzed by enzyme-linked immunosorbent assay (ELISA).

Immunizations and RSV Challenge of Mice

For animal experiments, six- to eight-week-old female BALB/c mice (n=5; Charles River Laboratories) were immunized intramuscularly with 10 μg of formalin-inactivated PR8/RSV HA-$F_{262-276}$ virus or 2 μg of inactivated PR8/RSV HA-$F_{262-276}$ virus alone or mixed with 50 μg of aluminum hydroxide (alum) adjuvant or 2 μg of inactivated PR8 wild-type (PR8 WT) virus. The FI-RSV control group was intramuscularly immunized with 2 μg of FI-RSV in alum adjuvant. Blood samples were obtained three weeks after each immunization. Immunized mice were challenged with RSV A2 strain ($2 \times 10^5$ PFU) at 4 weeks after boost immunization.

Assays for Antibody Responses and Virus Titration

RSV F protein-specific antibodies (IgG, IgG1, and IgG2a) were determined in samples by enzyme-linked immunosorbent assay (ELISA) as previously described (Lee et al., 2015. Virology 476, 217-225). To determine hemagglutination inhibition (HI) titers, serum samples were incubated with receptor destroying enzyme (RDE, Denka Seiken, Japan) and heated at 56° C.

RSV-specific neutralizing antibody titers in immune sera were evaluated by a standard method. Briefly, the serum samples were heat-inactivated at 56° C. and serially diluted two-fold in serum-free DMEM. Equal volumes of RSV (300 PFU/well) were mixed with diluted sera. A mixture of RSV with or without immune sera was incubated at 33° C., 5% $CO_2$ for 1 h prior to incubation in the HEp-2 cell monolayers. The next steps were followed by an immune-plaque assay procedure. After fixing with 5% formaldehyde in PBS and blocked with 5% non-fat dry milk in PBST, anti-RSV F monoclonal antibody (131-2A, Millipore) and then HRP conjugated anti-mouse IgG antibody were used. Individual plaques were developed using 3,3'-diaminobenzidine tetrahydrochloride (DAB) substrate (Invitrogen, Camarillo, Calif.) and then counted.

Cytokine Assay

Challenged mice were euthanized at 5 days post-infection (p.i.). Each lung was homogenized and centrifuged at 1400×g at 4° C. for 10 min. Cytokine and eotaxin levels in the lung extract were analyzed via ELISA according to the manufacturers' instructions (eBioscience and R&D Systems) in duplicate against a standard curve.

Pulmonary Histology of RSV-Infected Mice

The lung tissues were fixed in 10% neutral buffered formalin for 24 hrs, transferred into 70% ethanol, and followed by routine processes. The lung tissues embedded in paraffin, sectioned into a thickness of 5 μm and stained with hematoxylin and eosin (H&E), periodic acid-Schiff stain (PAS) or hematoxylin and congo red (H&CR) as described previously (Hwang et al., 2014). At least eight sections per mouse were obtained for histopathologic analysis. Tissue sections stained with H&E were scored blindly for the degree of inflammation around blood vessels, airways, or interstitial spaces, on a scale of 0 to 3. For sections stained with PAS, the percentage of airways positive for PAS in ten individual airways of each mouse was scored.

Results

Chimeric Influenza Viruses Carrying an HA-F Shows Reactivity to RSV Neutralizing Antibody The antigenic site B of influenza virus H3 protein and the antigenic site Sa of H1 protein virus is located at the top of the protein (Caton et al., 1982; Wiley et al., 1981). It has been previously demonstrated that the 12-ammino-acid (aa) peptide can be inserted into the loop between the glycine and aspartic acid residues (Li et al., 1993. J Virol 67, 6659-6666). The 18-aa peptide LSLINDMPITNDQKKLMS ($F_{258-275}$, SEQ ID NO:20), the 15-aa peptide NDMPITNDQKKLMSN ($F_{262-276}$, SEQ ID NO:21), and the 12-aa peptide NDMPITNDQKKL ($F_{262-273}$, SEQ ID NO:22), derived from the antigenic site II of RSV F protein, which is recognized by palivizumab (Synagis), were selected for expression in the HA antigenic site Sa of PR8. Chimeric recombinant influenza viruses PR8/RSV HA-$F_{258-275}$, PR8/RSV HA-$F_{262-276}$, and PR8/RSV HA-$F_{262-273}$ were generated using the reverse genetics system (FIG. 21A).

Figure 21B:
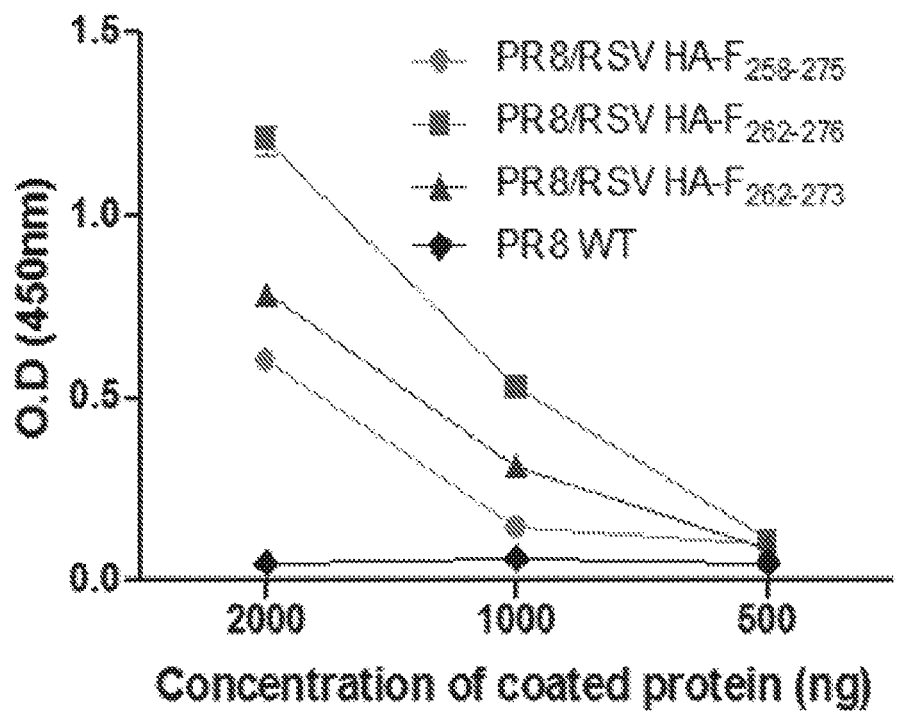

All 3 recombinant chimeric influenza viruses were successfully rescued as confirmed by growth in eggs. The antigenic properties of the chimeric recombinant viruses were determined by ELISA using palivizumab (FIG. 21B). The parental virus PR8 did not show any reactivity to palivizumab. The reactivity of palivizumab monoclonal antibody to the 15-aa PR8/RSV HA-$F_{262-276}$ was estimated to be at least 1.7-fold higher than that to the 18-aa PR8/RSV HA-$F_{258-275}$. Moreover, compared with that of the 12-aa PR8/RSV HA-$F_{262-273}$, the reactivity of palivizumab antibody to the 15-aa PR8/RSV HA-$F_{262-276}$ was approximately 1.4-fold higher. These data suggest that replication competent PR8 virus containing 18-aa RSV F foreign peptide in the antigenic site Sa of globular head domain can be rescued. However, the 18-aa PR8/RSV HA-$F_{258-275}$, showed the lowest reactivity to palivizumab.

Figure 21C:
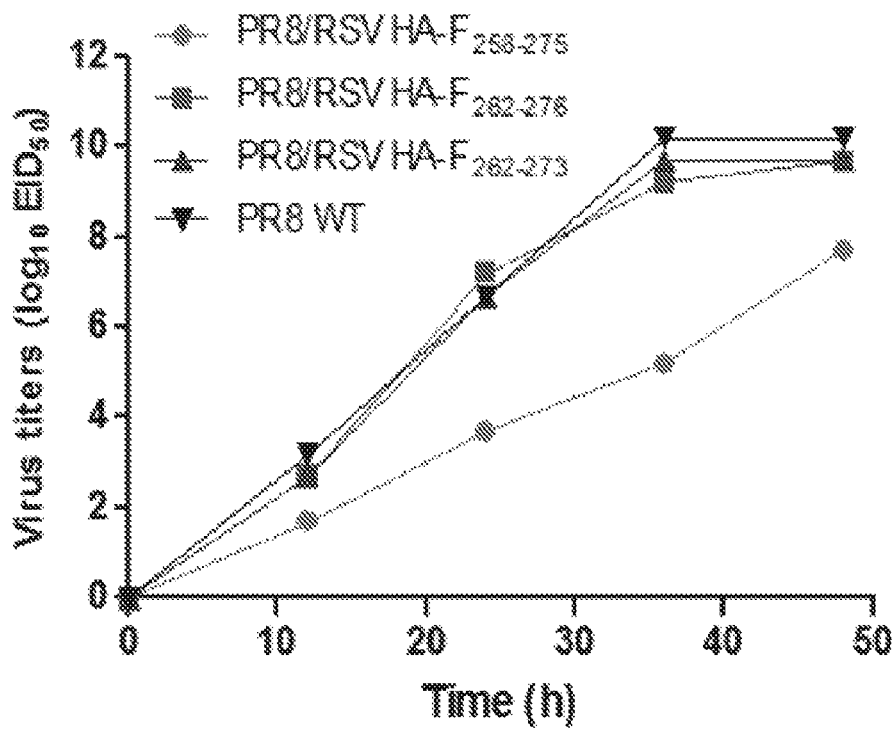

The 15-aa RSV F Epitope-Carrying Recombinant Influenza Virus with Highest Palivizumab Reactivity Maintains an Equal Growth Property in Eggs To compare in vitro viral growth kinetics, eggs were inoculated at a 15 $EID_{50}$ (50% egg infective dose) of PR8 WT (wild type control), the 18-aa PR8/RSV HA-$F_{258-275}$, the 15-aa PR8/RSV. A-$F_{262-276}$, and the 12-aa PR8/RSV HA-$F_{262-273}$. At various times after inoculation, virus titers in allantoic fluids were determined by an egg infection assay (FIG. 21C). The growth kinetics of the 15-aa PR8/RSV HA-$F_{262-276}$ or the 12-aa PR8/RSV HA-$F_{262-273}$ except the 18-aa PR8/RSV HA-$F_{258-275}$ in eggs was found to be comparable to that of PR8 WT. The insertion of an 18-aa epitope domain might have caused a conformational change on the head domains of HA protein, lowering the growth property of the chimeric HA-F virus.

Figure 22B:
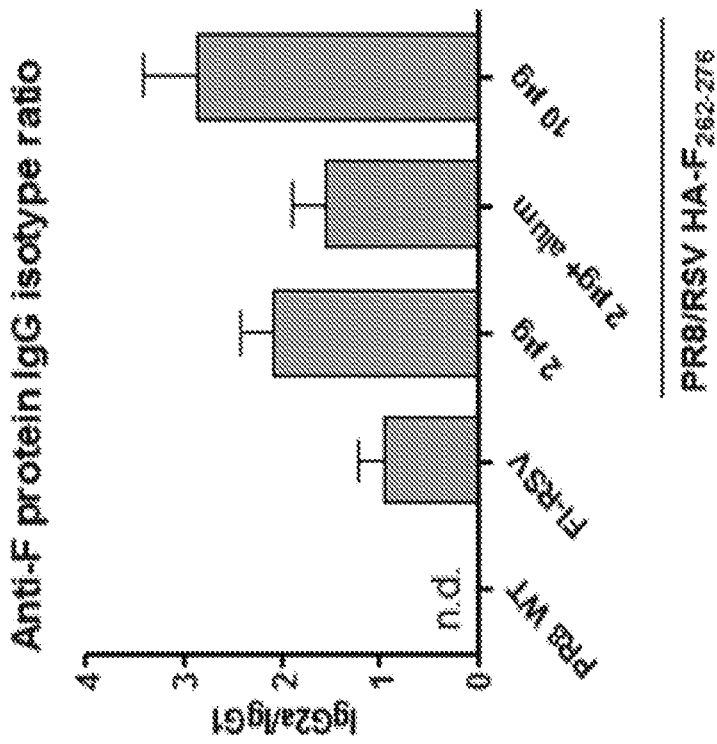
Figure 22A:
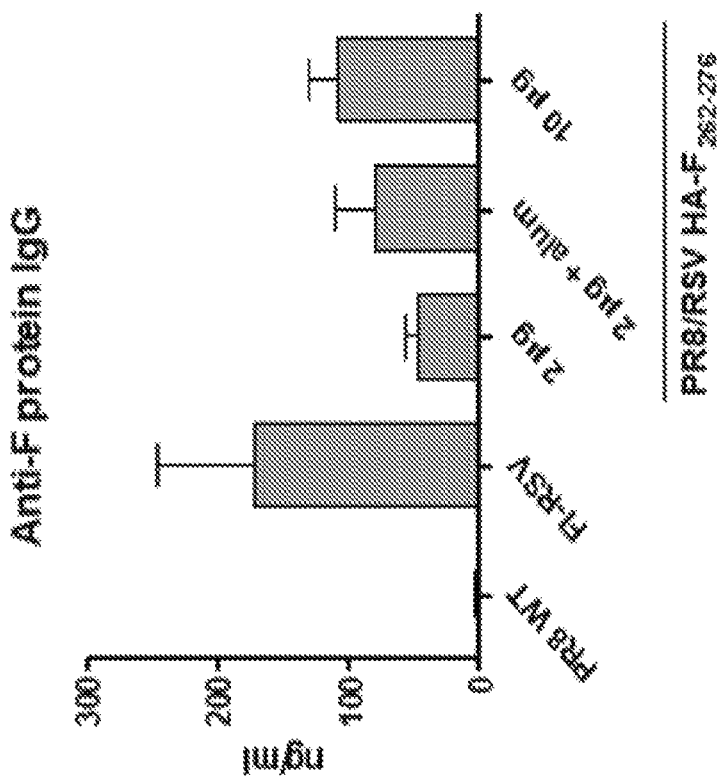

Inactivated PR8/RSV HA-$F_{262-276}$ Vaccination is Effective in Inducing RSV Neutralizing Antibodies Inactivated influenza vaccine is safer and thus approved in infants compared to live attenuated vaccines. For immunization studies, we selected a 15-aa recombinant PR8/RSV HA-$F_{262-276}$ virus which showed the highest reactivity to palivizumab. Immunogenicity of recombinant PR8/RSV HA-$F_{262-276}$ virus was determined in mice intramuscularly immunized with inactivated PR8/RSV HA-$F_{262-276}$ or PR8 WT virus. To determine potential dose sparing effects of adjuvants, inactivated PR8/RSV HA-$F_{262-276}$ virus was mixed with alum. Three weeks after boost, RSV F-specific antibody responses were measured (FIGS. 22A and 22B).

IgG antibodies specific for RSV F proteins were observed in sera from mice vaccinated with 10 µg of PR8/RSV HA-$F_{262-276}$ (109.2±50 ng/ml), 2 µg of PR8/RSV HA-$F_{262-276}$ with alum (96.7±63 ng/ml), and 2 µg of PR8/RSV HA-$F_{262-276}$ (48.0±16 ng/ml), respectively. Moreover, 10 µg of PR8/RSV HA-$F_{262-276}$ and 2 µg of PR8/RSV HA-$F_{262-276}$ plus alum group showed significantly higher ratios of IgG2a/IgG1 isotypes than the FI-RSV group (p<0.05, FIG. 22B).

The FI-RSV group showed the highest mean neutralizing antibody titer of 7.7±0.58 log 2 against RSV (FIG. 22C). In addition, mice vaccinated with recombinant PR8/RSV HA-$F_{262-276}$ virus alone or mixed with alum showed high neutralizing antibody titers against RSV than those of the PR8 WT control group. There was no significant difference in RSV neutralizing titers among the groups (FIG. 22C). All mice immunized with recombinant or PR8 WT virus showed high titers of HI activity up to 8.75±0.6 log 2 (FIG. 22D), indicating that there is no defect in virus immunogenicity.

Figure 23B:
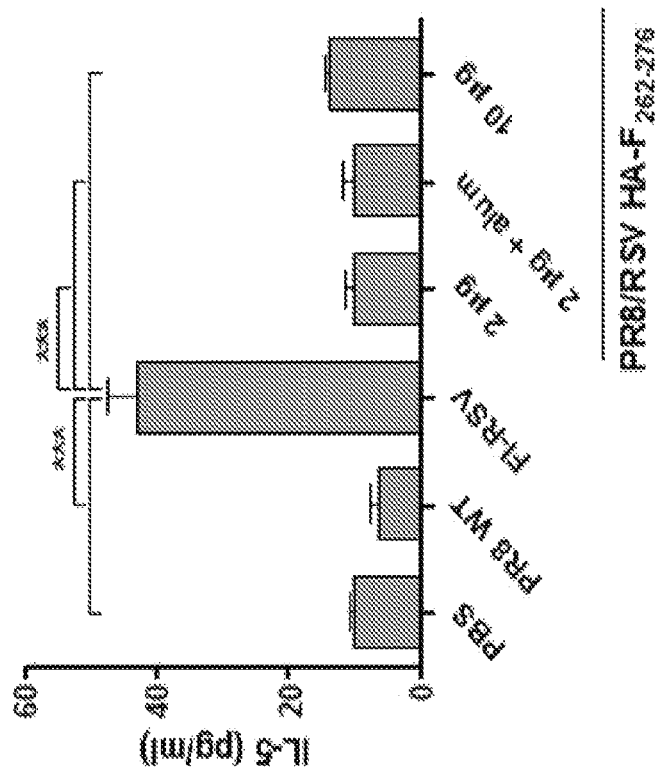
FIGS. 23A to 23D show inactivated PR8/RSV HA-$F_{262-276}$ vaccine confers protection against RSV without induce RSV-specific T cell response.
Figure 23A:
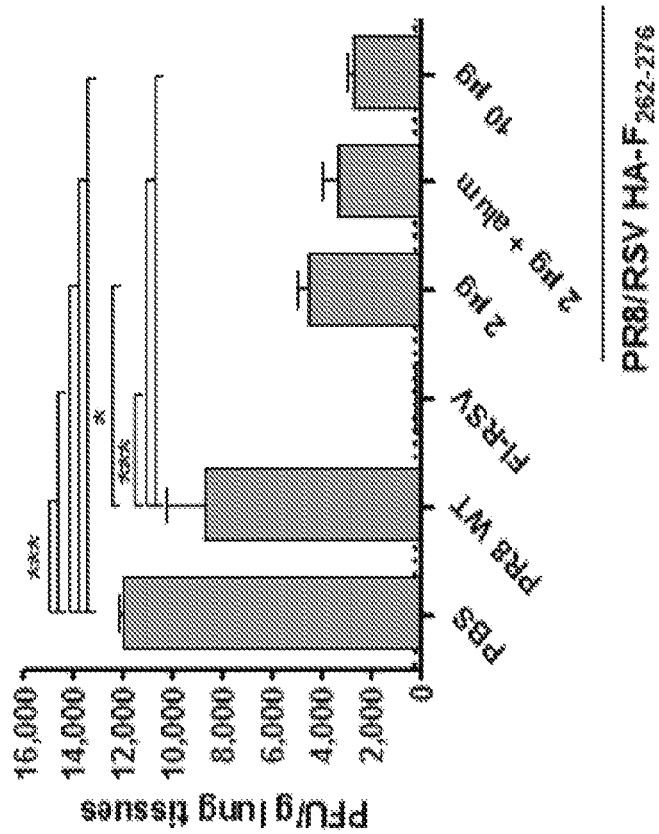

Inactivated Chimeric PR8/RSV HA-$F_{262-276}$ Vaccine Confers Protection Against RSV without Inducing RSV-Specific T Cell Responses To assess the protective efficacy of inactivated recombinant PR8/RSV HA-$F_{262-276}$ vaccine, groups of mice were challenged with RSV A2 (2×10$^5$ PFU/mouse) at 4 weeks after boost. Mice vaccinated with FI-RSV showed complete protection against RSV A2 at 5 day p.i. Lung viral loads were significantly decreased in mice vaccinated with recombinant PR8/RSV HA-$F_{262-276}$ virus alone or mixed with alum compared with PBS mock or PR8 WT controls (FIG. 23A). These results indicate a pattern of inverse correlation between RSV lung viral titers and neutralizing antibodies.

Figure 23D:
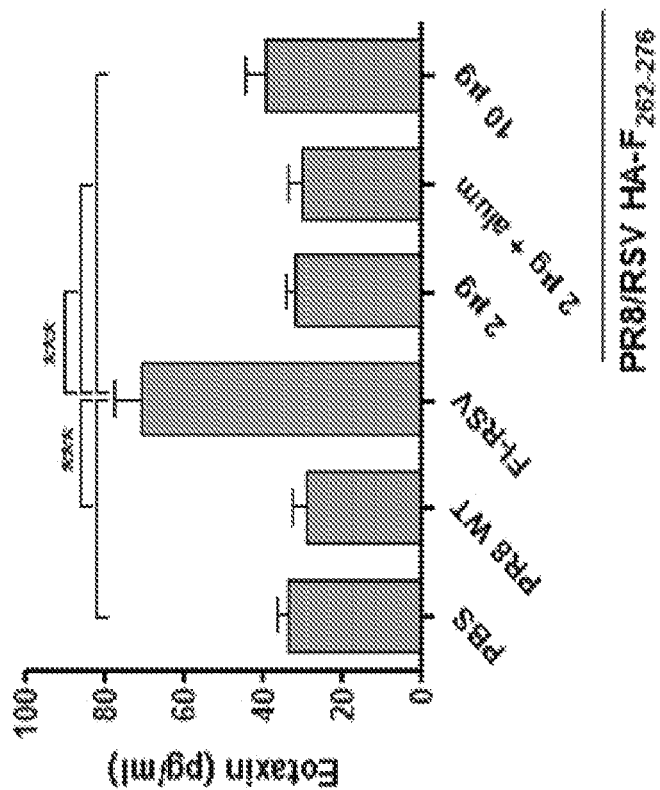
Figure 23C:
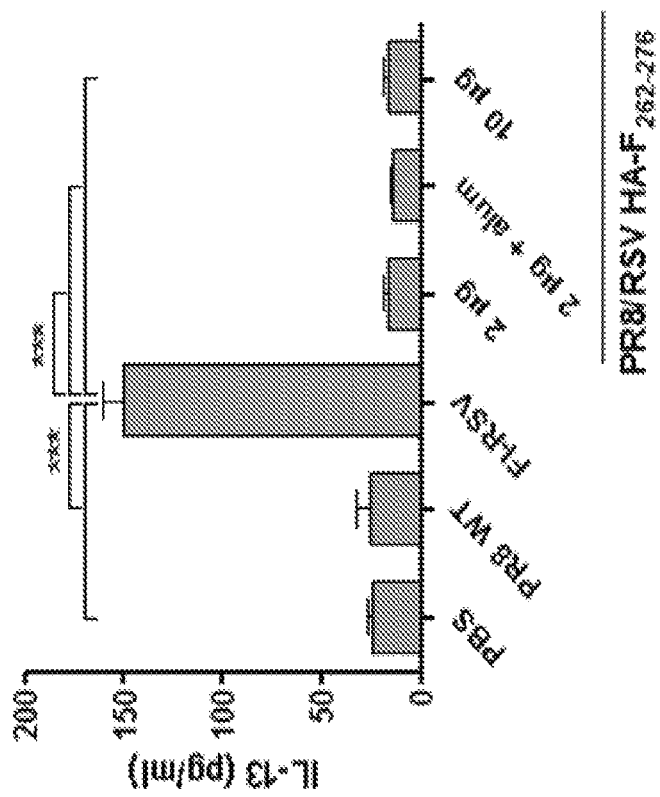

T helper type 2 (Th2) cytokines such as IL-5 and IL-13 have been shown to play an important role in RSV-induced pulmonary injury. The highest levels of cytokines and chemokine were observed in the lung extracts from the FI-RSV group at day 5 p.c. The levels of IL-5 (FIG. 23B), IL-13 (FIG. 23C) and eotaxin (FIG. 23D) were significantly lower in mice immunized with recombinant PR8/RSV HA-$F_{262-276}$ vaccines, PBS mock, and PR8 WT than those in the FI-RSV group.

To determine whether recombinant PR8/RSV HA-$F_{262-276}$ vaccination influenced antigen-specific T cell responses, IFN-γ-producing lung and spleen cell spots were measured after in vitro stimulation with $F_{85-93}$ peptide. The spot numbers of IL-4- or IFN-γ-secreting cells were detected at a significantly lower level in the lungs from mice in the recombinant PR8/RSV HA-$F_{262-276}$ vaccine groups and the PBS control group than those from the FI-RSV group. Interestingly, the PR8 WT group showed substantial levels of IFN-γ-secreting cells in lungs and spleens, but there was no significant difference. Considering a moderately lower level of RSV lung viral titers in the PR8 WT group, IFN-γ-secreting cells in this group appear to have a role in reducing RSV replication in lungs.

Inactivated PR8/RSV HA-$F_{262-276}$ does not Cause Pulmonary Histopathology

Figure 24A:
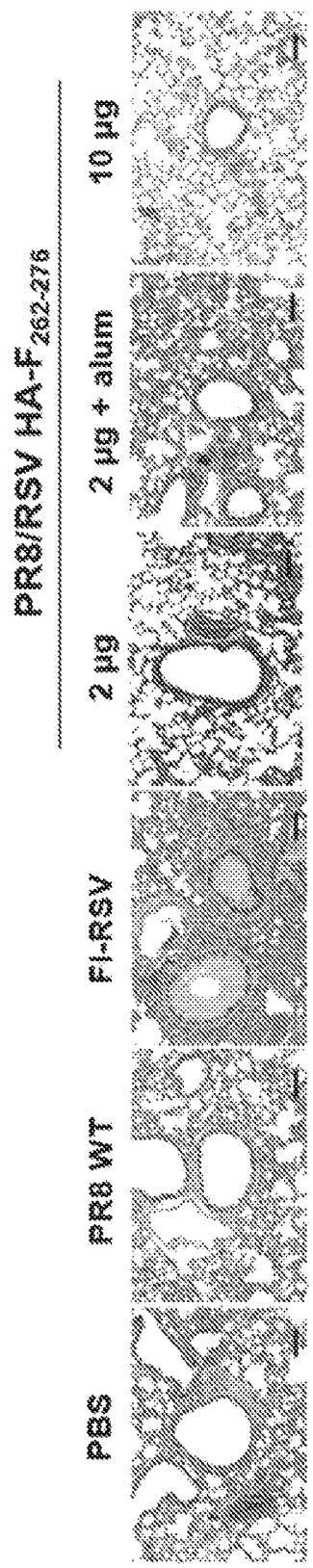
Figures 24B, 24C:
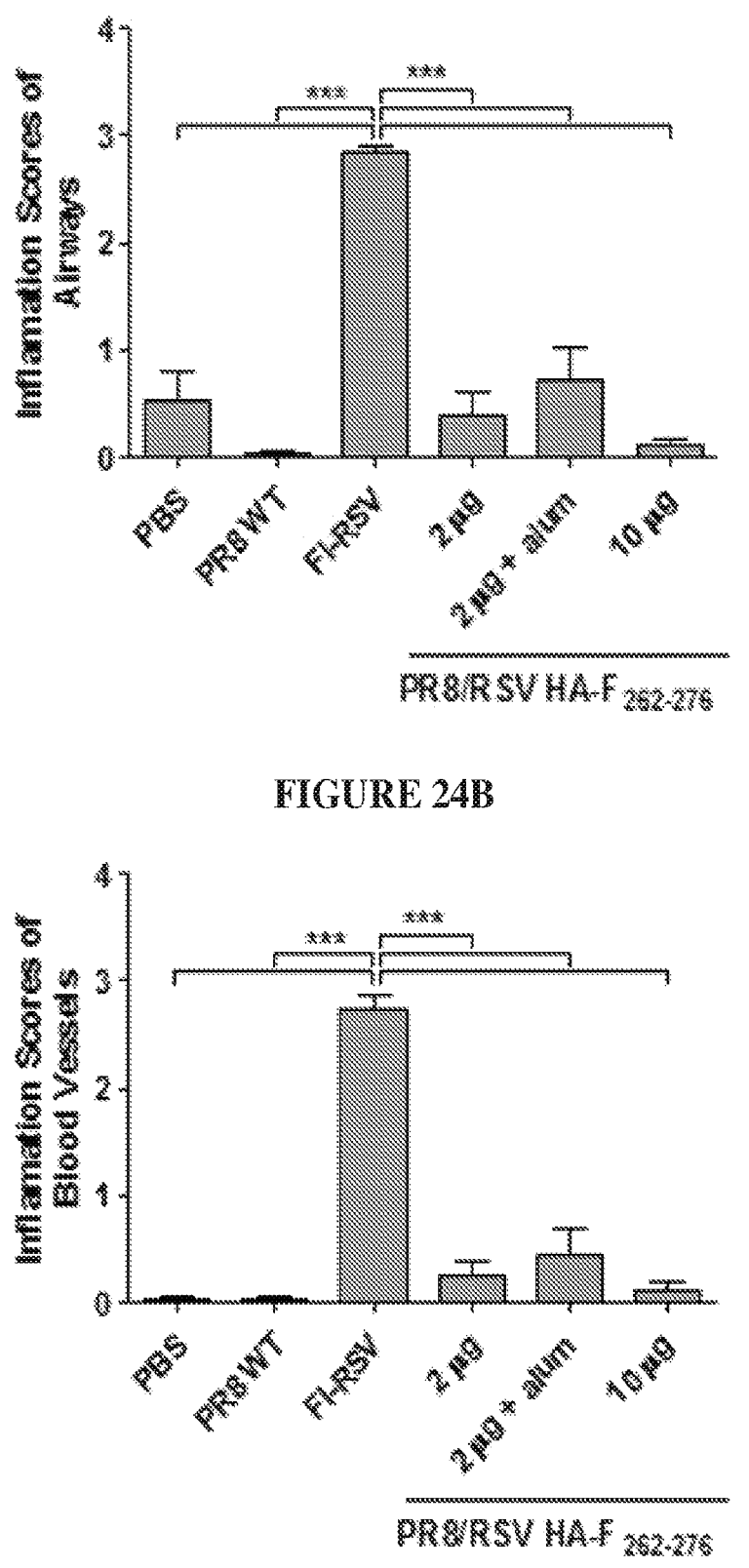
Figure 24D:
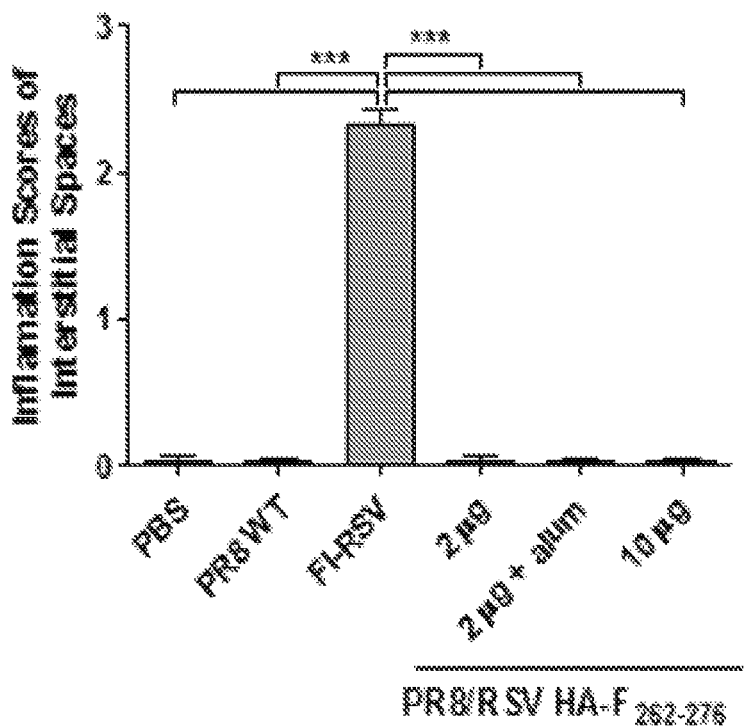

Developing a safe and effective RSV vaccine has been a challenge for over a half century. Pulmonary histopathology upon RSV infection was examined for assessing the safety of RSV vaccine (FIG. 24). FI-RSV immune mice showed highest inflammation around the airways (pathology score 2.9, FIG. 24A, 24B), blood vessels (pathology score 2.7, FIG. 24A, 24C), and interstitial spaces (pathology score 2.3, FIG. 24A, 24D) after RSV challenge. Therefore, despite lung viral control, mice immunized with FI-RSV displayed severe vaccine-enhanced disease in the lungs upon RSV infection. In contrast, lung tissues from the mice immunized with PR8/RSV HA-$F_{262-276}$, PR8 WT and PBS did not reveal an obvious sign of inflammation around the airways, blood vessels, and interstitial spaces.

The lung sections from mice were stained with PAS for visualization of mucus production. These sections were quantitatively assessed for the percentage of airway linings showing PAS staining. PR8/RSV HA-$F_{262-276}$ vaccine-immunized mice with or without alum adjuvant did not show PAS-positive airways.

The degrees of lung eosinophilia were estimated using H&CR staining to enumerate eosinophils and expressed as numbers of eosinophils present per 40× field. Eosinophil accumulation in the lungs was significantly greater in FI-RSV-immunized mice than in mice that were vaccinated with the inactivated PR8/RSV HA-$F_{262-276}$ vaccine or control PR8 WT.

Example 5: Generation and Protective Efficacy of Recombinant Live Attenuated Influenza Virus Vaccines (LAIV) Carrying a Fusion Protein of Heterologous Tandem Repeat M2e Epitopes in a Chimeric Hemagglutinin Generation of LAIV The temperature-sensitive (ts) phenotype maps to five amino acids encoded on three different gene segments, segments for PB1 (K391E, E581G, A661T), PB2 (N265S), and NP (D34G), and has been shown to be genetically stable following passage in humans and immunocompromised animals (Murphy and Coelingh, 2002. Viral Immunol 15, 295-323). These amino acids in combination enable efficient virus replication at 33° C. but effectively shut off replication at 39° C. Sequence alignments of the PB1, PB2, and NP genes of cold-adapted A/AA/6/60 (MDV-A) and PR8 (Hoffmann et al., 2002. Vaccine 20, 3165-3170) revealed that the five loci responsible for the ts phenotype of MDV-A, only the NP (D34G) locus were identical between these two strains. To generate a recombinant temperature-sensitive virus, the four ts loci were introduced into the PR8 PB1 (pHW191-PB2) and PB2 (pHW192-PB1) expression plasmids (Hoffmann et al., 2002. Vaccine 20, 3165-3170) by site-directed mutagenesis using the QuikChange Multi Site-Directed Mutagenesis Kit (Agilent Technologies, Boblingen, Germany). Recombinant viruses were rescued using the pHW2000-based eight-plasmid system described by Hoffmann et al. (Hoffmann et al., 2000. Proc Natl Acad Sci USA 97, 6108-6113). Briefly, 293T cells were cotransfected with eight pHW2000 plasmids containing all eight influenza virus gene segments. After 48 h, the medium was collected and inoculated to embryonated chicken eggs. After 72 h, the presence of LAIV in the allantoic fluids was determined by hemagglutination of chicken red blood cells. The low temperature growth properties and attenuated phenotypes of LAIV were confirmed.

Strategies for Introducing Foreign Gene Epitopes on the Antigenic Site Sa of PR8 HA By introducing silent mutations, a PstI restriction enzyme site was generated at nucleotide position 489 and removed at nucleotide position 74 of the PR8 HA gene in the Plasmid pHW194-HA. Moreover, new HindIII restriction enzyme site was introduced at nucleotide position 563 of the HA gene using silent mutation. The resulting plasmid was designated pHW194-HAm. All silent mutation in the pHW194-HAm was introduced by site-directed mutagenesis using the QuikChange Muli Site-Directed Mutagenesis Kit (Agilent Technologies, Böblingen, Germany) by use of a strategy similar to that employed by Li et al. (Li et al., 1993).

Figure 25:
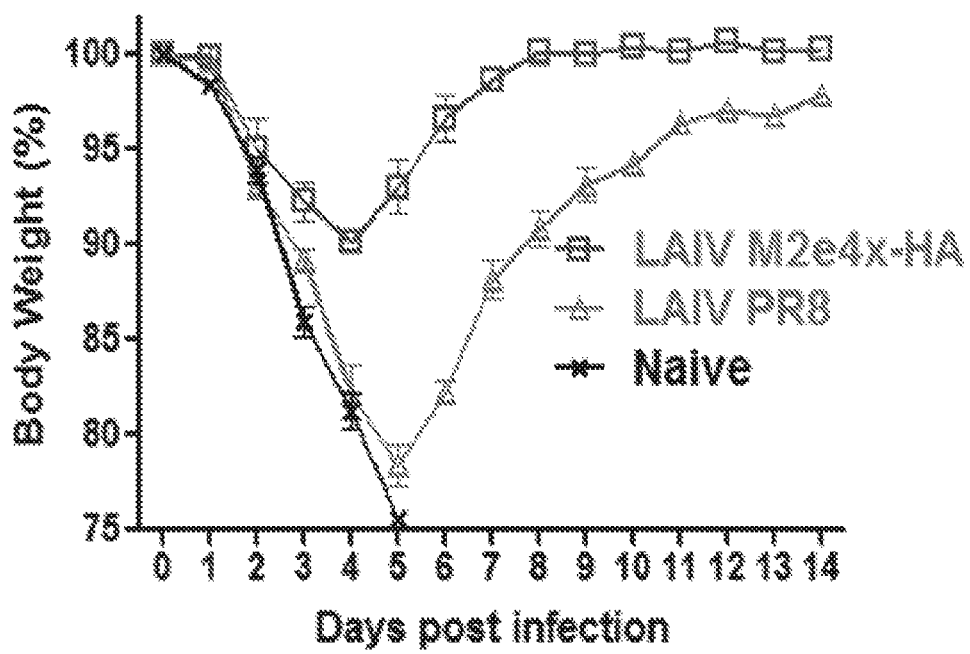
FIG. 25 is a graph showing body weight (%) of mice inoculated with LAIV PR8 and recombinant LAIV M2e4x-HA one time.

Protective Efficacy of Recombinant Live Attenuated Influenza Virus Vaccines (LAIV) Carrying a Fusion Protein of Heterologous Tandem Repeat M2e Epitopes in a Chimeric Hemagglutinin As described in the Example 3, M2e4x-HA was generated and used to make recombinant LAIV carrying heterologous tandem repeat M2e epitopes in a chimeric fusion hemagglutinin (LAIV M2e4x-HA, FIG. 25). Groups of mice were inoculated with LAIV PR8 and recombinant LAIV M2e4x-HA one time. At 4 weeks after single dose intranasal immunization of mice with recombinant LAIV M2e4x-HA, the cross protective efficacy was determined (FIG. 25). Significantly improved heterosubtypic cross protection against H3N2 virus (A/Phil/82) by recombinant LAIV 4×M2e-HA (n=5 mice per group). New data further support the proof-of concept that recombinant LAIV (H1N1) 4×M2e-HA can confer significantly improved heterosubtypic cross protection against H3N2 virus (A/Phil/82) by conferring 100% protection and preventing weight loss. In contrast, LAIV PR8 (attenuated H1N1 PR8) showed severe weight loss and only 50% survival rates.

Figure 26:
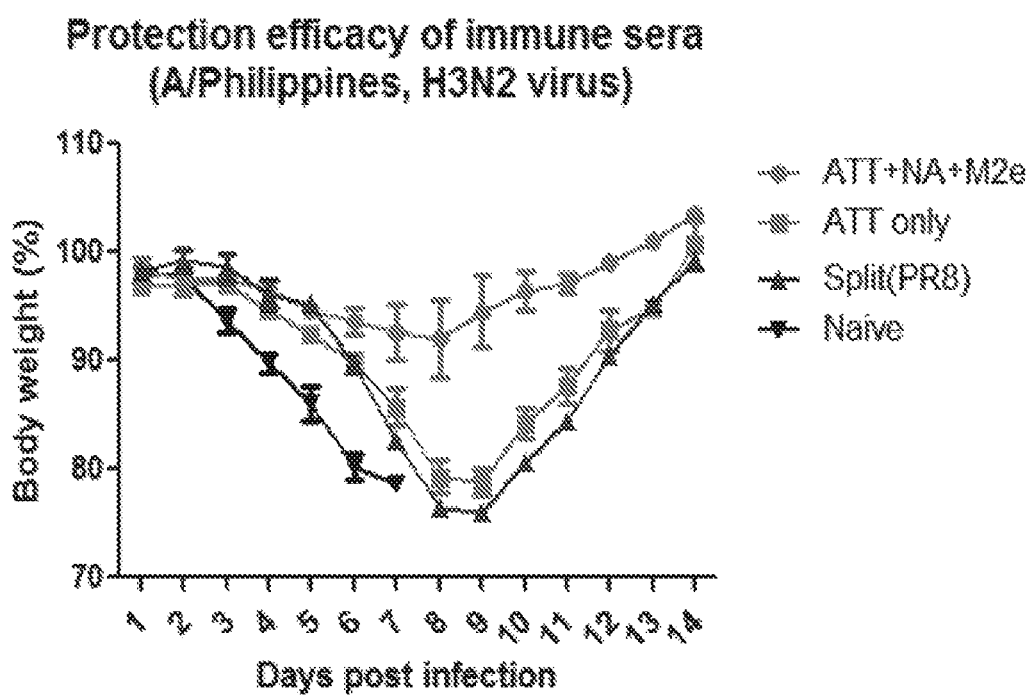
FIG. 26 is a graph showing body weight (%) of mice immunized with LAIV PR8 H1N1 (attenuated only), split vaccine (PR8 H1N1), or LAIV PR8 H1N1 supplemented with neuraminidase (NA N1+N2) proteins and tandem repeat M2e5x VLPs.

Example 6: Further Improved Cross Protective Efficacy of Recombinant Live Attenuated Influenza Virus Vaccines (LAIV) by Supplementing with Neuraminidase and/or M2e Epitope-Based Vaccines Experiments were conducted to test whether the cross protective efficacies of live attenuated influenza vaccines could be further improved by supplementing with neuraminidase and/or M2e epitope-based vaccines. Groups of mice were immunized with LAIV PR8 H1N1 (attenuated only), split vaccine (PR8 H1N1), or supplemented ATT with neuraminidase (NA N1+N2) proteins and tandem repeat M2e5x VLPs (FIG. 26). The immune sera were collected at 3 weeks after single immunization. To determine the cross protective efficacies, the immune sera were mixed with a lethal dose of H3N2 virus (A/Philippines/82). Then a mixture of immune sera and H3N2 virus was used to infect naïve mice (FIG. 26). The cross protective efficacy was determined by monitoring body weight changes. All naïve mice (naïve sera+H3N2 virus) died of infection (FIG. 26). Naïve mice that received immune sera from ATT only or split PR8 vaccination showed severe weight loss after inoculation of virus mixtures into naïve mice (ATT only, Split, FIG. 26). Minimum weight loss around 5-6% was observed in naive mice that received immune sera from supplemented vaccination after inoculation of virus mixtures into naïve mice (ATT+NA+M2e, FIG. 26). These results provide a proof-of-concept that supplementing recombinant live attenuated influenza vaccines (recombinant LAIV) or recombinant inactivated split vaccines with neuraminidase (N1+N2 NA) and/or M2e epitope-based vaccines.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A recombinant influenza virus comprising a chimeric hemagglutinin (HA) fusion protein, wherein the HA fusion protein comprises an influenza A hemagglutinin (HA) protein or fragment thereof comprising at least the HA head domain, and
   one or more repeats of three or more influenza virus matrix protein 2 extracellular (M2e) domains.

2. The recombinant influenza virus of claim 1, wherein the chimeric HA fusion protein comprises one or more M2e domains from a human influenza A subtype, one or more M2e domains from a swine influenza A subtype, and one or more M2e domains from an avian influenza A subtype.

3. The recombinant influenza virus of claim 1, wherein at least one M2e domain comprises a partial or full human, swine, or avian M2e domain comprising the amino acid sequence SEQ ID NO:3 or an amino acid sequence having at least 90% sequence identity to SEQ ID NO:3, and wherein at least one M2e domain comprises an avian M2e domain comprising the amino acid sequence SEQ ID NO:4 or an amino acid sequence having at least 90% sequence identity to SEQ ID NO:4.

4. The recombinant influenza virus of claim 1, wherein the chimeric HA fusion protein further comprises a signal peptide at the N-terminus or in the middle HA head domain of the HA protein.

5. The recombinant influenza virus of claim 1, wherein the HA protein is derived from a seasonal or pandemic influenza virus.

6. The recombinant influenza virus of claim 1, wherein the chimeric HA protein comprises an amino acid sequence having a formula selected from the group consisting of:

$$X_1\text{-}([hM2e]_n\text{-}[sM2e]_n\text{-}[aM2e]_n)_n\text{-}X_2,$$

$$X_1\text{-}([hM2e]_n\text{-}[aM2e]_n\text{-}[sM2e]_n)_n\text{-}X_2,$$

$$X_1\text{-}([sM2e]_n\text{-}[hM2e]_n\text{-}[aM2e]_n)_n\text{-}X_2,$$

$$X_1\text{-}([sM2e]_n\text{-}[aM2e]_n\text{-}[hM2e]_n)_n\text{-}X_2,$$

$$X_1\text{-}([aM2e]_n\text{-}[sM2e]_n\text{-}[hM2e]_n)_n\text{-}X_2, \text{ and}$$

$$X_1\text{-}([aM2e]_n\text{-}[hM2e]_n\text{-}[sM2e]_n)_n\text{-}X_2;$$

wherein "$X_1$" consists of a signal peptide of HA protein,
wherein "$X_2$" consists of an HA protein domain other than the signal peptide,
wherein "hM2e" consists of a human M2e domain,
wherein "sM2e" consists of a swine M2e domain,
wherein "aM2e" consists of an avian M2e domain,
wherein each "n" is independently an integer from one to five, and
wherein "-" consists of a peptide linker or a peptide bond.

7. The recombinant influenza virus of claim 1, wherein the chimeric HA fusion protein comprises an amino acid sequence having a formula selected from the group consisting of:

$$X_3\text{-}[hM2e]\text{-}X_4,$$

$$X_3\text{-}[sM2e]\text{-}X_4, \text{ and}$$

$$X_3\text{-}[aM2e]\text{-}X_4,$$

wherein "$X_3$" consists of from aa1 to aa171 of an HA derived from A/PR8 virus or seasonal influenza vaccine strains,
wherein "hM2e" consists of a human M2e domain,
wherein "sM2e" consists of a swine M2e domain,
wherein "aM2e" consists of an avian M2e domain,
wherein "$X_4$" consists of from aa172 to the end of HA derived from A/PR8 virus or seasonal influenza vaccine strains,
wherein "-" consists of a peptide linker or a peptide bond.

8. The recombinant influenza virus of claim 1, wherein the chimeric HA fusion protein comprises an amino acid sequence having a formula selected from the group consisting of:

$$X_1\text{-}(hM2e\text{-}hM2e\text{-}sM2e\text{-}aM2e\text{-}aM2e)_n\text{-}X_2,$$

$$X_3\text{-}[hM2e]\text{-}X_4,$$

$$X_3\text{-}[sM2e]\text{-}X_4, \text{ and}$$

$$X_3\text{-}[aM2e]\text{-}X_4,$$

wherein "$X_1$" consists of a signal peptide of HA protein,
wherein "$X_2$" consists of an HA protein domain other than the signal peptide,
wherein "$X_3$" consists of from aa1 to aa171 of an HA derived from A/PR8 virus or seasonal influenza vaccine strains,
wherein "$X_4$" consists of from aa172 to the end of HA derived from A/PR8 virus or seasonal influenza vaccine strains,
wherein "hM2e" consists of a human M2e domain,
wherein "sM2e" consists of a swine M2e domain,
wherein "aM2e" consists of an avian M2e domain,
wherein each "n" is independently an integer from one to five, and
wherein "-" consists of a peptide linker or a peptide bond.

9. The recombinant influenza virus of claim 1 formulated as a whole inactivated virus, split viral vaccine, or live attenuated influenza vaccine.

10. The recombinant influenza virus of claim 1, wherein the influenza virus is an A/Ann Arbor/6/60 (H2N2), A/PR/8/34 (H1N1), or A/Leningrad/134/17/57 (H2N2), influenza virus type A strain.

11. A cross-protective vaccine comprising the recombinant influenza virus of claim 1.

12. The vaccine of claim 11, further comprising an adjuvant.

13. The vaccine of claim 12, wherein the adjuvant is selected from the group consisting of AS04 (alum plus monophosphoryl lipid A), MF59 (oil-in-water emulsion adjuvant), and toll-like receptor agonist adjuvants (monophosphoryl lipid A plus CpG).

14. The vaccine of claim 11, further comprising a neuraminidase.

15. A method of vaccinating a subject for influenza A, comprising administering the vaccine of claim 11 to a subject in need thereof by intranasal, intramuscular, subcutaneous, microneedle skin, transdermal, or sublingual administration.

* * * * *